United States Patent
Gall et al.

(10) Patent No.: US 9,681,531 B2
(45) Date of Patent: Jun. 13, 2017

(54) CONTROL SYSTEM FOR A PARTICLE ACCELERATOR

(71) Applicant: Mevion Medical Systems, Inc., Littleton, MA (US)

(72) Inventors: Kenneth P. Gall, Harvard, MA (US); Stanley Rosenthal, Wayland, MA (US); Thomas C. Sobczynski, Arlington, MA (US); Adam C. Molzahn, Leominster, MA (US)

(73) Assignee: Mevion Medical Systems, Inc., Littleton, MA (US)

( * ) Notice: Subject to any disclaimer, the term of this patent is extended or adjusted under 35 U.S.C. 154(b) by 0 days.

(21) Appl. No.: 14/038,967

(22) Filed: Sep. 27, 2013

(65) Prior Publication Data
US 2014/0091734 A1    Apr. 3, 2014

Related U.S. Application Data

(60) Provisional application No. 61/707,645, filed on Sep. 28, 2012.

(51) Int. Cl.
*H05H 13/02*      (2006.01)
*A61N 5/10*       (2006.01)
*H05H 7/00*       (2006.01)

(52) U.S. Cl.
CPC .......... *H05H 13/02* (2013.01); *A61N 5/1065* (2013.01); *A61N 5/1077* (2013.01);
(Continued)

(58) Field of Classification Search
CPC ............. H05H 13/02; H05H 2007/004; A61N 5/1065; A61N 5/1077; A61N 5/1048; A61N 2005/1095; A61N 5/1081
See application file for complete search history.

(56) References Cited

U.S. PATENT DOCUMENTS 2,280,606 A    4/1942    Van et al.
2,492,324 A    12/1949   Salisbury
(Continued)

FOREIGN PATENT DOCUMENTS

AU    2005267078 A1    2/2006
CA    2629333          5/2007
(Continued)

OTHER PUBLICATIONS

US 8,581,524, 11/2013, O'Neal et al. (withdrawn)
(Continued)

*Primary Examiner* — Jung Kim
(74) *Attorney, Agent, or Firm* — Choate, Hall & Stewart LLP; Paul Pysher

(57) ABSTRACT

An example particle therapy system includes a particle accelerator to output a particle beam, where the particle accelerator includes: a particle source to provide pulses of ionized plasma to a cavity, where each pulse of the particle source has a pulse width corresponding to a duration of operation of the particle source to produce the corresponding pulse, and where the particle beam is based on the pulses of ionized plasma; and a modulator wheel having different thicknesses, where each thickness extends across a different circumferential length of the modulator wheel, and where the modulator wheel is arranged to receive a precursor to the particle beam and is configured to create a spread-out Bragg peak for the particle beam.

25 Claims, 19 Drawing Sheets

(52) U.S. Cl.
CPC .... *A61N 5/1048* (2013.01); *A61N 2005/1095* (2013.01); *H05H 2007/004* (2013.01)

(56) References Cited

U.S. PATENT DOCUMENTS

| | | | |
|---|---|---|---|
| 2,615,129 A | 10/1952 | McMillan | |
| 2,616,042 A | 10/1952 | Weeks | |
| 2,659,000 A | 11/1953 | Salisbury | |
| 2,701,304 A | 2/1955 | Dickinson | |
| 2,789,222 A | 4/1957 | Martin | |
| 3,175,131 A | 3/1965 | Burleigh et al. | |
| 3,432,721 A | 3/1969 | Naydan et al. | |
| 3,582,650 A | 6/1971 | Avery | |
| 3,679,899 A | 7/1972 | Dimeff | |
| 3,689,847 A | 9/1972 | Verster | |
| 3,757,118 A | 9/1973 | Hodge et al. | |
| 3,868,522 A | 2/1975 | Bigham et al. | |
| 3,886,367 A | 5/1975 | Castle | |
| 3,925,676 A | 12/1975 | Bigham et al. | |
| 2,958,327 A | 5/1976 | Marancik et al. | |
| 3,955,089 A | 5/1976 | McIntyre et al. | |
| 3,958,327 A | 5/1976 | Marancik et al. | |
| 3,992,625 A | 11/1976 | Schmidt et al. | |
| 4,038,622 A | 7/1977 | Purcell | |
| 4,047,068 A | 9/1977 | Ress et al. | |
| 4,112,306 A | 9/1978 | Nunan | |
| 4,129,784 A | 12/1978 | Tschunt et al. | |
| 4,139,777 A | 2/1979 | Rautenbach | |
| 4,197,510 A | 4/1980 | Szu | |
| 4,220,866 A | 9/1980 | Symmons et al. | |
| 4,230,129 A | 10/1980 | LeVeen | |
| 4,256,966 A | 3/1981 | Heinz | |
| 4,293,772 A | 10/1981 | Stieber | |
| 4,336,505 A | 6/1982 | Meyer | |
| 4,342,060 A | 7/1982 | Gibson | |
| 4,345,210 A | 8/1982 | Tran | |
| 4,353,033 A | 10/1982 | Karasawa | |
| 4,425,506 A | 1/1984 | Brown et al. | |
| 4,490,616 A | 12/1984 | Cipollina et al. | |
| 4,507,614 A | 3/1985 | Prono et al. | |
| 4,507,616 A | 3/1985 | Blosser et al. | |
| 4,589,126 A | 5/1986 | Augustsson et al. | |
| 4,598,208 A | 7/1986 | Brunelli et al. | |
| 4,628,523 A | 12/1986 | Heflin | |
| 4,633,125 A | 12/1986 | Blosser et al. | |
| 4,641,057 A | 2/1987 | Blosser et al. | |
| 4,641,104 A | 2/1987 | Blosser et al. | |
| 4,651,007 A | 3/1987 | Perusek et al. | |
| 4,680,565 A | 7/1987 | Jahnke | |
| 4,705,955 A | 11/1987 | Mileikowsky | |
| 4,710,722 A | 12/1987 | Jahnke | |
| 4,726,046 A | 2/1988 | Nunan | |
| 4,734,653 A | 3/1988 | Jahnke | |
| 4,737,727 A | 4/1988 | Yamada et al. | |
| 4,739,173 A | 4/1988 | Blosser et al. | |
| 4,745,367 A | 5/1988 | Dustmann et al. | |
| 4,754,147 A | 6/1988 | Maughan et al. | |
| 4,763,483 A | 8/1988 | Olsen | |
| 4,767,930 A | 8/1988 | Stieber et al. | |
| 4,769,623 A | 9/1988 | Marsing et al. | |
| 4,771,208 A | 9/1988 | Jongen et al. | |
| 4,783,634 A | 11/1988 | Yamamoto et al. | |
| 4,808,941 A | 2/1989 | Marsing | |
| 4,812,658 A | 3/1989 | Koehler | |
| 4,843,333 A | 6/1989 | Marsing et al. | |
| 4,845,371 A | 7/1989 | Stieber | |
| 4,865,284 A | 9/1989 | Gosis et al. | |
| 4,868,843 A | 9/1989 | Nunan | |
| 4,868,844 A | 9/1989 | Nunan | |
| 4,870,287 A | 9/1989 | Cole et al. | |
| 4,880,985 A | 11/1989 | Jones | |
| 4,894,541 A | 1/1990 | Ono | |
| 4,896,206 A | 1/1990 | Denham | |
| 4,902,993 A | 2/1990 | Krevent | |
| 4,904,949 A | 2/1990 | Wilson | |
| 4,905,267 A | 2/1990 | Miller et al. | |
| 4,917,344 A | 4/1990 | Prechter et al. | |
| 4,943,781 A | 7/1990 | Wilson et al. | |
| 4,945,478 A | 7/1990 | Merickel et al. | |
| 4,968,915 A | 11/1990 | Wilson et al. | |
| 4,987,309 A | 1/1991 | Klasen et al. | |
| 4,992,744 A | 2/1991 | Fujita et al. | |
| 4,996,496 A | 2/1991 | Kitamura et al. | |
| 5,006,759 A | 4/1991 | Krispel | |
| 5,010,562 A | 4/1991 | Hernandez et al. | |
| 5,012,111 A | 4/1991 | Ueda | |
| 5,017,789 A | 5/1991 | Young et al. | |
| 5,017,882 A | 5/1991 | Finlan | |
| 5,036,290 A | 7/1991 | Sonobe et al. | |
| 5,039,057 A | 8/1991 | Prechter et al. | |
| 5,039,867 A | 8/1991 | Nishihara et al. | |
| 5,046,078 A | 9/1991 | Hernandez et al. | |
| 5,072,123 A | 12/1991 | Johnsen | |
| 5,111,042 A | 5/1992 | Sullivan et al. | |
| 5,111,173 A | 5/1992 | Matsuda et al. | |
| 5,117,194 A | 5/1992 | Nakanishi et al. | |
| 5,117,212 A | 5/1992 | Yamamoto et al. | |
| 5,117,829 A | 6/1992 | Miller et al. | |
| 5,148,032 A | 9/1992 | Hernandez | |
| 5,166,531 A | 11/1992 | Huntzinger | |
| 5,189,687 A | 2/1993 | Bova et al. | |
| 5,191,706 A | 3/1993 | Cosden | |
| 5,240,218 A | 8/1993 | Dye | |
| 5,260,579 A | 11/1993 | Yasuda et al. | |
| 5,260,581 A | 11/1993 | Lesyna et al. | |
| 5,278,533 A | 1/1994 | Kawaguchi | |
| 5,285,166 A | 2/1994 | Hiramoto et al. | |
| 5,317,164 A | 5/1994 | Kurokawa | |
| 5,336,891 A | 8/1994 | Crewe | |
| 5,341,104 A | 8/1994 | Anton et al. | |
| 5,349,198 A | 9/1994 | Takanaka | |
| 5,365,742 A | 11/1994 | Boffito et al. | |
| 5,374,913 A | 12/1994 | Pissantezky et al. | |
| 5,382,914 A | 1/1995 | Hamm et al. | |
| 5,401,973 A | 3/1995 | McKeown et al. | |
| 5,405,235 A | 4/1995 | Lebre et al. | |
| 5,434,420 A | 7/1995 | McKeown et al. | |
| 5,440,133 A | 8/1995 | Moyers et al. | |
| 5,451,794 A | 9/1995 | McKeown et al. | |
| 5,461,773 A | 10/1995 | Kawaguchi | |
| 5,463,291 A | 10/1995 | Carroll et al. | |
| 5,464,411 A | 11/1995 | Schulte et al. | |
| 5,492,922 A | 2/1996 | Palkowitz | |
| 5,511,549 A | 4/1996 | Legg et al. | |
| 5,521,469 A | 5/1996 | Laisne | |
| 5,538,942 A | 7/1996 | Koyama et al. | |
| 5,549,616 A | 8/1996 | Schulte et al. | |
| 5,561,697 A | 10/1996 | Takafuji et al. | |
| 5,585,642 A | 12/1996 | Britton et al. | |
| 5,633,747 A | 5/1997 | Nikoonahad | |
| 5,635,721 A | 6/1997 | Bardi et al. | |
| 5,668,371 A | 9/1997 | Deasy et al. | |
| 5,672,878 A | 9/1997 | Yao | |
| 5,691,679 A | 11/1997 | Ackermann et al. | |
| 5,726,448 A | 3/1998 | Smith et al. | |
| 5,727,554 A | 3/1998 | Kalend et al. | |
| 5,730,745 A | 3/1998 | Schulte et al. | |
| 5,751,781 A | 5/1998 | Brown et al. | |
| 5,778,047 A | 7/1998 | Mansfield et al. | |
| 5,783,914 A | 7/1998 | Hiramoto et al. | |
| 5,784,431 A | 7/1998 | Kalend et al. | |
| 5,797,924 A | 8/1998 | Schulte et al. | |
| 5,811,944 A | 9/1998 | Sampayan et al. | |
| 5,818,058 A | 10/1998 | Nakanishi et al. | |
| 5,821,705 A | 10/1998 | Caporasco et al. | |
| 5,825,845 A | 10/1998 | Blair et al. | |
| 5,841,237 A | 11/1998 | Alton | |
| 5,846,043 A | 12/1998 | Spath | |
| 5,851,182 A | 12/1998 | Sahadevan | |
| 5,866,912 A | 2/1999 | Slater et al. | |
| 5,874,811 A | 2/1999 | Finlan et al. | |
| 5,895,926 A | 4/1999 | Britton et al. | |
| 5,917,293 A | 6/1999 | Saito et al. | |
| 5,920,601 A | 7/1999 | Nigg et al. | |

(56) References Cited

U.S. PATENT DOCUMENTS

| | | |
|---|---|---|
| 5,929,458 A | 7/1999 | Nemezawa et al. |
| 5,963,615 A | 10/1999 | Egley et al. |
| 5,993,373 A | 11/1999 | Nonaka et al. |
| 6,008,499 A | 12/1999 | Hiramoto et al. |
| 6,034,377 A | 3/2000 | Pu |
| 6,057,655 A | 5/2000 | Jongen |
| 6,061,426 A | 5/2000 | Linders et al. |
| 6,064,807 A | 5/2000 | Arai et al. |
| 6,066,851 A | 5/2000 | Madono et al. |
| 6,080,992 A | 6/2000 | Nonaka et al. |
| 6,087,670 A | 7/2000 | Hiramoto et al. |
| 6,094,760 A | 8/2000 | Nonaka et al. |
| 6,118,848 A | 9/2000 | Reiffel |
| 6,140,021 A | 10/2000 | Nakasuji et al. |
| 6,144,875 A | 11/2000 | Sachweikard et al. |
| 6,158,708 A | 12/2000 | Egley et al. |
| 6,207,952 B1 | 3/2001 | Kan et al. |
| 6,219,403 B1 | 4/2001 | Nishihara |
| 6,222,905 B1 | 4/2001 | Yoda et al. |
| 6,241,671 B1 | 6/2001 | Ritter et al. |
| 6,246,066 B1 | 6/2001 | Yuehu |
| 6,256,591 B1 | 7/2001 | Yoda et al. |
| 6,265,837 B1 | 7/2001 | Akiyama et al. |
| 6,268,610 B1 | 7/2001 | Pu |
| 6,278,239 B1 | 8/2001 | Caporasco et al. |
| 6,279,579 B1 | 8/2001 | Riaziat et al. |
| 6,307,914 B1 | 10/2001 | Kunieda et al. |
| 6,316,776 B1 | 11/2001 | Hiramoto et al. |
| 6,366,021 B1 | 4/2002 | Meddaugh et al. |
| 6,369,585 B2 | 4/2002 | Yao |
| 6,380,545 B1 | 4/2002 | Yan |
| 6,407,505 B1 | 6/2002 | Bertsche |
| 6,417,634 B1 | 7/2002 | Bergstrom |
| 6,433,336 B1 | 8/2002 | Jongen et al. |
| 6,433,349 B2 | 8/2002 | Akiyama et al. |
| 6,433,494 B1 | 8/2002 | Kulish et al. |
| 6,441,569 B1 | 8/2002 | Janzow |
| 6,443,349 B1 | 9/2002 | Van Der Burg |
| 6,465,957 B1 | 10/2002 | Whitham et al. |
| 6,472,834 B2 | 10/2002 | Hiramoto et al. |
| 6,476,403 B1 | 11/2002 | Dolinskii et al. |
| 6,492,922 B1 | 12/2002 | New |
| 6,493,424 B2 | 12/2002 | Whitham |
| 6,498,444 B1 | 12/2002 | Hanna et al. |
| 6,501,981 B1 | 12/2002 | Schweikard et al. |
| 6,519,316 B1 | 2/2003 | Collins |
| 6,576,916 B2 | 6/2003 | Smith et al. |
| 6,593,696 B2 | 7/2003 | Ding et al. |
| 6,594,336 B2 | 7/2003 | Nishizawa et al. |
| 6,600,164 B1 | 7/2003 | Badura et al. |
| 6,617,598 B1 | 9/2003 | Matsuda |
| 6,621,889 B1 | 9/2003 | Mostafavi |
| 6,639,234 B1 | 10/2003 | Badura et al. |
| 6,646,383 B2 | 11/2003 | Bertsche et al. |
| 6,670,618 B1 | 12/2003 | Hartmann et al. |
| 6,683,318 B1 | 1/2004 | Haberer et al. |
| 6,683,426 B1 | 1/2004 | Kleeven |
| 6,693,283 B2 | 2/2004 | Eickhoff et al. |
| 6,710,362 B2 | 3/2004 | Kraft et al. |
| 6,713,773 B1 | 3/2004 | Lyons et al. |
| 6,713,976 B1 | 3/2004 | Zumoto et al. |
| 6,717,162 B1 | 4/2004 | Jongen |
| 6,736,831 B1 | 5/2004 | Hartmann et al. |
| 6,745,072 B1 | 6/2004 | Badura et al. |
| 6,769,806 B2 | 8/2004 | Moyers |
| 6,774,383 B2 | 8/2004 | Norimine et al. |
| 6,777,689 B2 | 8/2004 | Nelson |
| 6,777,700 B2 | 8/2004 | Yanagisawa et al. |
| 6,780,149 B2 | 8/2004 | Schulte |
| 6,799,068 B1 | 9/2004 | Hartmann et al. |
| 6,800,866 B2 | 10/2004 | Amemiya et al. |
| 6,803,591 B2 | 10/2004 | Muramatsu et al. |
| 6,814,694 B1 | 11/2004 | Pedroni |
| 6,822,244 B2 | 11/2004 | Beloussov et al. |
| 6,853,142 B2 | 2/2005 | Chistyakov |
| 6,853,703 B2 | 2/2005 | Svatos et al. |
| 6,864,770 B2 | 3/2005 | Nemoto et al. |
| 6,865,254 B2 | 3/2005 | Nafstadius |
| 6,873,123 B2 | 3/2005 | Marchand et al. |
| 6,891,177 B1 | 5/2005 | Kraft et al. |
| 6,891,924 B1 | 5/2005 | Yoda et al. |
| 6,894,300 B2 | 5/2005 | Reimoser et al. |
| 6,897,451 B2 | 5/2005 | Kaercher et al. |
| 6,914,396 B1 | 7/2005 | Symons et al. |
| 6,936,832 B2 | 8/2005 | Norimine et al. |
| 6,953,943 B2 | 10/2005 | Yanagisawa et al. |
| 6,965,116 B1 | 11/2005 | Wagner et al. |
| 6,969,194 B1 | 11/2005 | Nafstadius |
| 6,979,832 B2 | 12/2005 | Yanagisawa et al. |
| 6,984,835 B2 | 1/2006 | Harada |
| 6,992,312 B2 | 1/2006 | Yanagisawa et al. |
| 6,993,112 B2 | 1/2006 | Hesse |
| 7,008,105 B2 | 3/2006 | Amann et al. |
| 7,011,447 B2 | 3/2006 | Moyers |
| 7,012,267 B2 | 3/2006 | Moriyama et al. |
| 7,014,361 B1 | 3/2006 | Ein-Gal |
| 7,026,636 B2 | 4/2006 | Yanagisawa et al. |
| 7,038,403 B2 | 5/2006 | Mastrangeli et al. |
| 7,041,479 B2 | 5/2006 | Swartz et al. |
| 7,045,781 B2 | 5/2006 | Adamec et al. |
| 7,049,613 B2 | 5/2006 | Yanagisawa et al. |
| 7,053,389 B2 | 5/2006 | Yanagisawa et al. |
| 7,054,801 B2 | 5/2006 | Sakamoto et al. |
| 7,060,997 B2 | 6/2006 | Norimine et al. |
| 7,071,479 B2 | 7/2006 | Yanagisawa et al. |
| 7,073,508 B2 | 7/2006 | Moyers |
| 7,081,619 B2 | 7/2006 | Bashkirov et al. |
| 7,084,410 B2 | 8/2006 | Beloussov et al. |
| 7,091,478 B2 | 8/2006 | Haberer |
| 7,102,144 B2 | 9/2006 | Matsuda et al. |
| 7,122,811 B2 | 10/2006 | Matsuda et al. |
| 7,122,966 B2 | 10/2006 | Norling et al. |
| 7,122,978 B2 | 10/2006 | Nakanishi et al. |
| 7,135,678 B2 | 11/2006 | Wang et al. |
| 7,138,771 B2 | 11/2006 | Bechthold et al. |
| 7,154,107 B2 | 12/2006 | Yanagisawa et al. |
| 7,154,108 B2 | 12/2006 | Tadokoro et al. |
| 7,154,991 B2 | 12/2006 | Earnst et al. |
| 7,162,005 B2 | 1/2007 | Bjorkholm |
| 7,173,264 B2 | 2/2007 | Moriyama et al. |
| 7,173,265 B2 | 2/2007 | Miller et al. |
| 7,173,385 B2 | 2/2007 | Caporaso et al. |
| 7,186,991 B2 | 3/2007 | Kato et al. |
| 7,193,227 B2 | 3/2007 | Hiramoto et al. |
| 7,199,382 B2 | 4/2007 | Rigney et al. |
| 7,208,748 B2 | 4/2007 | Sliski et al. |
| 7,212,608 B2 | 5/2007 | Nagamine et al. |
| 7,212,609 B2 | 5/2007 | Nagamine et al. |
| 7,221,733 B1 | 5/2007 | Takai et al. |
| 7,227,161 B2 | 6/2007 | Matsuda et al. |
| 7,247,869 B2 | 7/2007 | Tadokoro et al. |
| 7,257,191 B2 | 8/2007 | Sommer |
| 7,259,529 B2 | 8/2007 | Tanaka |
| 7,262,424 B2 | 8/2007 | Moriyama et al. |
| 7,262,565 B2 | 8/2007 | Fujisawa |
| 7,274,018 B2 | 9/2007 | Adamec et al. |
| 7,280,633 B2 | 10/2007 | Cheng et al. |
| 7,295,649 B2 | 11/2007 | Johnsen |
| 7,297,967 B2 | 11/2007 | Yanagisawa et al. |
| 7,301,162 B2 | 11/2007 | Matsuda et al. |
| 7,307,264 B2 | 12/2007 | Brusasco et al. |
| 7,317,192 B2 | 1/2008 | Ma |
| 7,318,805 B2 | 1/2008 | Schweikard et al. |
| 7,319,231 B2 | 1/2008 | Moriyama et al. |
| 7,319,336 B2 | 1/2008 | Baur et al. |
| 7,331,713 B2 | 2/2008 | Moyers |
| 7,332,880 B2 | 2/2008 | Ina et al. |
| 7,345,291 B2 | 3/2008 | Kats |
| 7,345,292 B2 | 3/2008 | Moriyama et al. |
| 7,348,557 B2 | 3/2008 | Armit |
| 7,348,579 B2 | 3/2008 | Pedroni |
| 7,351,988 B2 | 4/2008 | Naumann et al. |
| 7,355,189 B2 | 4/2008 | Yanagisawa et al. |
| 7,368,740 B2 | 5/2008 | Beloussov et al. |

(56) References Cited

U.S. PATENT DOCUMENTS

| | | |
|---|---|---|
| 7,372,053 B2 | 5/2008 | Yamashita et al. |
| 7,378,672 B2 | 5/2008 | Harada |
| 7,381,979 B2 | 6/2008 | Yamashita et al. |
| 7,397,054 B2 | 7/2008 | Natori et al. |
| 7,397,901 B1 | 7/2008 | Johnsen |
| 7,398,309 B2 | 7/2008 | Baumann et al. |
| 7,402,822 B2 | 7/2008 | Guertin et al. |
| 7,402,823 B2 | 7/2008 | Guertin et al. |
| 7,402,824 B2 | 7/2008 | Guertin et al. |
| 7,402,963 B2 | 7/2008 | Sliski |
| 7,405,407 B2 | 7/2008 | Hiramoto et al. |
| 7,425,717 B2 | 9/2008 | Matsuda et al. |
| 7,432,516 B2 | 10/2008 | Peggs et al. |
| 7,439,528 B2 | 10/2008 | Nishiuchi et al. |
| 7,446,328 B2 | 11/2008 | Rigney et al. |
| 7,446,490 B2 | 11/2008 | Jongen et al. |
| 7,449,701 B2 | 11/2008 | Fujimaki et al. |
| 7,453,076 B2 | 11/2008 | Welch et al. |
| 7,456,415 B2 | 11/2008 | Yanagisawa et al. |
| 7,465,944 B2 | 12/2008 | Ueno et al. |
| 7,466,085 B2 | 12/2008 | Nutt |
| 7,468,506 B2 | 12/2008 | Rogers et al. |
| 7,473,913 B2 | 1/2009 | Hermann et al. |
| 7,476,867 B2 | 1/2009 | Fritsch et al. |
| 7,476,883 B2 | 1/2009 | Nutt |
| 7,482,606 B2 | 1/2009 | Groezinger et al. |
| 7,491,161 B2 | 2/2009 | Taguchi |
| 7,492,556 B2 | 2/2009 | Atkins et al. |
| 7,507,975 B2 | 3/2009 | Mohr |
| 7,518,108 B2 | 4/2009 | Frey et al. |
| 7,525,104 B2 | 4/2009 | Harada |
| 7,541,905 B2 | 6/2009 | Antaya |
| 7,547,901 B2 | 6/2009 | Guertin et al. |
| 7,554,096 B2 | 6/2009 | Ward et al. |
| 7,554,097 B2 | 6/2009 | Ward et al. |
| 7,555,103 B2 | 6/2009 | Johnsen |
| 7,557,358 B2 | 7/2009 | Ward et al. |
| 7,557,359 B2 | 7/2009 | Ward et al. |
| 7,557,360 B2 | 7/2009 | Ward et al. |
| 7,557,361 B2 | 7/2009 | Ward et al. |
| 7,560,715 B2 | 7/2009 | Pedroni |
| 7,560,717 B2 | 7/2009 | Matsuda et al. |
| 7,567,694 B2 | 7/2009 | Lu et al. |
| 7,574,251 B2 | 8/2009 | Lu et al. |
| 7,576,499 B2 | 8/2009 | Caporaso et al. |
| 7,579,603 B2 | 8/2009 | Birgy et al. |
| 7,579,610 B2 | 8/2009 | Grozinger et al. |
| 7,582,866 B2 | 9/2009 | Furuhashi et al. |
| 7,582,885 B2 | 9/2009 | Katagiri et al. |
| 7,582,886 B2 | 9/2009 | Trbojevic |
| 7,586,112 B2 | 9/2009 | Chiba et al. |
| 7,598,497 B2 | 10/2009 | Yamamoto et al. |
| 7,609,009 B2 | 10/2009 | Tanaka et al. |
| 7,609,809 B2 | 10/2009 | Kapatoes et al. |
| 7,609,811 B1 | 10/2009 | Siljamaki et al. |
| 7,615,942 B2 | 11/2009 | Sanders et al. |
| 7,626,347 B2 | 12/2009 | Sliski |
| 7,627,267 B2 | 12/2009 | Saiki |
| 7,629,598 B2 | 12/2009 | Harada |
| 7,639,853 B2 | 12/2009 | Olivera et al. |
| 7,639,854 B2 | 12/2009 | Schnarr et al. |
| 7,643,661 B2 | 1/2010 | Ruchala et al. |
| 7,656,258 B1 | 2/2010 | Antaya et al. |
| 7,659,521 B2 | 2/2010 | Pedroni |
| 7,659,528 B2 | 2/2010 | Uematsu |
| 7,668,291 B2 | 2/2010 | Nord et al. |
| 7,672,429 B2 | 3/2010 | Urano et al. |
| 7,679,073 B2 | 3/2010 | Urano et al. |
| 7,682,078 B2 | 3/2010 | Rietzel |
| 7,692,166 B2 | 4/2010 | Muraki et al. |
| 7,692,168 B2 | 4/2010 | Moriyama et al. |
| 7,696,499 B2 | 4/2010 | Miller et al. |
| 7,696,847 B2 | 4/2010 | Antaya |
| 7,701,677 B2 | 4/2010 | Schultz et al. |
| 7,709,818 B2 | 5/2010 | Matsuda et al. |
| 7,710,051 B2 | 5/2010 | Caporaso et al. |
| 7,718,982 B2 | 5/2010 | Sliski |
| 7,728,311 B2 | 6/2010 | Gall |
| 7,746,978 B2 | 6/2010 | Cheng et al. |
| 7,755,305 B2 | 7/2010 | Umezawa et al. |
| 7,759,642 B2 | 7/2010 | Nir |
| 7,763,867 B2 | 7/2010 | Birgy et al. |
| 7,767,988 B2 | 8/2010 | Kaiser et al. |
| 7,770,231 B2 | 8/2010 | Prater et al. |
| 7,772,577 B2 | 8/2010 | Saito et al. |
| 7,773,723 B2 | 8/2010 | Nord et al. |
| 7,773,788 B2 | 8/2010 | Lu et al. |
| 7,778,488 B2 | 8/2010 | Nord et al. |
| 7,783,010 B2 | 8/2010 | Clayton |
| 7,784,127 B2 | 8/2010 | Kuro et al. |
| 7,786,451 B2 | 8/2010 | Ward et al. |
| 7,786,452 B2 | 8/2010 | Ward et al. |
| 7,789,560 B2 | 9/2010 | Moyers |
| 7,791,051 B2 | 9/2010 | Beloussov et al. |
| 7,796,731 B2 | 9/2010 | Nord et al. |
| 7,801,269 B2 | 9/2010 | Cravens et al. |
| 7,801,270 B2 | 9/2010 | Nord et al. |
| 7,801,988 B2 | 9/2010 | Baumann et al. |
| 7,807,982 B2 | 10/2010 | Nishiuchi et al. |
| 7,809,107 B2 | 10/2010 | Nord et al. |
| 7,812,319 B2 | 10/2010 | Diehl et al. |
| 7,812,326 B2 | 10/2010 | Grozinger et al. |
| 7,816,657 B2 | 10/2010 | Hansmann et al. |
| 7,817,778 B2 | 10/2010 | Nord et al. |
| 7,817,836 B2 | 10/2010 | Chao et al. |
| 7,834,334 B2 | 11/2010 | Grozinger et al. |
| 7,834,336 B2 | 11/2010 | Boeh et al. |
| 7,835,494 B2 | 11/2010 | Nord et al. |
| 7,835,502 B2 | 11/2010 | Spence et al. |
| 7,839,972 B2 | 11/2010 | Ruchala et al. |
| 7,839,973 B2 | 11/2010 | Nord et al. |
| 7,848,488 B2 | 12/2010 | Mansfield |
| 7,857,756 B2 | 12/2010 | Warren et al. |
| 7,860,216 B2 | 12/2010 | Jongen et al. |
| 7,860,550 B2 | 12/2010 | Saracen et al. |
| 7,868,301 B2 | 1/2011 | Diehl |
| 7,875,861 B2 | 1/2011 | Huttenberger et al. |
| 7,875,868 B2 | 1/2011 | Moriyama et al. |
| 7,881,431 B2 | 2/2011 | Aoi et al. |
| 7,894,574 B1 | 2/2011 | Nord et al. |
| 7,906,769 B2 | 3/2011 | Blasche et al. |
| 7,914,734 B2 | 3/2011 | Livingston |
| 7,919,765 B2 | 4/2011 | Timmer |
| 7,920,040 B2 | 4/2011 | Antaya et al. |
| 7,920,675 B2 | 4/2011 | Lomax et al. |
| 7,928,415 B2 | 4/2011 | Bert et al. |
| 7,934,869 B2 | 5/2011 | Ivanov et al. |
| 7,940,881 B2 | 5/2011 | Jongen et al. |
| 7,943,913 B2 | 5/2011 | Balakin |
| 7,947,969 B2 | 5/2011 | Pu |
| 7,949,096 B2 | 5/2011 | Cheng et al. |
| 7,950,587 B2 | 5/2011 | Henson et al. |
| 7,960,710 B2 | 6/2011 | Kruip et al. |
| 7,961,844 B2 | 6/2011 | Takeda et al. |
| 7,977,648 B2 | 7/2011 | Westerly et al. |
| 7,977,656 B2 | 7/2011 | Fujimaki et al. |
| 7,982,198 B2 | 7/2011 | Nishiuchi et al. |
| 7,982,416 B2 | 7/2011 | Tanaka et al. |
| 7,984,715 B2 | 7/2011 | Moyers |
| 7,986,768 B2 | 7/2011 | Nord et al. |
| 7,987,053 B2 | 7/2011 | Schaffner |
| 7,989,785 B2 | 8/2011 | Emhofer et al. |
| 7,990,524 B2 | 8/2011 | Jureller et al. |
| 7,997,553 B2 | 8/2011 | Sloan et al. |
| 8,002,466 B2 | 8/2011 | Von Neubeck et al. |
| 8,003,964 B2 | 8/2011 | Stark et al. |
| 8,009,803 B2 | 8/2011 | Nord et al. |
| 8,009,804 B2 | 8/2011 | Siljamaki et al. |
| 8,039,822 B2 | 10/2011 | Rietzel |
| 8,041,006 B2 | 10/2011 | Boyden et al. |
| 8,044,364 B2 | 10/2011 | Yamamoto |
| 8,049,187 B2 | 11/2011 | Tachikawa |
| 8,053,508 B2 | 11/2011 | Korkut et al. |
| 8,053,739 B2 | 11/2011 | Rietzel |

(56) References Cited

U.S. PATENT DOCUMENTS

| | | |
|---|---|---|
| 8,053,745 B2 | 11/2011 | Moore |
| 8,053,746 B2 | 11/2011 | Timmer et al. |
| 8,067,748 B2 | 11/2011 | Balakin |
| 8,069,675 B2 | 12/2011 | Radovinsky et al. |
| 8,071,966 B2 | 12/2011 | Kaiser et al. |
| 8,080,801 B2 | 12/2011 | Safai |
| 8,085,899 B2 | 12/2011 | Nord et al. |
| 8,089,054 B2 | 1/2012 | Balakin |
| 8,093,564 B2 | 1/2012 | Balakin |
| 8,093,568 B2 | 1/2012 | Mackie et al. |
| 8,111,125 B2 | 2/2012 | Antaya et al. |
| 8,129,699 B2 | 3/2012 | Balakin |
| 8,144,832 B2 | 3/2012 | Balakin |
| 8,173,981 B2 | 5/2012 | Trbojevic |
| 8,188,688 B2 | 5/2012 | Balakin |
| 8,198,607 B2 | 6/2012 | Balakin |
| 8,222,613 B2 | 7/2012 | Tajiri et al. |
| 8,227,768 B2 | 7/2012 | Smick et al. |
| 8,232,536 B2 | 7/2012 | Harada |
| 8,288,742 B2 | 10/2012 | Balakin |
| 8,291,717 B2 | 10/2012 | Radovinsky et al. |
| 8,294,127 B2 | 10/2012 | Tachibana |
| 8,304,725 B2 | 11/2012 | Komuro et al. |
| 8,304,750 B2 | 11/2012 | Preikszas et al. |
| 8,309,941 B2 | 11/2012 | Balakin |
| 8,330,132 B2 | 12/2012 | Guertin et al. |
| 8,334,520 B2 | 12/2012 | Otaka et al. |
| 8,335,397 B2 | 12/2012 | Takane et al. |
| 8,344,340 B2 | 1/2013 | Gall et al. |
| 8,350,214 B2 | 1/2013 | Otaki et al. |
| 8,368,038 B2 | 2/2013 | Balakin |
| 8,368,043 B2 | 2/2013 | Havelange et al. |
| 8,373,143 B2 | 2/2013 | Balakin |
| 8,373,145 B2 | 2/2013 | Balakin |
| 8,373,146 B2 | 2/2013 | Balakin |
| 8,378,299 B2 | 2/2013 | Frosien |
| 8,378,321 B2 | 2/2013 | Balakin |
| 8,382,943 B2 | 2/2013 | Clark |
| 8,389,949 B2 | 3/2013 | Harada et al. |
| 8,399,866 B2 | 3/2013 | Balakin |
| 8,405,042 B2 | 3/2013 | Honda et al. |
| 8,405,056 B2 | 3/2013 | Amaldi et al. |
| 8,415,643 B2 | 4/2013 | Balakin |
| 8,416,918 B2 | 4/2013 | Nord et al. |
| 8,421,041 B2 | 4/2013 | Balakin |
| 8,426,833 B2 | 4/2013 | Trbojevic |
| 8,436,323 B2 | 5/2013 | Iseki et al. |
| 8,440,987 B2 | 5/2013 | Stephani et al. |
| 8,445,872 B2 | 5/2013 | Behrens et al. |
| 8,466,441 B2 | 6/2013 | Iwata et al. |
| 8,472,583 B2 | 6/2013 | Star-Lack et al. |
| 8,483,357 B2 | 7/2013 | Siljamaki et al. |
| 8,487,278 B2 | 7/2013 | Balakin |
| 8,552,406 B2 | 10/2013 | Phaneuf et al. |
| 8,552,408 B2 | 10/2013 | Hanawa et al. |
| 8,569,717 B2 | 10/2013 | Balakin |
| 8,575,563 B2 | 11/2013 | Cameron et al. |
| 8,581,215 B2 | 11/2013 | Balakin |
| 8,581,523 B2 | 11/2013 | Gall et al. |
| 8,581,525 B2 | 11/2013 | Antaya et al. |
| 8,637,833 B2 | 1/2014 | Balakin |
| 8,653,314 B2 | 2/2014 | Pelati et al. |
| 8,653,473 B2 | 2/2014 | Yajima |
| 8,791,435 B2 | 7/2014 | Balakin |
| 8,901,509 B2 | 12/2014 | Balakin |
| 8,905,908 B2 | 12/2014 | Matsuguma et al. |
| 8,952,634 B2 | 2/2015 | Sliski et al. |
| 8,963,112 B1 | 2/2015 | Balakin |
| 8,970,137 B2 | 3/2015 | Gall et al. |
| 8,975,816 B2 | 3/2015 | Scheitrum et al. |
| 9,012,866 B2 | 4/2015 | Benna et al. |
| 9,028,384 B2 | 5/2015 | Iikura |
| 9,044,600 B2 | 6/2015 | Balakin |
| 9,056,199 B2 | 6/2015 | Balakin |
| 9,176,468 B2 | 11/2015 | Ueno et al. |
| 9,451,688 B2 | 9/2016 | Jongen |
| 2002/0172317 A1 | 11/2002 | Maksimchuk et al. |
| 2003/0048080 A1 | 3/2003 | Amemiya et al. |
| 2003/0125622 A1 | 7/2003 | Schweikard et al. |
| 2003/0136924 A1 | 7/2003 | Kraft et al. |
| 2003/0146759 A1 | 8/2003 | Bashkirov et al. |
| 2003/0152197 A1 | 8/2003 | Moyers |
| 2003/0163015 A1 | 8/2003 | Yanagisawa et al. |
| 2003/0183779 A1 | 10/2003 | Norimine et al. |
| 2003/0234369 A1 | 12/2003 | Glukhoy |
| 2004/0000650 A1 | 1/2004 | Yanagisawa et al. |
| 2004/0017888 A1 | 1/2004 | Seppi et al. |
| 2004/0056212 A1 | 3/2004 | Yanagisawa et al. |
| 2004/0061077 A1 | 4/2004 | Muramatsu et al. |
| 2004/0061078 A1 | 4/2004 | Muramatsu et al. |
| 2004/0085023 A1 | 5/2004 | Chistyakov |
| 2004/0098445 A1 | 5/2004 | Baumann et al. |
| 2004/0111134 A1 | 6/2004 | Muramatsu et al. |
| 2004/0118081 A1 | 6/2004 | Reimoser et al. |
| 2004/0149934 A1 | 8/2004 | Yanagisawa et al. |
| 2004/0159795 A1 | 8/2004 | Kaercher et al. |
| 2004/0173763 A1 | 9/2004 | Moriyama et al. |
| 2004/0174958 A1 | 9/2004 | Moriyama et al. |
| 2004/0183033 A1 | 9/2004 | Moriyama et al. |
| 2004/0183035 A1 | 9/2004 | Yanagisawa et al. |
| 2004/0200982 A1 | 10/2004 | Moriyama et al. |
| 2004/0200983 A1 | 10/2004 | Fujimaki et al. |
| 2004/0213381 A1 | 10/2004 | Harada |
| 2004/0227104 A1 | 11/2004 | Matsuda et al. |
| 2004/0232356 A1 | 11/2004 | Norimine et al. |
| 2004/0240626 A1 | 12/2004 | Moyers |
| 2005/0058245 A1 | 3/2005 | Ein-Gal |
| 2005/0089141 A1 | 4/2005 | Brown |
| 2005/0161618 A1 | 7/2005 | Pedroni |
| 2005/0184686 A1 | 8/2005 | Caporasco et al. |
| 2005/0228255 A1 | 10/2005 | Saracen et al. |
| 2005/0234327 A1 | 10/2005 | Saracen et al. |
| 2005/0238134 A1 | 10/2005 | Brusasco et al. |
| 2005/0247890 A1 | 11/2005 | Norimine et al. |
| 2006/0017015 A1 | 1/2006 | Sliski |
| 2006/0067468 A1 | 3/2006 | Rietzel |
| 2006/0126792 A1 | 6/2006 | Li |
| 2006/0145088 A1 | 7/2006 | Ma |
| 2006/0170381 A1 | 8/2006 | Amaldi et al. |
| 2006/0175991 A1 | 8/2006 | Fujisawa |
| 2006/0273264 A1* | 12/2006 | Nakayama et al. ....... 250/492.3 |
| 2006/0284562 A1 | 12/2006 | Hruby et al. |
| 2007/0001128 A1 | 1/2007 | Sliski et al. |
| 2007/0013273 A1 | 1/2007 | Albert et al. |
| 2007/0014654 A1 | 1/2007 | Haverfield et al. |
| 2007/0023699 A1 | 2/2007 | Yamashita et al. |
| 2007/0029510 A1 | 2/2007 | Hermann et al. |
| 2007/0051904 A1 | 3/2007 | Kaiser et al. |
| 2007/0061937 A1 | 3/2007 | Curle |
| 2007/0092812 A1 | 4/2007 | Caporasco et al. |
| 2007/0114945 A1 | 5/2007 | Mattaboni et al. |
| 2007/0145916 A1 | 6/2007 | Caporasco et al. |
| 2007/0171015 A1 | 7/2007 | Antaya |
| 2007/0181519 A1 | 8/2007 | Khoshnevis |
| 2007/0252093 A1* | 11/2007 | Fujimaki et al. .......... 250/492.3 |
| 2007/0284548 A1 | 12/2007 | Kaiser et al. |
| 2008/0067452 A1 | 3/2008 | Moriyama et al. |
| 2008/0078937 A1 | 4/2008 | Tsuchiya et al. |
| 2008/0093567 A1 | 4/2008 | Gall |
| 2008/0218102 A1 | 9/2008 | Sliski |
| 2008/0234531 A1 | 9/2008 | Welch et al. |
| 2008/0270517 A1 | 10/2008 | Baumann et al. |
| 2009/0096179 A1 | 4/2009 | Stark et al. |
| 2009/0140671 A1 | 6/2009 | O'Neal et al. |
| 2009/0140672 A1 | 6/2009 | Gall et al. |
| 2009/0200483 A1 | 8/2009 | Gall et al. |
| 2009/0230299 A1 | 9/2009 | Shichi et al. |
| 2009/0236545 A1 | 9/2009 | Timmer |
| 2009/0296885 A1 | 12/2009 | Boeh et al. |
| 2009/0309046 A1 | 12/2009 | Balakin |
| 2009/0314960 A1 | 12/2009 | Balakin |
| 2009/0321665 A1 | 12/2009 | Timmer et al. |
| 2010/0006770 A1 | 1/2010 | Balakin |
| 2010/0027745 A1 | 2/2010 | Balakin |

(56) References Cited

U.S. PATENT DOCUMENTS

| | | | |
|---|---|---|---|
| 2010/0045213 A1 | 2/2010 | Sliski et al. |
| 2010/0046697 A1 | 2/2010 | Balakin |
| 2010/0051833 A1 | 3/2010 | Guertin et al. |
| 2010/0209335 A1 | 8/2010 | Mills |
| 2010/0230617 A1 | 9/2010 | Gall |
| 2010/0308235 A1 | 12/2010 | Sliski |
| 2011/0006212 A1 | 1/2011 | Shchory et al. |
| 2011/0233423 A1 | 9/2011 | Balakin |
| 2011/0240874 A1 | 10/2011 | Iwata |
| 2011/0284760 A1 | 11/2011 | Balakin et al. |
| 2011/0299919 A1 | 12/2011 | Stark |
| 2012/0014501 A1 | 1/2012 | Pelc et al. |
| 2012/0081041 A1 | 4/2012 | Cheung et al. |
| 2012/0217903 A1 | 8/2012 | Tanaka et al. |
| 2013/0053616 A1 | 2/2013 | Gall |
| 2013/0127375 A1 | 5/2013 | Sliski |
| 2013/0131424 A1 | 5/2013 | Sliski |
| 2013/0237425 A1 | 9/2013 | Leigh et al. |
| 2013/0249443 A1 | 9/2013 | Antaya et al. |
| 2014/0028220 A1 | 1/2014 | Bromberg et al. |
| 2014/0042934 A1 | 2/2014 | Tsutsui |
| 2014/0062344 A1 | 3/2014 | Gall et al. |
| 2014/0094643 A1 | 4/2014 | Gall et al. |
| 2014/0097920 A1 | 4/2014 | Goldie et al. |
| 2015/0099917 A1* | 4/2015 | Bula et al. ..................... 600/1 |
| 2015/0099918 A1* | 4/2015 | Takayanagi et al. ............ 600/1 |
| 2015/0161793 A1 | 6/2015 | Takahashi |

FOREIGN PATENT DOCUMENTS

| | | |
|---|---|---|
| CN | 1377521 | 10/2002 |
| CN | 1537657 A | 10/2004 |
| CN | 1537657 A | 10/2004 |
| CN | 1631061 A | 6/2005 |
| CN | 1816243 A | 8/2006 |
| CN | 101361156 A | 2/2009 |
| CN | 101932361 | 12/2010 |
| CN | 101933405 | 12/2010 |
| CN | 101933406 | 12/2010 |
| CN | 102036461 A | 4/2011 |
| CN | 101061759 | 5/2011 |
| CN | 102172106 A | 8/2011 |
| CN | 104244562 | 12/2014 |
| CN | 104812443 | 7/2015 |
| CN | 104812444 | 7/2015 |
| CN | 104822417 | 8/2015 |
| DE | 2753397 | 6/1978 |
| DE | 31 48 100 | 6/1983 |
| DE | 35 30 446 | 8/1984 |
| DE | 41 01 094 C1 | 5/1992 |
| DE | 4411171 | 10/1995 |
| EP | 0044153 A1 | 1/1982 |
| EP | 0 194 728 | 9/1986 |
| EP | 0 277 521 | 8/1988 |
| EP | 0 208 163 | 1/1989 |
| EP | 0 222 786 | 7/1990 |
| EP | 0 221 987 | 1/1991 |
| EP | 0 499 253 | 8/1992 |
| EP | 0276123 | 6/1994 |
| EP | 0 306 966 | 4/1995 |
| EP | 0 388 123 | 5/1995 |
| EP | 0 465 597 | 5/1997 |
| EP | 0 911 064 | 6/1998 |
| EP | 0 864 337 | 9/1998 |
| EP | 0 776 595 | 12/1998 |
| EP | 1 069 809 | 1/2001 |
| EP | 1 153 398 | 4/2001 |
| EP | 1265462 A1 | 12/2002 |
| EP | 1 294 445 | 3/2003 |
| EP | 1 348 465 | 10/2003 |
| EP | 1 358 908 | 11/2003 |
| EP | 1 371 390 | 12/2003 |
| EP | 1 402 923 | 3/2004 |
| EP | 1 430 932 | 6/2004 |
| EP | 1 454 653 | 9/2004 |
| EP | 1 454 654 | 9/2004 |
| EP | 1 454 655 | 9/2004 |
| EP | 1 454 656 | 9/2004 |
| EP | 1 454 657 | 9/2004 |
| EP | 1 477 206 | 11/2004 |
| EP | 1 738 798 | 1/2007 |
| EP | 1790203 A2 | 5/2007 |
| EP | 1 826 778 | 8/2007 |
| EP | 1 949 404 | 7/2008 |
| EP | 2183753 | 7/2008 |
| EP | 2026640 A2 | 2/2009 |
| EP | 2394498 | 2/2010 |
| EP | 2232961 | 9/2010 |
| EP | 2232962 | 9/2010 |
| EP | 2259664 A2 | 12/2010 |
| EP | 2227295 | 5/2011 |
| EP | 1 605 742 | 6/2011 |
| EP | 2363170 | 9/2011 |
| EP | 2363171 | 9/2011 |
| EP | 1826778 | 5/2014 |
| EP | 2814304 | 12/2014 |
| EP | 2900324 | 8/2015 |
| EP | 2900325 | 8/2015 |
| EP | 2900326 | 8/2015 |
| FR | 2 560 421 | 8/1985 |
| FR | 2911843 | 8/2008 |
| GB | 0 957 342 | 5/1964 |
| GB | 1360085 | 7/1974 |
| GB | 1485329 | 9/1977 |
| GB | 2 015 821 | 9/1979 |
| GB | 1583400 | 1/1981 |
| GB | 2 361 523 | 10/2001 |
| JP | 43-23267 | 10/1968 |
| JP | U48-108098 | 12/1973 |
| JP | 57-162527 | 10/1982 |
| JP | 58-141000 | 8/1983 |
| JP | 61-80800 | 4/1986 |
| JP | 61-225798 | 10/1986 |
| JP | 62-150804 | 7/1987 |
| JP | 62-186500 | 8/1987 |
| JP | 10-071213 | 3/1988 |
| JP | 63-149344 | 6/1988 |
| JP | 63-218200 | 9/1988 |
| JP | 63-226899 | 9/1988 |
| JP | 64-89621 | 4/1989 |
| JP | 10247600 | 9/1989 |
| JP | 01-276797 | 11/1989 |
| JP | 01-302700 | 12/1989 |
| JP | 4-94198 | 3/1992 |
| JP | 04-128717 | 4/1992 |
| JP | 04-129768 | 4/1992 |
| JP | 04-273409 | 9/1992 |
| JP | 04-337300 | 11/1992 |
| JP | 05-341352 | 12/1993 |
| JP | 06-233831 | 8/1994 |
| JP | 06-036893 | 10/1994 |
| JP | 07-260939 | 10/1995 |
| JP | 07-263196 | 10/1995 |
| JP | 08-173890 | 7/1996 |
| JP | 08-264298 | 10/1996 |
| JP | 09-162585 | 6/1997 |
| JP | 10270200 | 10/1998 |
| JP | 11-47287 | 2/1999 |
| JP | 11047287 | 2/1999 |
| JP | 11-102800 | 4/1999 |
| JP | 11-243295 | 9/1999 |
| JP | 2000-243309 | 9/2000 |
| JP | 2000-294399 | 10/2000 |
| JP | 2001-6900 | 1/2001 |
| JP | 2001-009050 | 1/2001 |
| JP | 2001-129103 | 5/2001 |
| JP | 2001-346893 | 12/2001 |
| JP | 2002-164686 | 6/2002 |
| JP | A2003-504628 | 2/2003 |
| JP | 2003-517755 | 5/2003 |
| JP | 2004-031115 A | 1/2004 |
| JP | 2004-139944 A | 5/2004 |
| JP | 2005-526578 | 9/2005 |
| JP | 2006-032282 | 2/2006 |

(56) References Cited

FOREIGN PATENT DOCUMENTS

| | | |
|---|---|---|
| JP | 2006233831 A | 9/2006 |
| JP | 2007260939 A | 10/2007 |
| JP | 2007-319439 | 12/2007 |
| JP | 2008-012121 | 1/2008 |
| JP | 05-046928 | 3/2008 |
| JP | 2008-507826 | 3/2008 |
| JP | 2008-089341 | 4/2008 |
| JP | 2008-270039 A | 11/2008 |
| JP | 2009-515671 | 4/2009 |
| JP | 2009-516905 | 4/2009 |
| JP | 2010-204020 | 9/2010 |
| JP | 2010-536130 | 11/2010 |
| JP | 2011-505191 | 2/2011 |
| JP | 2011-505670 | 2/2011 |
| JP | 2011-507151 | 3/2011 |
| JP | 2011-521425 | 7/2011 |
| JP | 2011-210494 A | 10/2011 |
| JP | 2011-224342 | 11/2011 |
| RU | 300137 | 11/1969 |
| RU | 569635 | 8/1977 |
| SU | 300137 | 11/1969 |
| SU | 569 635 | 8/1977 |
| TW | 200930160 | 7/2009 |
| TW | 200934682 | 8/2009 |
| TW | 200939908 | 9/2009 |
| TW | 200940120 | 10/2009 |
| TW | 201422278 | 6/2014 |
| TW | 201422279 | 6/2014 |
| TW | 201424466 | 6/2014 |
| TW | 201429514 | 8/2014 |
| TW | 201433331 | 9/2014 |
| TW | 201434508 | 9/2014 |
| TW | 201438787 | 10/2014 |
| WO | WO 86/07229 | 12/1986 |
| WO | WO 90/12413 | 10/1990 |
| WO | WO 92/03028 | 2/1992 |
| WO | WO 93/02536 | 2/1993 |
| WO | WO 98/17342 | 4/1998 |
| WO | WO 99/39385 | 8/1999 |
| WO | WO 00/40064 | 7/2000 |
| WO | WO-0040064 A2 | 7/2000 |
| WO | WO 00/49624 | 8/2000 |
| WO | WO-0049624 A1 | 8/2000 |
| WO | WO 01/26230 | 4/2001 |
| WO | WO 01/26569 | 4/2001 |
| WO | WO-0126230 A1 | 4/2001 |
| WO | WO-0126569 | 4/2001 |
| WO | WO 02/07817 | 1/2002 |
| WO | WO -0207817 | 1/2002 |
| WO | WO 03/039212 | 5/2003 |
| WO | WO-03039212 A1 | 5/2003 |
| WO | WO-03/092340 A1 | 11/2003 |
| WO | WO 03/092812 | 11/2003 |
| WO | WO-03092812 A1 | 11/2003 |
| WO | WO 2004/026401 | 4/2004 |
| WO | WO 2004/101070 | 11/2004 |
| WO | WO-2005/102453 A1 | 11/2005 |
| WO | WO 2006-012467 | 2/2006 |
| WO | WO 2007/061937 | 5/2007 |
| WO | WO2007/061937 | 5/2007 |
| WO | WO 2007/084701 | 7/2007 |
| WO | WO 2007/130164 | 11/2007 |
| WO | WO 2007/145906 | 12/2007 |
| WO | WO 2008/030911 | 3/2008 |
| WO | WO 2008/081480 | 10/2008 |
| WO | WO 2009/048745 | 4/2009 |
| WO | WO-2009/056165 A1 | 5/2009 |
| WO | 1949404 | 6/2009 |
| WO | WO 2009/070173 | 6/2009 |
| WO | WO 2009/070588 | 6/2009 |
| WO | WO 2009/073480 | 6/2009 |
| WO | WO2009/080080 | 7/2009 |
| WO | WO2010/089574 | 8/2010 |
| WO | WO-2010/149740 A1 | 12/2010 |
| WO | WO2012/044957 | 4/2012 |
| WO | WO-2012/071142 A2 | 5/2012 |
| WO | WO2013/079311 | 6/2013 |
| WO | WO2013/098089 | 7/2013 |
| WO | WO2013/142409 | 9/2013 |
| WO | WO2014/018706 | 1/2014 |
| WO | WO2014/018876 | 1/2014 |
| WO | WO2014/052708 | 4/2014 |
| WO | WO-2014/052709 A2 | 4/2014 |
| WO | WO2014/052716 | 4/2014 |
| WO | WO2014/052718 | 4/2014 |
| WO | WO2014/052719 | 4/2014 |
| WO | WO 2014/052721 | 4/2014 |
| WO | WO2014/052722 | 4/2014 |

OTHER PUBLICATIONS

U.S. Appl. No. 61/676,377, filed Jul. 27, 2012, including the USPTO electronic file for U.S. Appl. No. 61/676,377.
U.S. Appl. No. 13/949,459, filed Jul. 24, 2013, including the USPTO electronic file for U.S. Appl. No. 13/949,459.
U.S. Appl. No. 13/830,792, filed Mar. 14, 2013, including the USPTO electronic file for U.S. Appl. No. 13/830,792.
European Communication from European application No. 13774886.9 issued on Jun. 12, 2015 (2 pages).
Response to European Communication mailed Jun. 12, 2015 in European application No. 13774886.9 filed on Jun. 23, 2015 (17 pages).
"Beam Delivery and Properties," *Journal of the ICRU*, 2007, 7(2):20 pages.
"510(k) Summary: Ion Beam Applications S.A.", FDA, Jul. 12, 2001, 5 pages.
"510(k) Summary: Optivus Proton Beam Therapy System", Jul. 21, 2000, 5 pages.
"An Accelerated Collaboration Meets with Beaming Success," Lawrence Livermore National Laboratory, Apr. 12, 2006, S&TR, Livermore, California, pp. 1-3, http://www.llnl.gov/str/April06/Caporaso.html.
"CPAC Highlights Its Proton Therapy Program at ESTRO Annual Meeting", TomoTherapy Incorporated, Sep. 18, 2008, Madison, Wisconsin, pp. 1-2.
"Indiana's mega-million proton therapy cancer center welcomes its first patients" [online] Press release, Health & Medicine Week, 2004, retrieved from NewsRx.com, Mar. 1, 2004, pp. 119-120.
"LLNL, UC Davis Team Up to Fight Cancer,"Lawrence Livermore National Laboratory, Apr. 28, 2006, SF-06-04-02, Livermore, California, pp. 1-4.
"Patent Assignee Search Paul Scherrer Institute," Library Services at Fish & Richardson P.C., Mar. 20, 2007, 40 pages.
"Patent Prior Art Search for 'Proton Therapy System'," Library Services at Fish & Richardson P.C., Mar. 20, 2007, 46 pages.
"Superconducting Cyclotron Contract" awarded by Paul Scherrer Institute (PSI), Villigen, Switzerland, http://www.accel.de/News/superconducting_cyclotron_contract.htm, Jan. 2009, 1 page.
"The Davis 76-Inch Isochronous Cyclotron", Beam on: Crocker Nuclear Laboratory, University of California, 2009, 1 page.
"The K100 Neutron-therapy Cyclotron," National Superconducting Cyclotron Laboratory at Michigan State University (NSCL), retrieved from: http://www.nscl.msu.edu/tech/accelerators/k100, Feb. 2005, 1 page.
"The K250 Proton therapy Cyclotron," National Superconducting Cyclotron Laboratory at Michigan State University (NSCL), retrieved from: http://www.nscl.msu.edu/tech/accelerators/k250.html, Feb. 2005, 2 pages.
"The K250 Proton-therapy Cyclotron Photo Illustration," National Superconducting Cyclotron Laboratory at Michigan State University (NSCL), retrieved from: http://www.nscl.msu.edu/media/image/experimental-equipment-technology/250.html, Feb. 2005, 1 page.
18th Japan Conference on Radiation and Radioisotopes [Japanese], Nov. 25-27, 1987, 9 pages.
Abrosimov et al., "1000MeV Proton Beam Therapy facility at Petersburg Nuclear Physics Institute Synchrocyclotron," Medical

(56) References Cited

OTHER PUBLICATIONS

Radiology (Moscow) 32, 10 (1987) revised in Journal of Physics, Conference Series 41, 2006, pp. 424-432, Institute of Physics Publishing Limited.
Abrosimov et al., "Neutron Time-of-flight Spectrometer Gneis at the Gatchina 1 GeV Protron Syncrhocyclotron", Mar. 9, 1985 and revised form Jul. 31, 1985, Lemingrad Nuclear Physics Institute, Gatchina, 188350, USSR (15 pages).
Adachi et al., "A 150MeV FFAG Synchrotron with "Return-Yoke Free" Magent," *Proceedings of the 2001 Particle Accelerator Conference*, Chicago, 2001, 3 pages.
Ageyev et al., "The IHEP Accelerating and Storage Complex (UNK) Status Report," *11th International Conference on High-Energy Accelerators*, 1980, pp. 60-70.
Agosteo et al., "Maze Design of a gantry room for proton therapy, "*Nuclear Instruments & Methods in Physics Research*, 1996, Section A, 382, pp. 573-582.
Alexeev et al., "R4 Design of Superconducting Magents for Proton Synchrotrons," *Proceedings of the Fifth International Cryogenic Engineering Conference*, 1974, pp. 531-533.
Allardyce et al., "Performance and Prospects of the Reconstructed CERN 600 MeV Synchrocyclotron," *IEEE Transactions on Nuclear Science USA*, Jun. 1977, ns-24:(3)1631-1633.
Alonso, "Magnetically Scanned Ion Beams for Radiation Therapy," Accelerator & Fusion Research Division, Lawrence Berkeley Laboratory, Berkeley, CA, Oct. 1988, 13 pages.
Amaldi et al., "The Italian project for a hadrontherapy centre" *Nuclear Instruments and Methods in Physics Research A*, 1995, 360, pp. 297-301.
Amaldi, "Overview of the world landscape of Hadrontherapy and the projects of the TERA foundation," Physica Medica, An International journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977, Baveno, pp. 76-85.
Anferov et al., "Status of the Midwest Proton Radiotherapy Institute," Proceedings of the 2003 Particle Accelerator Conference, 2003, pp. 699-701.
Anferov et al., "The Indiana University Midwest Proton Radiation Institute," Proceedings of the 2001 Particle Accelerator Conference, 2001, Chicago, pp. 645-647.
Appun, "Various problems of magnet fabrication for high-energy accelerators." *Journal for All Engineers Interested in the Nuclear Field*, 1967, pp. 10-16 (1967) [Lang.: German], English bibliographic information (http://www.osti.gov/energycitations/product.biblio.jsp?osti_id=4442292).
Arduini et al. "Physical specifications of clinical proton beams from a synchrotron," *Med. Phys*, Jun. 1996, 23 (6): 939-951.
Badano et al., "Proton-Ion Medical Machine Study (PIMMS) Part I," PIMMS, Jan. 1999, 238 pages.
Beeckman et al., "Preliminary design of a reduced cost proton therapy facility using a compact, high field isochronous cyclotron," *Nuclear Instruments and Methods in Physics Research B56/57*, 1991, pp. 1201-1204.
Bellomo et al., "The Superconducting Cyclotron Program at Michigan State University," *Bulletin of the American Physical Society*, Sep. 1980, 25(7):767.
Benedikt and Carli, "Matching to Gantries for Medical Synchrotrons" *IEEE Proceedings of the 1997 Particle Accelerator Conference*, 1997, pp. 1379-1381.
Bieth et al., "A Very Compact Protontherapy Facility Based on an Extensive Use of High Temperature Superconductors (HTS)" *Cyclotrons and their Applications 1998*, Proceedings of the Fifteenth International Conference on Cyclotrons and their Applications, Caen, Jun. 14-19, 1998, pp. 669-672.
Bigham, "Magnetic Trim Rods for Superconducting Cyclotrons," Nuclear Instruments and Methods (North-Holland Publishing Co.), 1975, 141:223-228.
Bimbot, "First Studies of the External Beam from the Orsay S.C. 200 MeV," Institut de Physique Nucleaire, BP 1, Orsay, France, *IEEE*, 1979, pp. 1923-1926.
Blackmore et al., "Operation of the Triumf Proton Therapy Facility," *IEEE Proceedings of the 1997 Particle Accelerator Conference*, May 12-16, 19973:3831-3833.
Bloch, "The Midwest Proton Therapy Center," Application of Accelerators in Research and Industry, Proceedings of the Fourteenth Int'l. Conf., Part Two, Nov. 1996, pp. 1253-1255.
Blosser et al., "Problems and Accomplishments of Superconducting Cyclotrons," Proceedings of the 14$^{th}$ International Conference, Cyclotrons and Their Applications, Oct. 1995, pp. 674-684.
Blosser et al., "Superconducting Cyclotrons", Seventh International Conference on Cyclotrons and their Applications, Aug. 19-22, 1975, pp. 584-594.
Blosser et al., "Progress toward an experiment to study the effect of RF grounding in an internal ion source on axial oscillations of the beam in a cyclotron," National Superconducting Cyclotron Laboratory, Michigan State University, Report MSUCL-760, CP600, Cyclotrons and their Applications 2011, Sixteenth International Conference, 2001, pp. 274-276.
Blosser et al., "A Compact Superconducting Cyclotron for the Production of High Intensity Protons," Proceedings of the 1997 Particle Accelerator Conference, May 12-16, 1997, 1:1054-1056.
Blosser et al., "Advances in Superconducting Cyclotrons at Michigan State University," Proceedings of the 11$^{th}$ International Conference on Cyclotrons and their Applications, Oct. 1986, pp. 157-167, Tokyo.
Blosser et al., "Characteristics of a 400 (Q2/A) MeV Super-Conducting Heavy-Ion Cyclotron," Bulletin of the American Physical Society, Oct. 1974, p. 1026.
Blosser et al., "Medical Accelerator Projects at Michigan State Univ." IEEE Proceedings of the 1989 Particle Accelerator Conference, Mar. 20-23, 1989, 2:742-746.
Blosser et al., "Superconducting Cyclotron for Medical Application", *IEEE Transactions on Magnetics*, Mar. 1989, 25(2): 1746-1754.
Blosser, "Application of Superconductivity in Cyclotron Construction," *Ninth International Conference on Cyclotrons and their Applications*, Sep. 1981, pp. 147-157.
Blosser, "Applications of Superconducting Cyclotrons," Twelfth International Conference on Cyclotrons and Their Applications, May 8-12, 1989, pp. 137-144.
Blosser, "Future Cyclotrons," AIP, *The Sixth International Cyclotron Conference*, 1972, pp. 16-32.
Blosser, "Medical Cyclotrons," *Physics Today*, Special Issue Physical Review Centenary, Oct. 1993, pp. 70-73.
Blosser, "Preliminary Design Study Exploring Building Features Required for a Proton Therapy Facility for the Ontario Cancer Institute", Mar. 1991, MSUCL-760a, 53 pages.
Blosser, "Progress on the Coupled Superconducting Cyclotron Project," *Bulletin of the American Physical Society*, Apr. 1981, 26(4):558.
Blosser, "Synchrocyclotron Improvement Programs," *IEEE Transactions on Nuclear Science USA*, Jun. 1969, 16(3):Part I, pp. 405-414.
Blosser, "The Michigan State University Superconducting Cyclotron Program," Nuclear Science, Apr. 1979, NS-26(2):2040-2047.
Blosser, H., Present and Future Superconducting Cyclotrons, *Bulletin of the American Physical Society*, Feb. 1987, 32(2):171 Particle Accelerator Conference, Washington, D.C.
Blosser, H.G., "Superconducting Cyclotrons at Michigan State University", Nuclear Instruments & Methods in Physics Research, 1987,vol. B 24/25, part II, pp. 752-756.
Botha et al., "A New Multidisciplinary Separated-Sector Cyclotron Facility," *IEEE Transactions on Nuclear Science*, 1977, NS-24(3):1118-1120.
Chichili et al., "Fabrication of Nb3Sn Shell-Type Coils with Pre-Preg Ceramic Insulation," American Institute of Physics Conference Proceedings, AIP USA, No. 711, (XP-002436709, ISSN: 0094-243X), 2004, pp. 450-457.
Chong et al., Radiology Clinic North American 7, 3319, 1969, 27 pages.

(56) References Cited

OTHER PUBLICATIONS

Chu et al., "Performance Specifications for Proton Medical Facility," Lawrence Berkeley Laboratory, University of California, Mar. 1993, 128 pages.
Chu et al., "Instrumentation for Treatment of Cancer Using Proton and Light-ion Beams," Review of Scientific Instruments, Aug. 1993, 64 (8):2055-2122.
Chu, "Instrumentation in Medical Systems," Accelerator and Fusion Research Division, Lawrence Berkeley Laboratory, University of California, Berkeley, CA, May 1995, 9 pages.
Cole et al., "Design and Application of a Proton Therapy Accelerator," Fermi National Accelerator Laboratory, IEEE, 1985, 5 pages.
Collins, et al., "The Indiana University Proton Therapy System," Proceedings of EPAC 2006, Edinburgh, Scotland, 2006, 3 pages.
Conradi et al., "Proposed New Facilities for Proton Therapy at iThemba Labs," *Proceedings of EPAC*, 2002, pp. 560-562.
C/E Source of Ions for Use in Sychro-Cyclotrons Search, Jan. 31, 2005, 9 pages.
Cosgrove et al., "Microdosimetric Studies on the Orsay Proton Synchrocyclotron at 73 and 200 MeV," *Radiation Protection Dosimetry*, 1997, 70(1-4):493-496.
Coupland, "High-field (5 T) pulsed superconducting dipole magnet," *Proceedings of the Institution of Electrical Engineers*, Jul. 1974, 121(7):771-778.
Coutrakon et al. "Proton Synchrotrons for Cancer Therapy," Application of Accelerators in Research and Industry—Sixteenth International Conf., American Institute of Physics, Nov. 1-5, 2000, vol. 576, pp. 861-864.
Coutrakon et al., "A prototype beam delivery system for the proton medical accelerator at Loma Linda," *Medical Physics*, Nov./Dec. 1991, 18(6):1093-1099.
Cuttone, "Applications of a Particle Accelerators in Medical Physics," Istituto Nazionale di Fisica Nucleare-Laboratori Nazionali del Sud, V.S. Sofia, 44 Cantania, Italy, Jan. 2010, 17 pages.
Dahl P, "Superconducting Magnet System," American Institute of Physics, AIP Conference Proceedings, 1987-1988, 2: 1329-1376.
Dialog Search, Jan. 31, 2005, 17 pages.
Dugan et al., "Tevatron Status" IEEE, Particle Accelerator Conference, Accelerator Science & Technology, 1989, pp. 426-430.
Eickhoff et al., "The Proposed Accelerator Facility for Light Ion Cancer Therapy in Heidelberg," Proceedings of the 1999 Particle Accelerator Conference, New York, 1999, pp. 2513-2515.
Enchevich et al., "Minimizing Phase Losses in the 680 MeV Synchrocyclotron by Correcting the Accelerating Voltage Amplitude," *Atomnaya Energiya*, 1969, 26:(3):315-316.
Endo et al., "Compact Proton and Carbon Ion Synchrotrons for Radiation Therapy," Proceedings of EPAC 2002, Paris France, 2002, pp. 2733-2735.
Flanz et al., "Treating Patients with the NPTC Accelerator Based Proton Treatment Facility," Proceedings of the 2003 Particle Accelerator Conference, 2003, pp. 690-693.
Flanz et al., "Large Medical Gantries," Particle Accelerator Conference, Massachusetts General Hospital, 1995, pp. 1-5.
Flanz et al., "Operation of a Cyclotron Based Proton Therapy Facility", Massachusetts General Hospital, Boston, MA 02114, pp. 1-4, retrieved from Internet in 2009.
Flanz et al., "The Northeast Proton Therapy Center at Massachusetts General Hospital," Fifth Workshop on Heavy Charge Particles in Biology and Medicine, GSI, Darmstadt, Aug. 1995, 11 pages.
Flood and Frazier, "The Wide-Band Driven RF System for the Berkeley 88-Inch Cyclotron," American Institute of Physics, Conference Proceedings., No. 9, 1972, 459-466.
Foster and Kashikhin, "Superconducting Superferric Dipole Magent with Cold Iron Core for the VLHC," *IEEE Transactions on Applied Superconductivity*, Mar. 2002, 12(1):111-115.
Friesel et al., "Design and Construction Progress on the IUCF Midwest Proton Radiation Institute," Proceedings of EPAC 2002, 2002, pp. 2736-2738.
Fukumoto et al., "A Proton Therapy Facility Plan" Cyclotrons and their Applications, Proceedings of the 13th International Conference, Vancouver, Canada, Jul. 6-10, 1992, pp. 258-261.
Fukumoto, "Cyclotron Versus Synchrotron for Proton Beam Therapy," KEK Prepr., No. 95-122, Oct. 1995, pp. 533-536.
Goto et al., "Progress on the Sector Magnets for the Riken SRC," American Institute of Physics, CP600, Cyclotrons and Their Applications 2001, Sixteenth International Conference, 2001, pp. 319-323.
Graffman et al., "Design Studies for a 200 MeV Proton Clinic for Radiotherapy," AIP Conference Proceedings: Cyclotrons—1972, 1972, No. 9, pp. 603-615.
Graffman et al., *Acta Radial. Therapy Phys. Biol.* 1970, 9, 1 (1970).
Graffman, et. al. "Proton radiotherapy with the Uppsala cyclotron. Experience and plans" *Strahlentherapie*, 1985, 161(12):764-770.
Hede, "Research Groups Promoting Proton Therapy "Lite,"" Journal of the National Cancer Institute, Dec. 6, 2006, 98(23):1682-1684.
Heinz, "Superconducting Pulsed Magnetic Systems for High-Energy Synchrotrons," *Proceedings of the Fourth International Cryogenic Engineering Conference*, May 24-26, 1972, pp. 55-63.
Hentschel et al., "Plans for the German National Neutron Therapy Centre with a Hospital-Based 70 MeV Proton Cyclotron at University Hospital Essen/Germany," Cyclotrons and their Applications, Proceedings of the Fifteenth International Conference on Cyclotrons and their Applications, Caen, Franco, Jun. 14-19, 1998, pp. 21-23.
Hepburn et al., "Superconducting Cyclotron Neutron Source for Therapy," *International Journal of Radiation Oncology Biology Physics*, vol. 3 complete, 1977, pp. 387-391.
Hirabayashi, "Development of Superconducting Magnets for Beam Lines and Accelerator at KEK," *IEEE Transaction on Magnetics*, Jan. 1981, Mag-17(1):728-731.
Ishibashi and McInturff, "Winding Design Study of Superconducting 10 T Dipoles for a Synchrotron," *IEEE Transactions on Magnetics*, May 1983, MAG-19(3):1364-1367.
Ishibashi and McInturff, "Stress Analysis of Superconducting 10T Magnets for Synchrotron," Proceedings of the Ninth International Cryogenic Engineering Conference, May 11-14, 1982, pp. 513-516.
Jahnke et al., "First Superconducting Prototype Magnets for a Compact Synchrotron Radiation Source in Operation," *IEEE Transactions on Magnetics*, Mar. 1988, 24(2):1230-1232.
Jones and Dershem, "Synchrotron Radiation from Proton in a 20 TEV, 10 TESLA Superconducting Super Collide,r" *Proceedings of the 12th International Conference on High-Energy Accelerator*, Aug. 11-16, 1983, pp. 138-140.
Jones and Mills, "The South African National Accelerator Centre: Particle Therapy and Isotope Production Programmes," *Radiation Physics and Chemistry*, Apr.-Jun. 1998, 51(4-6):571-578.
Jones et al., "Status Report of the NAC Particle Therapy Programme," *Stralentherapie und Onkologie*, vol. 175, Suppl. II, Jun. 1999, pp. 30-32.
Jones, "Progress with the 200 MeV Cyclotron Facility at the National Accelerator Centre," Commission of the European Communities Radiation Protection Proceedings, Fifth Symposium on Neutron Dosimetry, Sep. 17-21, 1984, vol. II, pp. 989-998.
Jones, "Present Status and Future Trends of Heavy Particle Radiotherapy," Cyclotrons and their Applications 1998, Proceedings of the Fifteenth International Conference on Cyclotrons and their Applications, Jun. 14-19, 1998, pp. 13-20.
Jongen et al., "Development of a Low-cost Compact Cyclotron System for Proton Therapy," *National Institute of Radiol. Sci, 1991*, No. 81, pp. 189-200.
Jongen et al., "Progress report on the IBA-SHI small cyclotron for cancer therapy" *Nuclear Instruments and Methods in Physics Research*, Section B, vol. 79, issue 1-4, 1993, pp. 885-889.
Jongen et al., "The proton therapy system for the NPTC: Equipment Description and progress report," *Nuclear Instruments and methods in physics research*, 1996, Section B, 113(1): 522-525.
Jongen et al., "The proton therapy system for MGH's NPTC: equipment description and progress report," *Bulletin du Cancer/Radiotherapie, Proceedings of the meeting of the European Heavy Particle Therapy Group*, 1996, 83(Suppl. 1):219-222.

(56) References Cited

OTHER PUBLICATIONS

Kanai et al., "Three-dimensional Beam Scanning for Proton Therapy," Nuclear Instruments and Methods in Physic Research, Sep. 1, 1983, The Netherlands, 214(23):491-496.
Karlin et al., "Medical Radiology" (Moscow), 1983, 28, 13.
Karlin et al., "The State and Prospects in the Development of the Medical Proton Tract on the Synchrocyclotron in Gatchina," *Med. Radiol.*, Moscow, 28(3):28-32 (Mar. 1983)(German with English Abstract on end of p. 32).
Kats and Druzhinin, "Comparison of Methods for Irradiation Prone Patients," *Atomic Energy*, Feb. 2003, 94(2):120-123.
Kats and Onosovskii, "A Simple, Compact, Flat System for the Irradiation of a Lying Patient with a Proton Beam from Different Directions," *Instruments and Experimental Techniques*, 1996, 39(1): 132-134.
Kats and Onosovskii, "A Planar Magnetooptical System for the Irradiation of a Lying Patient with a Proton Beam from Various Directions," *Instruments and Experimental Techniques*, 1996, 39(1):127-131.
Khoroshkov et al.,"Moscow Hospital-Based Proton Therapy Facility Design," *Am. Journal Clinical Oncology: CCT*, Apr. 1994, 17(2):109-114.
Kim and Blosser, "Optimized Magnet for a 250 MeV Proton Radiotherapy Cyclotron," Cyclotrons and Their Applications 2001, May 2001, *Sixteenth International Conference*, pp. 345-347.
Kim and Yun, "A Light-Ion Superconducting Cyclotron System for Multi-Disciplinary Users," *Journal of the Korean Physical Society*, Sep. 2003, 43(3):325-331.
Kim et al., "Construction of 8T Magnet Test Stand for Cyclotron Studies," *IEEE Transactions on Applied Superconductivity*, Mar. 1993, 3(1):266-268.
Kim et al., "Design Study of a Superconducting Cyclotron for Heavy Ion Therapy," *Cyclotrons and Their Applications 2001, Sixteenth International Conference*, May 13-17, 2001, pp. 324-326.
Kim et al., "Trim Coil System for the Riken Cyclotron Ring Cyclotron," *Proceedings of the 1997 Particle Accelerator Conference, IEEE*, Dec. 1981, vol. 3, pp. 214-235 or 3422-3424, 1998.
Kim, "An Eight Tesla Superconducting Magnet for Cyclotron Studies," Ph.D. Dissertation, Michigan State University, Department of Physics and Astronomy, 1994, 138 pages.
Kimstrand, "Beam Modelling for Treatment Planning of Scanned Proton Beams," Digital Comprehensive Summaries of Uppsala dissertations from the Faculty of Medicine 330, Uppsala Universitet, 2008, 58 pages.
Kishida and Yano, "Beam Transport System for the RIKEN SSC (II)," *Scientific Papers of the Institute of Physical and Chemical Research*, Dec. 1981, 75(4):214-235.
Koehler et al., "Range Modulators for Protons and Heavy Ions," *Nuclear Instruments and Methods*, 1975, vol. 131, pp. 437-440.
Koto and Tsujii, "Future of Particle Therapy," *Japanese Journal of Cancer Clinics*, 2001, 47(1):95-98 [Lang.: Japanese], English abstract (http://sciencelinks.jp/j-east/article/200206/000020020601A0511453.php).
Kraft et al., "Hadrontherapy in Oncology," U. Amaldi and Larrsson, editors Elsevier Science, 1994, 390 pages.
Krevet et al., "Design of a Strongly Curved Superconducting Bending Magnet for a Compact Synchrotron Light Source," *Advances in Cryogenic Engineering*, 1988, vol. 33, pp. 25-32.
Laisne et al., "The Orsay 200 MeV Synchrocyclotron," *IEEE Transactions on Nuclear Science*, Apr. 1979, NS-26(2):1919-1922.
Larsson et al., *Nature*, 1958, 182:1222.
Larsson, "Biomedical Program for the Converted 200-MeV Synchrocyclotron at the Gustaf Werner Institute," *Radiation Research*, 1985, 104:S310-S318.
Lawrence et al., "Heavy particles in acromegaly and Cushing's Disease," in Endocrine and Norendocrine Hormone Producing Tumors (Year Book Medical Chicago, 1973, pp. 29-61.
Lawrence et al., "Successful Treatment of Acromegaly: Metabolic and Clinical Studies in 145 Patients," *The Journal of Clinical Endocrinology and Metabolism*, Aug. 1970, 31(2), 21 pages.
Lawrence et al., "Treatment of Pituitary Tumors," (Excerpta medica, Amsterdam/American Elsevier, New York, 1973, pp. 253-262.
Lawrence, *Cancer*, 1957, 10:795.
Lecroy et al., "Viewing Probe for High Voltage Pulses," *Review of Scientific Instruments USA*, Dec. 1960, 31(12):1354.
Lin et al., "Principles and 10 Year Experience of the Beam Monitor System at the PSI Scanned Proton Therapy Facility", Center for Proton Radiation Therapy, Paul Scherrer Institute, CH-5232, Villigen PSI, Switzerland, 2007, 21 pages.
Linfoot et al., "Acromegaly," in Hormonal Proteins and Peptides, edited by C.H. Li, 1975, pp. 191-246.
Literature Author and Keyword Search, Feb. 14, 2005, 44 pages.
Literature Keyword Search, Jan. 24, 2005, 98 pages.
Literature Search and Keyword Search for Synchrocyclotron, Jan. 25, 2005, 68 pages.
Literature Search by Company Name/Component Source, Jan. 24, 2005, 111 pages.
Literature Search, Jan. 26, 2005, 37 pages.
Livingston et al., "A capillary ion source for the cyclotron," *Review Science Instruments*, Feb. 1939, 10:63.
Mandrillon, "High Energy Medical Accelerators," *EPAC 90, 2nd European Particle Accelerator Conference*, Jun. 12-16, 1990, 2:54-58.
Marchand et al., "IBA Proton Pencil Beam Scanning: an Innovative Solution for Cancer Treatment," Proceedings of EPAC 2000, Vienna, Austria, 3 pages.
Marti et al., "High Intensity Operation of a Superconducting Cyclotron," *Proceedings of the 14the International Conference, Cyclotrons and Their Applications*, Oct. 1995, pp. 45-48 (Oct. 1995).
Martin, "Operational Experience with Superconducting Synchrotron Magnets" *Proceedings of the 1987 IEEE Particle Accelerator Conference*, Mar. 16-19, 1987, vol. 3 of 3:1379-1382.
Meote et al., "ETOILE Hadrontherapy Project, Review of Design Studies" *Proceedings of EPAC 2002*, 2002, pp. 2745-2747.
Miyamoto et al., "Development of the Proton Therapy System," *The Hitachi Hyoron*, 79(10):775-779 (1997) [Lang: Japanese], English abstract (http://www.hitachi.com/rev/1998/revfeb98/rev4706.htm).
Montelius et al., "The Narrow Proton Beam Therapy Unit at the Svedberg Laboratory in Uppsala," *ACTA Oncologica*, 1991, 30:739-745.
Moser et al., "Nonlinear Beam Optics with Real Fields in Compact Storage Rings," Nuclear Instruments & Methods in Physics Research/Section B, B30, Feb. 1988, No. 1, pp. 105-109.
Moyers et al., "A Continuously Variable Thickness Scatterer for Proton Beams Using Self-compensating Dual Linear Wedges" Lorna Linda University Medical Center, Dept. of Radiation Medicine, Lorna Linda, CA, Nov. 2, 1992, 21 pages.
National Cancer Institute Funding (Senate-Sep. 21, 1992) (www.thomas.loc.gov/cgi-bin/query/z?r102:S21SE2-712 (2 pages).
Nicholson, "Applications of Proton Beam Therapy," *Journal of the American Society of Radiologic Technologists*, May/Jun. 1996, 67(5): 439-441.
Nolen et al., "The Integrated Cryogenic—Superconducting Beam Transport System Planned for MSU," *Proceedings of the 12th International Conference on High-Energy Accelerators*, Aug. 1983, pp. 549-551.
Norimine et al., "A Design of a Rotating Gantry with Easy Steering for Proton Therapy," *Proceedings of EPAC 2002*, 2002, pp. 2751-2753.
Ogino, Takashi, "Heavy Charged Particle Radiotherapy-Proton Beam", Division of Radiation Oncology, National Cancer Hospital East, Kashiwa, Japan, Dec. 2003, 7 pages.
Okumura et al., "Overview and Future Prospect of Proton Radiotherapy," *Japanese Journal of Cancer Clinics*, 1997, 43(2):209-214 [Lang.: Japanese].
Okumura et al., "Proton Radiotherapy" *Japanese Journal of Cancer and Chemotherapy*, 1993, 10.20(14):2149-2155[Lang.: Japanese].
Outstanding from Search Reports, "Accelerator of Polarized Portons at Fermilab," 2005, 20 pages.
Paganetti et al., "Proton Beam Radiotherapy—The State of the Art," Springer Verlag, Heidelberg, ISBN 3-540-00321-5, Oct. 2005,36 pages.

(56) References Cited

OTHER PUBLICATIONS

Palmer and Tollestrup, "Superconducting Magnet Technology for Accelerators," *Annual Review of Nuclear and Particle Science*, 1984, vol. 34, pp. 247-284.
Patent Assignee and Keyword Searches for Synchrocyclotron, Jan. 25, 2005, 78 pages.
Pavlovic, "Beam-optics study of the gantry beam delivery system for light-ion cancer therapy," *Nuclear Instruments and Methods in Physics Research*, Section A, Nov. 1997, 399(2):439-454(16).
Pedroni and Enge, "Beam optics design of compact gantry for proton therapy" *Medical & Biological Engineering & Computing*, May 1995, 33(3):271-277.
Pedroni and Jermann, "SGSMP: Bulletin Mar. 2002 Proscan Project, Progress Report on the PROSCAN Project of PSI" [online] retrieved from www.sgsmp.ch/protA23.htm, Mar. 2002, 5 pages.
Pedroni et al., "A Novel Gantry for Proton Therapy at the Paul Scherrer Institute," *Cycloctrons and Their Applications 2001: Sixteenth International Conference. AIP Conference Proceedings*, 2001, 600:13-17.
Pedroni et al., "The 200-MeV proton therapy project at the Paul Scherrer Institute: Conceptual design and practical realization," *Medical Physics*, Jan. 1995, 22(1):37-53.
Pedroni, "Accelerators for Charged Particle Therapy: Performance Criteria from the User Point of View," *Cyclotrons and their Applications, Proceedings of the 13th International Conference*, Jul. 6-10, 1992, pp. 226-233.
Pedroni, "Latest Developments in Proton Therapy" *Proceedings of EPAC 2000*, pp. 240-244, 2000.
Pedroni, "Status of Proton Therapy: results and future trends," Paul Scherrer Institute, Division of Radiation Medicine, 1994, 5 pages.
Peggs et al., "A Survey of Hadron Therapy Accelerator Technologies," Particle Accelerator Conference, Jun. 25-29, 2007, 7 pages.
Potts et al., "MPWP6-Therapy III: Treatment Aids and Techniques" *Medical Physics*, Sep./Oct. 1988, 15(5):798.
Pourrahimi et al., "Powder Metallurgy Processed Nb3Sn(Ta) Wire for High Field NMR magnets," *IEEE Transactions on Applied Superconductivity*, Jun. 1995, 5(2):1603-1606.
Prieels et al., "The IBA State-of-the-Art Proton Therapy System, Performances and Recent Results," *Application of Accelerators in Research and industry—Sixteenth Int'l. Conf., American Institute of Physics*, Nov. 1-5, 2000, 576:857-860.
Rabin et al., "Compact Designs for Comprehensive Proton Beam Clinical Facilities," *Nuclear Instruments & Methods in Physics Research*, Apr. 1989, Section B, vol. 40-41, Part II, pp. 1335-1339.
*Research & Development Magazine*, "Proton Therapy Center Nearing Completion," Aug. 1999, 41(9):2 pages, (www.redmag.com).
Resmini, "Design Characteristics of the K=800 Superconducting Cyclotron at M.S.U.," Cyclotron Laboratory, Michigan State University, East Lansing, Michigan 48824, IEEE Transaction on Nuclear Science, vol. NS-26, No. 2, Apr. 1979, 8 pages.
RetroSearch "Berkeley 88-Inch Cyclotron 'RF' or 'Frequency Control'," Jan. 21, 2005, 36 pages.
RetroSearch "Berkeley 88-Inch Cyclotron," Jan. 24, 2005, 170 pages.
RetroSearch "Bernard Gottschalk, Cyclotron, Beams, Compensated Upstream Modulator, Compensated Scatter," Jan. 21, 2005, 20 pages.
RetroSearch "Cyclotron with 'RF' or 'Frequency Control'," Jan. 21, 2005, 49 pages.
RetroSearch Gottschalk, Bernard, Harvard Cyclotron Wheel, Jan. 21, 2005, 20 pages.
RetroSearch "Loma Linda University Beam Compensation," Jan. 21, 2005, 60 pages.
RetroSearch "Loma Linda University, Beam Compensation Foil Wedge," Jan. 21, 2005, 15 pages.
Revised Patent Keyword Search, Jan. 25, 2005, 88 pages.
Rifuggiato et, al., "Status Report of the LNS Superconducting Cyclotron" *Nukleonika*, 2003, 48: S131-S134, Supplement 2.
Rode, "Tevatron Cryogenic System," *Proceedings of the 12th International Conference on High-energy Accelerators, Fermilab*, Aug. 11-16, 1983, pp. 529-535.
Salzburger et al., "Superconducting Synchrotron Magnets Supraleitende Synchrotronmagnete," Siemens A.G., Erlangen (West Germany). Abteilung Technische Physik, Report No. BMFT-FB-T-75-25, Oct. 1975, p. 147, Journal Announcement: GRAI7619; STAR1415, Subm-Sponsored by Bundesmin. Fuer Forsch. U. Technol. In German; English Summary.
Schillo et al,. "Compact Superconducting 250 MeV Proton Cyclotron for the PSI Proscan Proton Therapy Project," *Cyclotrons and Their Applications 2001, Sixteenth International Conference*, 2001, pp. 37-39.
Schneider et al., "Nevis Synchrocyclotron Conversion Program—RF System," *IEEE Transactions on Nuclear Science USA*, Jun. 1969, ns 16(3): 430-433.
Schneider et al., "Superconducting Cyclotrons," IEEE Transactions on Magnetics, vol. MAG-11, No. 2, Mar. 1975, New York, pp. 443-446.
Schreuder et al., "The Non-orthogonal Fixed Beam Arrangement for the Second Proton Therapy Facility at the National Accelerator Centre," *Application of Accelerators in Research and Industry, American Institute of Physics, Proceedings of the Fifteenth International Conference*, Nov. 1998, Part Two, pp. 963-966.
Schreuder, "Recent Developments in Superconducting Cyclotrons," *Proceedings of the 1995 Particle Accelerator Conference*, May 1-5, 1995, vol. 1, pp. 317-321.
Schubert and Blosser, "Conceptual Design of a High Field Ultra-Compact Cyclotron for Nuclear Physics Research," *Proceedings of the 1997 Particle Accelerator Conference*, May 12-16, 1997, vol. 1, 3 pp. 1060-1062.
Schubert, "Extending the Feasibility Boundary of the Isochronous Cyclotron," Dissertation submitted to Michigan State University, 1997, Abstract http://adsabs.harvard.edu/abs/1998PhDT . . . 147S.
Shelaev et al., "Design Features of a Model Superconducting Synchrotron of JINR," *Proceedings of the 12th International Conference on High-energy Accelerators*, Aug. 11-16, 1983, pp. 416-418.
Shintomi et. Al, "Technology and Materials for the Superconducting Super Collider (SSC) Project," [Lang.: Japanese], The Iron and Steel Institute of Japan 00211575, 78(8): 1305-1313, 1992, http://ci.nii.ac.jp/naid/110001493249/en/.
Sisterson, "World Wide Proton Therapy Experience in 1997," *The American Insitute of Physics, Applications of Accelerators in Research and Industry, Proceedings of the Fifteenth International Conference*, Part Two, Nov. 1998, pp. 959-962.
Sisterson, "Clinical use of proton and ion beams from a world-wide perspective," *Nuclear Instruments and Methods in Physics Research*, Section B, 1989, 40-41:1350-1353.
Slater et al., "Developing a Clinical Proton Accelerator Facility: Consortium-Assisted Technology Transfer," *Conference Record of the 1991 IEEE Particle Accelerator Conference: Accelerator Science and Technology*, vol. 1, May 6-9, 1991, pp. 532-536.
Slater et al., "Development of a Hospital-Based Proton Beam Treatment Center," *International Journal of Radiation Oncology Biology Physics*, Apr. 1988, 14(4):761-775.
Smith et al., "The Northeast Proton Therapy Center at Massachusetts General Hospital" *Journal of Brachytherapy International*, Jan. 1997, pp. 137-139.
Snyder and Marti, "Central region design studies for a proposed 250 MeV proton cyclotron," *Nuclear Instruments and Methods in Physics Research*, Section A, 1995, vol. 355, pp. 618-623.
Soga, "Progress of Particle Therapy in Japan," Application of Accelerators in Research and Industry, American Institute of Physics, Sixteenth International Conference, Nov. 2000, pp. 869-872.
Spiller et al., "The GSI Synchrotron Facility Proposal for Acceleration of High Intensity Ion and Proton Beams" *Proceedings of the 2003 Particle Accelerator Conference*, May 12-16, 2003, vol. 1, pp. 589-591.
Stanford et al., "Method of Temperature Control in Microwave Ferroelectric Measurements," Sperry Microwave Electronics Company, Clearwater, Florida, Sep. 19, 1960, 1 page.

(56) References Cited

OTHER PUBLICATIONS

Tadashi et al., "Large superconducting super collider (SSC) in the planning and materials technology,"78(8):1305-1313, The Iron and Steel Institute of Japan 00211575, Aug. 1992.
Takada, "Conceptual Design of a Proton Rotating Gantry for Cancer Therapy," *Japanese Journal of Medical Physics*, 1995, 15(4):270-284.
Takayama et al., "Compact Cyclotron for Proton Therapy," *Proceedings of the 8th Symposium on Accelerator Science and Technology*, Japan, Nov. 25-27, 1991, pp. 380-382.
Teng, "The Fermilab Tevatron," Coral Gables 1981, Proceedings, Gauge Theories, Massive Neutrinos, and Proton Decay, 1981, pp. 43-62.
The Journal of Practical Pharmacy, 1995, 46(1):97-103 [Japanese].
Tilly, et al., "Development and verification of the pulsed scanned proton beam at The Svedberg Laboratory in Uppsala", Physics in Medicine and Biology, Phys. Med. Biol. 52, pp. 2741-2454, 2007.
Tobias et al., *Cancer Research*,1958, 18, 121 (1958).
Tom, "The Use of Compact Cyclotrons for Producing Fast Neutrons for Therapy in a Rotatable Isocentric Gantry," *IEEE Transaction on Nuclear Science*, Apr. 1979, 26(2):2294-2298.
Toyoda, "Proton Therapy System", Sumitomo Heavy Industries, Ltd., 2000, 5 pages.
Trinks et. al., "The Tritron: A Superconducting Separated-Orbit Cyclotron," *Nuclear Instruments and Methods in Physics Research*, Section A, 1986, vol. 244, pp. 273-282.
Tsuji, "The Future and Progress of Proton Beam Radiotherapy," *Journal of Japanese Society for Therapeutic Radiology and Oncology*, 1994, 6(2):63-76.
UC Davis School of Medicine, "Unlikely Partners Turn Military Defense into Cancer Offense", Current Issue Summer 2008, Sacramento, California, pp. 1-2.
Umegaki et al., "Development of an Advanced Proton Beam Therapy System for Cancer Treatment" *Hitachi Hyoron*, 2003, 85(9):605-608 [Lang.: Japanese], English abstract, http://www.hitachi.com/ICSFiles/afieldfile/2004/06/01/r2003_04_104.pdf or http://wwvv.hitachi.com/rev/archive/2003/2005649_12606.html (full text) [Hitachi, 52(4), Dec. 2003].
Umezawa et al., "Beam Commissioning of the new Proton Therapy System for University of Tsukuba," *Proceedings of the 2001 Particle Accelerator Conference*, vol. 1, Jun. 18-22, 2001, pp. 648-650.
van Steenbergen, "Superconducting Synchroton Development at BNL," *Proceedings of the 8th International Conference on High-Energy Accelerators CERN 1971*, 1971, pp. 196-198.
van Steenbergen, "The CMS, a Cold Magnet Synchrotron to Upgrade the Proton Energy Range of the BNL Facility," *IEEE Transactions on Nuclear Science*, Jun. 1971, 18(3):694-698.
Vandeplassche et al., "235 MeV Cyclotron for MGH's Northeast Proton Therapy Center (NPTC): Present Status," EPAC 96, *Fifth European Partical Accelerator Conference*, vol. 3, Jun. 10-14, 1996, pp. 2650-2652.
Vorobiev et al., "Concepts of a Compact Achromatic Proton Gantry with a Wide Scanning Field", Nuclear Instruments and Methods in Physics Research, Section A., 1998, 406(2):307-310.
Vrenken et al., "A Design of a Compact Gantry for Proton Therapy with 2D-Scanning," *Nuclear Instruments and Methods in Physics Research*, Section A, 1999, 426(2):618-624.
Wikipedia, "Cyclotron" http://en.wikipedia.org/wiki/Cyclotron (originally visited Oct. 6, 2005, revisited Jan. 28, 2009), 7pages.
Wikipedia, "Synchrotron" http://en.wikipedia.org/wiki/Synchrotron (originally visited Oct. 6, 2005, revisited Jan. 28, 2009), 7 pages.
Worldwide Patent Assignee Search, Jan. 24, 2005, 224 pages.
Worldwide Patent Keyword Search, Jan. 24, 2005, 94 pages.
Wu, "Conceptual Design and Orbit Dynamics in a 250 MeV Superconducting Synchrocyclotron," Ph.D. Dissertation, Michigan State University, Department of Physics and Astronomy, 1990, 172 pages.
York et al., "Present Status and Future Possibilities at NSCL-MSU," EPAC 94, Fourth European Particle Accelerator Conference, pp. 554-556, Jun. 1994.

York et al., "The NSCL Coupled Cyclotron Project—Overview and Status,"*Proceedings of the Fifteenth International Conference on Cyclotrons and their Applications*, Jun. 1998, pp. 687-691.
Yudelev et al., "Hospital Based Superconducting Cyclotron for Neutron Therapy: Medical Physics Perspective," *Cyclotrons and their applications 2001, 16th International Conference. American Institute of Physics Conference Proceedings*, vol. 600, May 13-17, 2001, pp. 40-43.
Zherbin et al., "Proton Beam Therapy at the Leningrad Synchrocyclotron (Clinicomethodological Aspects and Therapeutic Results)", Aug. 1987, 32(8):17-22, (German with English abstract on pp. 21-22).
International Search Report and Written Opinion from PCT application No. PCT/US2013/062119 mailed on Nov. 26, 2013 (9 pages).
International Preliminary Report on Patentability from PCT application No. PCT/US2013/062119 mailed on Apr. 9, 2015 (7 pages).
Japanese office action with English translation issued in corresponding Japanese application 2015-534728 on Mar. 28, 2016 (11 pages). NOTE: The Japanese Office Action only in Japanese language was filed on Apr. 11, 2016 with the USPTO.
International Preliminary Report on Patentability from PCT application No. PCT/US2013/062137 mailed on Mar. 31, 2015 (9 pages).
European Communication issued in corresponding European application No. 13783422.2 on Jun. 12, 2015 (2 pages).
Response to European Communication issued in corresponding European application No. 13783422.2 on Jun. 12, 2015, filed on Dec. 8, 2015 (19 pages).
Japanese office action issued in corresponding Japanese application 2015-534733 on Mar. 18, 2016 (6 pages). NOTE: English translation has not been received from Associate.
Verster, N.F.,: "Regenerative Beam Extraction from the 150-MeV Synchrocyclotron at the Laboratoire Curie", Proceedings of Sector-Focused Cyclotrons 1959, 1959, pp. 224-229 (6 pages).
Elo, Don, et al., "Mechanical Design of Regenerative Deflector for the Berkeley 88-Inch Cyclotron", Proceedings of the International Conference on Isochronous Cyclotrons, Gatlinburg, Tennessee, Aug. 1966 (7 pages).
Rainwater, James, "Status of the Nevis Synchrocyclotron Modification", AIP Conference Proceedings No. 9, 1972 (14 pages).
Cohen, R. et al., "Nevis Synchrocyclotron Conversion Project", IEEE Transactions on Nuclear Science, IEEE Service Center, New York, NY, US, vol. 16, No. 3, Jun. 1, 1969, pp. 421-425, XP011351570, ISSN: 0018-9499, DOI: 10.1109/TNS.1969.4325264 abstract; figures 1-4a Chap. 1, p. 421-422; chap. 11 from p. 423, col. 2 to p. 425, col. 1. (5 pages).
Ormrod, J.H., et al., "The Chalk-River Superconducting Cyclotron", Proceedings of 8th International Conference on Cyclotrons and their applications '79, 1979 (6 pages).
Ormrod, J.H., et al, "Status of the Chalk-River Superconducting Heavy-Ion Cyclotron", Proceedings of 9th International Conference on Cyclotrons and their Applications '81, 1981 (9 pages).
Dey, M.K., et al., "Coil Centering for the Kolkata Superconducting Cyclotron Magnet", Cyclotrons and their applications, Proceedings, 18th International Conference, Cyclotrons 2007, Giardini Naxo, Italy, Oct. 1-5, 2007 (3 pages).
European Communication issued in corresponding European application No. 13774886.9 on Jun. 1, 2015, with amended claims filed on Jun. 1, 2015 (20 pages).
Response to European Communication issued in corresponding European application No. 13774886.9 on Jun. 12, 2015, filed on Dec. 9, 2015 (26 pages).
Japanese office action issued in corresponding Japanese application 2015-534728 on Mar. 28, 2016 (6 pages) Note: English translation has not been received from Associate.
International Preliminary Report on Patentability from PCT application No. PCT/US2013/062119 mailed on Mar. 31, 2015 (7 pages).
First Office Action (Chinese translation) for CN201380062115.7, 7 pages (Dec. 12, 2016).
First Office Action (English translation) for CN201380062115.7, 9 pages (Dec. 12, 2016).
"The Cutting Edge of Cancer Therapy Using Proton Beams," The Journal of Practical Pharmacy, vol. 46, No. 1, 10 pages (1995). [Japanese] (English Abstract).

(56) References Cited

OTHER PUBLICATIONS

Amaldi, Cyclinacs, Novel Fast-Cycling Accelerators for Hadrontherapy, 2007, Cyclotrons and Their Applications, 18th International Conference, pp. 166-168.
Blom, Mikael, Development of a Scanning System for Proton Therapy in Uppsala, Department of Radiation Sciences, Uppsala University, 2450-2451.
Blosser, H. G. "Compact Superconducting Synchrocyclotron Systems for Proton Therapy," Nuclear Instruments & Methods in Physics Research, Section B40-41, Part II, pp. 1326-1330 (1989).
Canadian Office action from Canadian application No. 2,629,333 issued Aug. 30, 2010 (5 pages).
Canadian Office action from Canadian application No. 2,629,333 issued May 11, 2011 (2 pages).
Canadian office action from Canadian application No. 2574122 dated Aug. 14, 2014 (6 pages).
Chinese Office action from Chinese application No. 200680051421.0 issued Aug. 22, 2011 (4 pages).
Chinese Office action from Chinese application No. 200680051421.0 issued Dec. 25, 2009 (8 pages).
Chinese Office action from Chinese application No. 200680051421.0 issued Mar. 21, 2011 (6 pages).
Chinese Office Action from Chinese Application No. 200780102281.X issued Dec. 7, 2011 with English translation (23 pages).
Chinese Office action from Chinese application No. 200880125832.9, mailed Jun. 5, 2012 (5 pages).
Chinese Office action from Chinese application No. 200880125832.9, mailed Jun. 5, 2012. English Translation will follow upon receipt (4 pages).
Chinese Office action from Chinese application No. 200880125832.9, mailed Sep. 22, 2011 (11 pages).
Chinese Office action from Chinese application No. 200880125918.1, mailed Sep. 15, 2011 (17 pages).
Chinese Office action with English translation from Chinese Application No. 200880125832.9, issued Mar. 4, 2013 (8 pages).
European Communication from European application No. 06838033.6 mailed Apr. 20, 2010 (7 pages).
European Communication from European application No. 07868958.5, mailed Nov. 26, 2010 (50 pages).
European Communication from European application No. 11/65422.4 mailed Sep. 2, 2011 (5 pages).
European Communication from European application No. 11/65423.2 mailed Sep. 2, 2011 (5 pages).
European Communication issued in European Application No. 05776532.3 mailed Jun. 10, 2011 (10 pages).
European Patent Office communication for application No. 06838033.6, patent No. 1949404, mailed Aug. 5, 2009 (1 page).
European Patent Office communication from European application No. 07868958.5, mailed Jul. 16, 2010 (2 pages).
European Patent Office communication from European application No. 08855024.9, mailed Jul. 30, 2010 (2 pages).
European Search Report from application No. EP 06838033.6 (PCT/US2006/044853) mailed May 11, 2009 (7 pages).
European Search Report from European Application No. 10175751.6 mailed Nov. 18, 2010 (8 pages).
European Search Report from European application No. 11165422.4 mailed Aug. 8, 2011 (118 pages).
European Search Report from European application No. 11165423.2 mailed Aug. 8, 2011 (118 pages).
European Search Report issued in European Application No. 08856764.9 on Jun. 4, 2014 (3 pages).
Extended Search Report for EP10175727, 7 pages (Dec. 19, 2015).
Favale, A. et al., Pre-conceptual Design of a Rapid Cycling Medical Synchrotron, The AES/BNL collaboration, 45 pages (Oct. 27, 1999).
File History for U.S. Appl. No. 14/039,307 as of Jan. 13, 2017, 343 pages.
File history of U.S. Appl. No. 10/949,734 (now U.S. Pat. No. 7,208,748) (downloaded Mar. 14, 2017).
File history of U.S. Appl. No. 11/187,633 (downloaded Mar. 14, 2017).
File history of U.S. Appl. No. 11/371,622 (now U.S. Pat. No. 7,402,963) (downloaded Mar. 14, 2017).
File history of U.S. Appl. No. 11/463,403 (now U.S. Pat. No. 7,656,258) (downloaded Mar. 14, 2017).
File history of U.S. Appl. No. 11/517,490 (now U.S. Pat. No. 7,701,677) (downloaded Mar. 14, 2017).
File history of U.S. Appl. No. 11/601,056 (now U.S. Pat. No. 7,728,311) (downloaded Mar. 14, 2017).
File history of U.S. Appl. No. 11/624,769 (now U.S. Pat. No. 7,541,905) (downloaded Mar. 14, 2017).
File history of U.S. Appl. No. 11/724,055 (now U.S. Pat. No. 7,718,982) (downloaded Mar. 14, 2017).
File history of U.S. Appl. No. 11/870,961 (now U.S. Pat. No. 8,003,964) (downloaded Mar. 14, 2017).
File history of U.S. Appl. No. 11/948,662 (now U.S. Pat. No. 8581523) (downloaded Mar. 14, 2017).
File history of U.S. Appl. No. 12/275,103 (now U.S. Pat. No. 8,344,340) (downloaded Mar. 14, 2017).
File history of U.S. Appl. No. 60/590,088 (downloaded Mar. 14, 2017).
File history of U.S. Appl. No. 60/850,565 (downloaded Mar. 14, 2017).
File history of U.S. Appl. No. 60/991,454 (downloaded Mar. 14, 2017).
First Office Action for 201380062111.9, 46 pages (Jun. 1, 2016).
Fish & Richardson P.C., Response to Non Final Office action mailed Aug. 20, 2010 in U.S. Appl. No. 11/948,359, filed Feb. 22, 2011 (17 pages).
Flanz, et al., "Scanning Beam Technologies", PTCOG 2008, 28 pages.
Gordon, M.M. et. al., "Design Study for a Compact 200 MeV Cyclotron," AIP Conference Proceedings Sixth International Cyclotron Conference, No. 9, pp. 78-86 (1972).
Gordon, M.M., "Extraction Studies for a 250 MeV Superconducting Synchrocyclotron," Proceedings of the 1987 IEEE Particle Accelerator Conference: Accelerator Engineering and Technology, pp. 1255-1257 (1987).
Grözinger, Sven Oliver, Volume Conformal Irradiation of Moving Target Volumes with Scanned Ion Beams, Vom Fachbereich Physik der Technischen Universitat Darmstadt, 110 pages (2004).
International Preliminary Report on Patentability for PCT application No. PCT/US2007/001506 mailed Jul. 5, 2007 (15 pages).
International Preliminary Report on Patentability from PCT application No. PCT/US2007/086109, mailed Jun. 10, 2010 (6 pages).
International Preliminary Report on Patentability from PCT application No. PCT/US2008/084695, mailed Jun. 10, 2010 (9 pages).
International Preliminary Report on Patentability from PCT application No. PCT/US2008/084699, mailed Jun. 10, 2010 (6 pages).
International Preliminary Report on Patentability issued in PCT application PCT/US2013/062103 on Apr. 9, 2015 (11 pages).
International Search Report and Written Opinion for PCT application No. PCT/US2007/001506 mailed Jul. 5, 2007, Publication No. WO 2007/084701, Published Jul. 26, 2007 (14 pages).
International Search Report and Written Opinion for PCT application No. PCT/US2008/084695 mailed Jan. 26, 2009 (9 pages).
International Search Report and Written Opinion from PCT application No. PCT/US2013/062103 mailed Apr. 14, 2014 (13 pages).
International Search Report and Written Opinion in International Application No. PCT/US2008/077513, dated Oct. 1, 2009, 73 pages.
International Search Report and Written Opinion in International Application No. PCT/US2008/084699, dated Feb. 4, 2009, 6 pages.
International Search Report dated Aug. 26, 2008 in PCT application No. PCT/US2007/086109 (3 pages).
International Search Report for PCT/US2007/001628 mailed Feb. 18, 2008 (4 pages).
Kanazawa, M. et al., Beam Control in the Spot Scanning Irradiation, Proceedings of the Second Asian Particle Accelerator Conference, China; 846-848 (2001).

(56) References Cited

OTHER PUBLICATIONS

Kawachi, K. et al., Three Dimensional Spot Beam Scanning Method for Proton Conformation Radiation Therapy, Acta Radiologica, Supplementum 364, 10 pages (1982).
Lorin, S. et al., Development of a compact proton scanning system in Uppsala with a moveable second magnet, Phys. Med. Biol, 45:1151-1163 (2000).
Murphy, M. and Lin, P., Intra-fraction dose delivery timing during stereotactic radiotherapy can influence the radiobiological effect, Med. Phys., 34(2):481-484 (2007).
Non Final Office Action from U.S. Appl. No. 12/275,103 mailed Feb. 1, 2011 (6 pages).
Non Final Office Action from U.S. Appl. No. 12/618,297 mailed May 13, 2011 (57 pages).
Office Action and response history of U.S. Appl. No. 11/601,056 to Aug. 24, 2009.
Office Action and response history of U.S. Appl. No. 11/601,056 to Mar. 24, 2009.
Office Action and response history of U.S. Appl. No. 11/601,056 up to Jan. 14, 2010.
Office Action for JP2015-534721, 14 pages (Feb. 3, 2016) (in both Japanese and English).
Office action from Canadian Application No. 2,574,122 mailed Nov. 14, 2012 (6 pages).
Office action from U.S. Appl. No. 11/948,662, mailed Oct. 14, 2011 (5 pages).
Office Action with English translation from Japanese Application No. 2007-522777 mailed Oct. 4, 2011 (15 pages).
Office action with English translation from Taiwanese application No. 097144546 issued Oct. 25, 2013 (27 pages).
Office action with English Translation issued in Chinese Application No. 201010581384.2 on Nov. 10, 2011 (19 pages).
Pardo, J. et al., Simulation of the performance of the CNAO facility's Beam Delivery System, PTCOG 46, Zibo, China, 17 pages (2007).
Pedroni, E. et al., Cancer Therapy with 200 MEV Protons at PSI. Development of a Fast Beam Scanning Method and Future Plans for a Hospital Based Facility, pp. 277-279 (1990).
Response to Chinese Office action of Jan. 25, 2010 in Chinese application No. 200680051421.0, filed Jun. 24, 2010 (34 pages).
Response to European Communication of Apr. 20, 2010, from European application No. 06838033.6, filed Nov. 2, 2010 (13 pages).
Response to examination search report filed in European Application No. 05776532.3 on Dec. 20, 2011 (14 pages).
Response to Non Final Office Action issued Feb. 1, 2011 in U.S. Appl. No. 12/275,103, filed May 2, 2011 (13 pages).
Response with English translation to Chinese Office action filed in Chinese Application No. 200880125832.9 on Dec. 16, 2013 (12 pages).
Response with English translation to Chinese Office Action from Chinese application No. 200880125832.9 issued Sep. 22, 2011, filed on Apr. 9, 2012 (23 pages).
Response with English translation to Japanese Office action filed Mar. 1, 2012 in Japanese Application No. 2007-522777 (14 pages).
Response with English translation to office action dated Oct. 25, 2013 in Taiwanese Application No. 097144546, filed on Mar. 28, 2014 (34 pages).
Second Office Action (English) for JP2015-534721, 5 pages (Dec. 26, 2016).
Second Office Action (Japanese) for JP2015-534721, 5 pages (Dec. 26, 2016).
Shinji Sato et al., "Dynamic Intensity Control System with RF-knockout Slow-Extraction in the HIMAC Synchrotron-" Nuclear Instruments and Methods in Physics Research A 574, 2007, pp. 226-231.
Single Room Proton Therapy Facility, ACCEL, Oct. 2006, 1 page.
Source Search "Cites of U.S. and Foreign Patents/Published applications in the name of Mitsubishi Denki Kabushiki Kaisha and Containing the Keywords (Proton and Synchrocyclotron)," Jan. 2005, 8 pages.
Takada, Y. "A Review of Rotating Gantries for Heavy Charged Particle Therapy," Symposium of Research Center for Charged Particle Therapy on Fundamental Development of the Charged Particle Therapy, Chiba (Japan), Nov., 1 page, 2001.
Timmer, "The ACCEL Single Room Proton Therapy Facility" ACCEL Instruments GmbH, PTCOG 45, Oct. 2006, Houston, Texas, 18 pages.
Tsuji, H., "Cancer Therapy Using Proton Beams: the Newest State of Affairs and Future Prospects," Isotope News, No. 9, pp. 2-7 (1992). (English Abstract).
USPTO Non Final Office Action in U.S. Appl. No. 11/948,359, dated Aug. 20, 2010 (12 pages).
U.S. Appl. No. 60/738,404, filed Nov. 18, 2005, including application as filed.
UC Davis "Crocker Nuclear Laboratory Houses a Medium-Energy Particle Accelerator," Crocker Nuclear Laboratory, University of California (2009).
Uli Weber et al., "Depth Scanning for a Conformal Ion Beam Treatment of Deep Seated Tumours-" Physics in Medicine and Biology IOP Publishing UK, vol. 45, No. 12, Dec. 2000, pp. 3627-3641.
Voluntary amendment filed Apr. 18, 2011 in Chinese application No. CN200780102281.X, including English translation of claim amendments (10 pages).
Voluntary amendment filed in Canadian Application No. 2,574,122 on Jul. 26, 2010 (16 pages).
Voluntary amendment filed in Canadian Application No. 2,574,122 on Nov. 5, 2010 (15 pages).
Voluntary amendment filed in Canadian Application No. 2707075 on Oct. 13, 2013 (8 pages).
Voluntary Amendment filed in Canadian Application No. 2707075 on Oct. 18, 2013 (8 pages).
Written Opinion dated Aug. 26, 2008 in PCT application No. PCT/US2007/086109 (5 pages).
Written Opinion for PCT/US2007/001628, mailed Feb. 18, 2008 (11 pages).

\* cited by examiner

CONTROL SYSTEM FOR A PARTICLE ACCELERATOR

CROSS-REFERENCE TO RELATED APPLICATION

Priority is hereby claimed to U.S. Provisional Application No. 61/707,645, which was filed on Sep. 28, 2012. The contents of U.S. Provisional Application No. 61/707,645 are hereby incorporated by reference into this disclosure.

TECHNICAL FIELD

This disclosure relates generally to a control system for a particle accelerator.

BACKGROUND

Particle therapy systems use a particle accelerator to generate a particle beam for treating afflictions, such as tumors. A control system manages the behavior of the particle accelerator to ensure that it operates as desired.

SUMMARY

An example particle therapy system may include a particle accelerator to output a particle beam, where the particle accelerator includes: a particle source to provide pulses of ionized plasma to a cavity, where each pulse of the particle source has a pulse width corresponding to a duration of operation of the particle source to produce the corresponding pulse, and where the particle beam is based on the pulses of ionized plasma; and a modulator wheel having different thicknesses, where each thickness extends across a different circumferential length of the modulator wheel, and where the modulator wheel is arranged to receive a precursor to the particle beam and is configured to create a spread-out Bragg peak for the particle beam. The example particle therapy system also includes one or more first input/output (I/O) modules operable at a first speed, where the one or more first I/O modules are configured to send machine instructions to one or more motor controllers, at least one of which is for controlling the modulator wheel; and one or more second I/O modules operable at a second speed that is greater than the first speed, at least one of which is configured to send machine instructions to the particle source so that pulse widths of the particle source vary with rotational positions of the modulator wheel. The example particle therapy system may also include one or more of the following features:

The example particle therapy system may include: a therapy control computer programmed to receive prescription information from a hospital, to translate the prescription information to machine information, and to send treatment records to the hospital; and a master control computer having a real-time operating system, where the master control computer is programmed to receive machine information from the therapy control computer, to translate the machine information into machine instructions, and to send the machine instructions to one or more of the first I/O modules and the second I/O modules.

The example particle therapy system may include an optical fiber over which is monitored a rotational speed and position of the modulator wheel. A speed of the first I/O modules may be on the order of milliseconds and a speed of the second I/O modules may be on the order of one or more hundreds of nanoseconds.

The first I/O modules may be programmable logic controllers (PLC). At least one of the PLCs may be programmed to send machine instructions to motor controllers for controlling a field shaping wheel system for shaping the particle beam prior to output. At least one of the PLCs may be programmed to send machine instructions to a motor controller for controlling a scattering system for collimating the particle beam prior to output.

The example particle therapy system may include a radio frequency (RF) system to sweep RF frequencies through the cavity to extract particles from a plasma column produced by the particle source, where the RF system includes a rotating capacitor. At least one of the PLCs may be programmed to send machine instructions to a motor controller that controls the rotating capacitor. Two or more of the PLCs may be configured to communicate with one another.

The example particle therapy system may include a rotatable gantry on which the particle accelerator is mounted. At least one of the PLCs may be programmed to send machine instructions to a motor controller that controls the rotatable gantry.

The second I/O modules may be field-programmable gate arrays (FPGA). The example particle therapy system may include a circuit board including a microprocessor. At least one of the FPGAs may be on the circuit board and in communication with the microprocessor. The microprocessor may be programmed to communicate with a control computer.

The example particle therapy system may include a radio frequency (RF) system to sweep RF frequencies through the cavity to extract particles from a plasma column produced by the particle source. At least one of the FPGAs may be an RF control module. The RF control module may be configured to receive information about a rotation of the modulator wheel and, based thereon, to coordinate operational aspects of the particle source and the RF system. Coordinating operational aspects of the particle source and the RF system may include turning the particle source on or off based on a rotational position of the modulator wheel, and turning the RF system on or off based on a rotational position of the modulator wheel. The RF control module may be configured to send machine instruction to the particle source to turn-on when an RF voltage is at a certain frequency and to turn-off when the RF voltage is at a certain frequency. Coordinating operational aspects of the particle source may include specifying pulse widths during turn-on times of the particle source.

An example particle therapy system may include a particle accelerator to output a particle beam included of pulses and a depth modulator that is in a path of the particle beam. The depth modulator has a variable thickness and is movable so that the particle beam impacts different thicknesses of the depth modulator at different times. The particle therapy system is configured to control numbers of pulses that impact the different thicknesses of the depth modulator. The example particle therapy system may include one or more of the following features, either alone or in combination.

Movement of the depth modulator may be controllable so that different numbers of pulses impact at least two different thicknesses of the depth modulator. The particle therapy system may include a control system to provide control signals and a motor to control movement of the depth modulator in response to the control signals, where the movement is rotation that is controllable by the control signals.

Output of pulses from the accelerator may be controlled so that different numbers of pulses impact at least two different thicknesses of the depth modulator. The particle accelerator may include a particle source configured to generate a plasma stream from which the pulses are extracted, where the plasma stream is generated in response to voltage applied to ionized gas, and the voltage is controllable to turn the particle source on and off to control the number of pulses that impact the at least two different thicknesses. The particle accelerator may include a particle source configured to generate a plasma stream from which the pulses are extracted; and a radio frequency (RF) source to sweep frequencies and thereby extract one or more pulses from the plasma stream at each frequency sweep. The RF source may be controllable to control numbers of pulses that impact different thicknesses of the depth modulator. The RF source may be controllable to skip one or more frequency sweeps. The particle therapy system may be configured by including one or more structures to deflect pulses so as to control numbers of pulses that impact different thicknesses of the depth modulator.

An example particle therapy system may include a particle accelerator to output a particle beam, where the accelerator includes: a particle source to provide pulses of ionized plasma to a cavity, where each pulse of the particle source has a pulse width corresponding to a duration of operation of the particle source to produce the corresponding pulse, and where the particle beam is based on the pulses of ionized plasma; and a modulator wheel having different thicknesses, where each thickness extends across a different circumferential length of the modulator wheel, and where the modulator wheel is arranged to receive a precursor to the particle beam and is configured to create a spread-out Bragg peak for the particle beam. The particle therapy system may be configured so that pulse widths of the particle source vary with rotational positions of the modulator wheel.

Two or more of the features described in this disclosure, including those described in this summary section, may be combined to form implementations not specifically described herein.

Control of the various systems described herein, or portions thereof, may be implemented via a computer program product that includes instructions that are stored on one or more non-transitory machine-readable storage media, and that are executable on one or more processing devices. The systems described herein, or portions thereof, may be implemented as an apparatus, method, or electronic system that may include one or more processing devices and memory to store executable instructions to implement control of the stated functions.

The details of one or more implementations are set forth in the accompanying drawings and the description below. Other features, objects, and advantages will be apparent from the description and drawings, and from the claims.

DESCRIPTION OF THE DRAWINGS

Like reference symbols in the various drawings indicate like elements.

DETAILED DESCRIPTION

Overview

Figure 1:
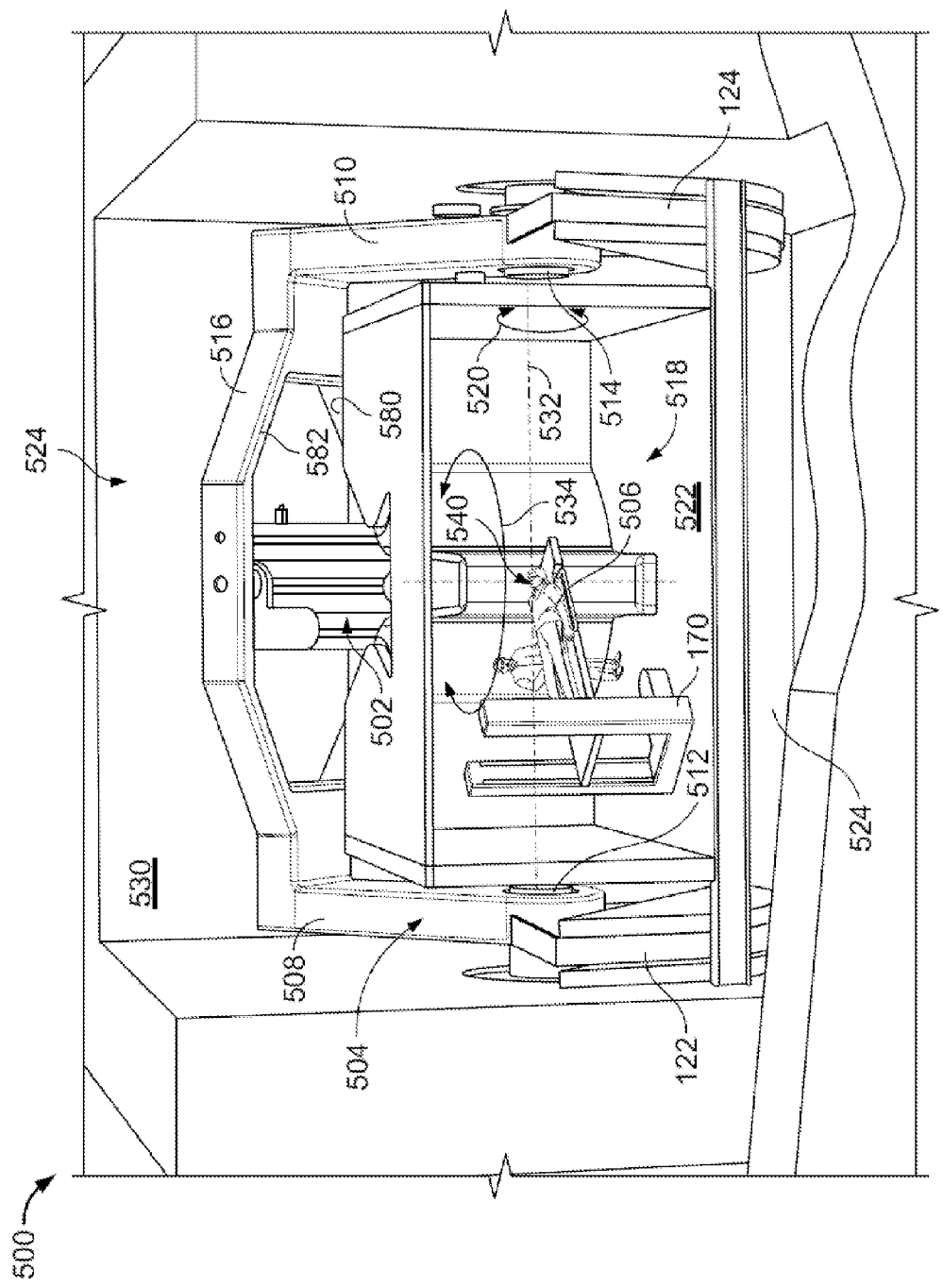
FIG. 1 is a perspective view of an example particle therapy system.
Figure 2:
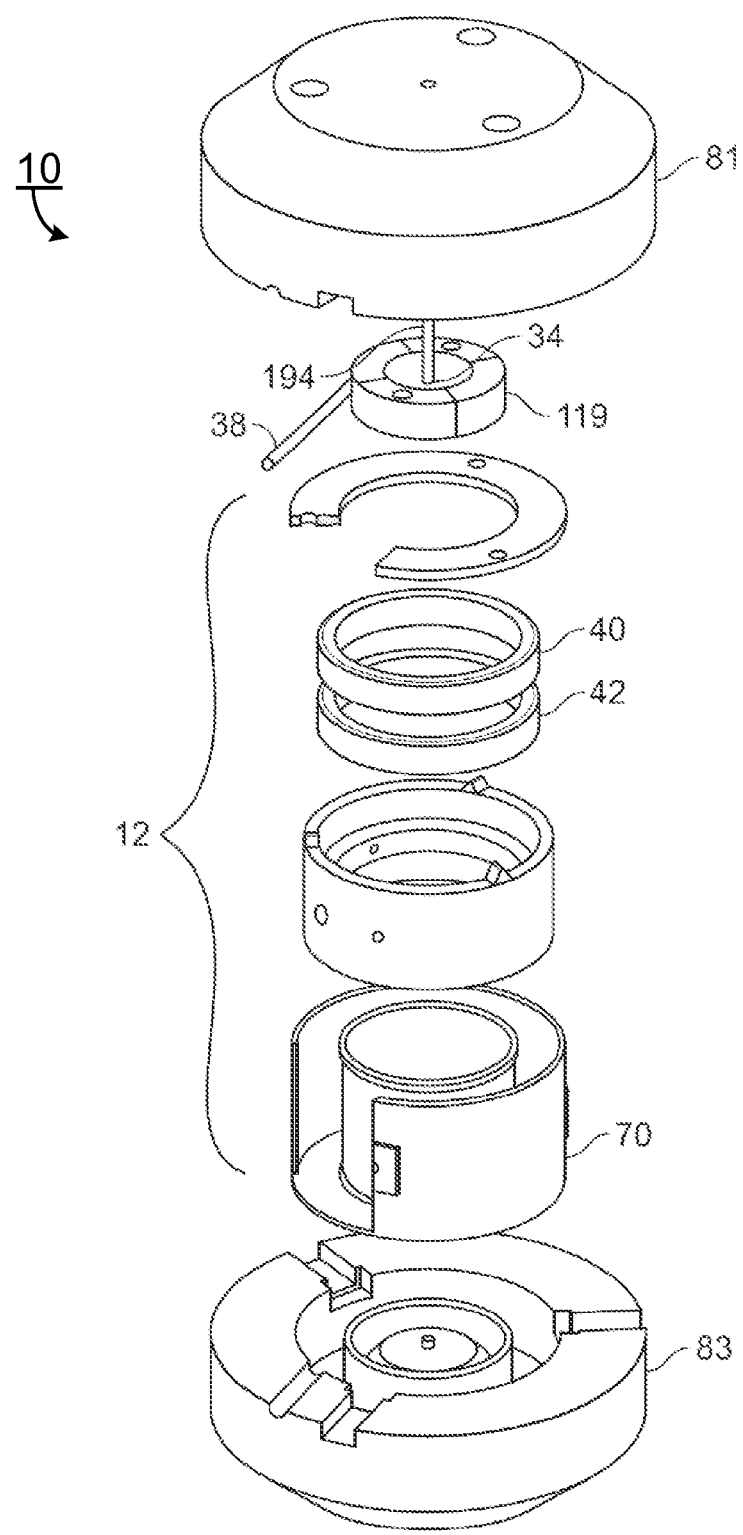
FIG. 2 is an exploded perspective view of components of an example synchrocyclotron.

Described herein is an example of a control system for an example particle accelerator for use in a system, such as a proton or ion therapy system. The example particle therapy system includes a particle accelerator—in this example, a synchrocyclotron—mounted on a gantry. The gantry enables the particle accelerator to be rotated around a patient position, as explained in more detail below. In some implementations, the gantry is steel and has two legs mounted for rotation on two respective bearings that lie on opposite sides of a patient. The particle accelerator is supported by a steel truss that is long enough to span a treatment area in which the patient lies and that is attached stably at both ends to the rotating legs of the gantry. As a result of rotation of the gantry around the patient, the particle accelerator also rotates.

In an example implementation, the particle accelerator (e.g., the synchrocyclotron) includes a cryostat that holds a superconducting coil for conducting a current that generates a magnetic field (B). In this example, the cryostat uses liquid helium (He) to maintain the coil at superconducting temperatures, e.g., 4° Kelvin (K). Magnetic yokes are adjacent (e.g., around) the cryostat, and define a cavity in which particles are accelerated. The cryostat is attached to the magnetic yokes through straps or the like.

In this example implementation, the particle accelerator includes a particle source (e.g., a Penning Ion Gauge—PIG source) to provide a plasma column to the cavity. Hydrogen gas is ionized to produce the plasma column. A voltage source provides a radio frequency (RF) voltage to the cavity to accelerate particles from the plasma column. As noted, in this example, the particle accelerator is a synchrocyclotron. Accordingly, the RF voltage is swept across a range of frequencies to account for relativistic effects on the particles (e.g., increasing particle mass) when extracting particles from the column. The magnetic field produced by the coil causes particles accelerated from the plasma column to accelerate orbitally within the cavity. A ferromagnetic arrangement (e.g., a magnetic regenerator) is positioned in the cavity to adjust the existing magnetic field inside the cavity to thereby change locations of successive orbits of the particles accelerated from the plasma column so that, eventually, the particles output to an extraction channel that passes through the yokes. The extraction channel receives particles accelerated from the plasma column and outputs the received particles from the cavity. Elements both inside and outside the extraction channel shape and focus the particle beam for application.

A control system can control the behavior of the particle accelerator. In operation, a particle beam from the particle accelerator is applied to a patient in accordance with a particular treatment plan. A prescription defines operational characteristics of the particle therapy system that are used to implement the treatment plan. Although a prescription may specify any number of operational characteristics appropriate to a particular particle therapy system, in an implementation, the prescription specifies one or more of the following: particle dose, particle dose rate, patient position (as defined by a "couch" on which the patient lies), patient couch rotational angle, gantry rotational angle, beam field size, beam depth, an extent of the beam depth, a configuration of an aperture used to limit the area of the particle beam, and a configuration of a range compensating bolus (or, simply, "bolus") used to customize the penetration depth of the particle beam.

The control system can include a Therapy Control Computer (TCC) that includes a user interface. In an example, the TCC is programmed to receive prescriptions from a hospital and to send treatment records to the hospital. The TCC can also translate the prescription into machine instructions, including, but not limited to, commands, parameters, and/or other machine-usable information.

The TCC can send the translated machine instructions to a Master Control Computer (MCC). The MCC can include a real-time operating system to execute commands at exact times in an exact order. In an example, the MCC is programmed to send machine instructions to slow and fast input/output modules.

In an example implementation, the slow I/O modules are used to send instructions to motor controllers. The motor controllers may control any movable component of the particle accelerator (e.g., field shaping wheels, scattering foils, a rotating capacitor, a depth modulator wheel, the gantry, etc.).

In an example implementation, the fast I/O modules are used for more time sensitive control. For example, it could be appropriate to use the fast I/O module to control an RF voltage source and/or a particle source (because it can be important for one to be turned at exact times relative to the other). The fast I/O modules can also be used to receive data that samples the position of the modulator wheel (because a very high sampling rate may be appropriate).

The slow and fast I/O modules use the machine instructions to configure the particle therapy system so that it has operational characteristics appropriate for the treatment plan. The particle therapy system is configurable on a case-by-case basis.

The techniques described herein for controlling the particle therapy system are not limited to use with a particular particle therapy system, but rather may be used in any appropriate particle therapy system. The foregoing techniques also may be used in other appropriate medical treatment or diagnostic systems.

An example of a particle therapy system in which the foregoing techniques may be used is provided below.

EXAMPLE PARTICLE THERAPY SYSTEM

Referring to FIG. 1, a charged particle radiation therapy system 500 includes a beam-producing particle accelerator 502 having a weight and size small enough to permit it to be mounted on a rotating gantry 504 with its output directed straight (that is, essentially directly) from the accelerator housing toward a patient 506.

In some implementations, the steel gantry has two legs 508, 510 mounted for rotation on two respective bearings 512, 514 that lie on opposite sides of the patient. The accelerator is supported by a steel truss 516 that is long enough to span a treatment area 518 in which the patient lies (e.g., twice as long as a tall person, to permit the person to be rotated fully within the space with any desired target area of the patient remaining in the line of the beam) and is attached stably at both ends to the rotating legs of the gantry.

In some examples, the rotation of the gantry is limited to a range 520 of less than 360 degrees, e.g., about 180 degrees, to permit a floor 522 to extend from a wall of the vault 524 that houses the therapy system into the patient treatment area. The limited rotation range of the gantry also reduces the required thickness of some of the walls, which provide radiation shielding of people outside the treatment area. A range of 180 degrees of gantry rotation is enough to cover all treatment approach angles, but providing a larger range of travel can be useful. For example the range of rotation may be between 180 and 330 degrees and still provide clearance for the therapy floor space.

The horizontal rotational axis 532 of the gantry is located nominally one meter above the floor where the patient and therapist interact with the therapy system. This floor is positioned about 3 meters above the bottom floor of the therapy system shielded vault. The accelerator can swing under the raised floor for delivery of treatment beams from below the rotational axis. The patient couch moves and rotates in a substantially horizontal plane parallel to the rotational axis of the gantry. The couch can rotate through a range 534 of about 270 degrees in the horizontal plane with this configuration. This combination of gantry and patient rotational ranges and degrees of freedom allow the therapist to select virtually any approach angle for the beam. If needed, the patient can be placed on the couch in the opposite orientation and then all possible angles can be used.

In some implementations, the accelerator uses a synchrocyclotron configuration having a very high magnetic field superconducting electromagnetic structure. Because the bend radius of a charged particle of a given kinetic energy is reduced in direct proportion to an increase in the magnetic field applied to it, the very high magnetic field superconducting magnetic structure permits the accelerator to be made smaller and lighter. The synchrocyclotron uses a magnetic field that is uniform in rotation angle and falls off in strength with increasing radius. Such a field shape can be achieved regardless of the magnitude of the magnetic field, so in theory there is no upper limit to the magnetic field strength (and therefore the resulting particle energy at a fixed radius) that can be used in a synchrocyclotron.

Superconducting materials lose their superconducting properties in the presence of very high magnetic fields. High performance superconducting wire windings are used to allow very high magnetic fields to be achieved. Superconducting materials typically need to be cooled to low temperatures for their superconducting properties to be realized. In some examples described here, cryo-coolers are used to bring the superconducting coil windings to temperatures near absolute zero. Using cryo-coolers can reduce complexity and cost.

The synchrocyclotron is supported on the gantry so that the beam is generated directly in line with the patient. The gantry permits rotation of the cyclotron about a horizontal rotational axis that contains a point (isocenter 540) within, or near, the patient. The split truss that is parallel to the rotational axis, supports the cyclotron on both sides.

Because the rotational range of the gantry is limited, a patient support area can be accommodated in a wide area around the isocenter. Because the floor can be extended broadly around the isocenter, a patient support table can be positioned to move relative to and to rotate about a vertical axis 542 through the isocenter so that, by a combination of gantry rotation and table motion and rotation, any angle of beam direction into any part of the patient can be achieved. The two gantry arms are separated by more than twice the height of a tall patient, allowing the couch with patient to rotate and translate in a horizontal plane above the raised floor.

Limiting the gantry rotation angle allows for a reduction in the thickness of at least one of the walls surrounding the treatment room. Thick walls, typically constructed of concrete, provide radiation protection to individuals outside the treatment room. A wall downstream of a stopping proton beam may be about twice as thick as a wall at the opposite end of the room to provide an equivalent level of protection. Limiting the range of gantry rotation enables the treatment room to be sited below earth grade on three sides, while allowing an occupied area adjacent to the thinnest wall reducing the cost of constructing the treatment room.

In the example implementation shown in FIG. 1, the superconducting synchrocyclotron 502 operates with a peak magnetic field in a pole gap of the synchrocyclotron of 8.8 Tesla. The synchrocyclotron produces a beam of protons having an energy of 250 MeV. In other implementations the field strength could be in the range of 6 to 20 Tesla or 4 to 20 Tesla and the proton energy could be in the range of 150 to 300 MeV The radiation therapy system described in this example is used for proton radiation therapy, but the same principles and details can be applied in analogous systems for use in heavy ion (ion) treatment systems.

As shown in FIGS. 2, 3, 4, 5, and 6, an example synchrocyclotron 10 (e.g., 502 in FIG. 1) includes a magnet system 12 that contains an particle source 90, a radiofrequency drive system 91, and a beam extraction system 38. The magnetic field established by the magnet system has a shape appropriate to maintain focus of a contained proton beam using a combination of a split pair of annular superconducting coils 40, 42 and a pair of shaped ferromagnetic (e.g., low carbon steel) pole faces 44, 46.

Figure 7:
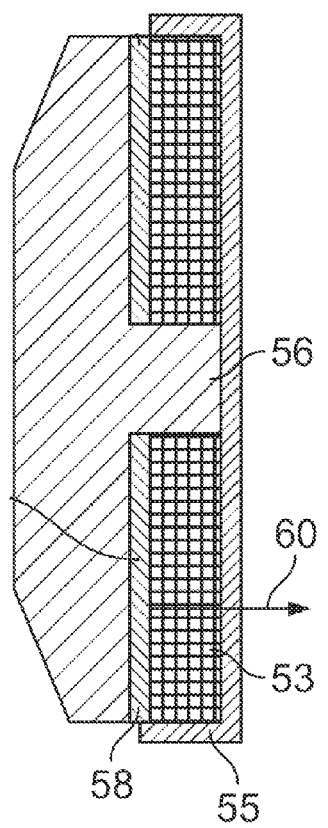
FIG. 7 is a cross-sectional view of a portion of an example reverse bobbin and windings.
Figure 8:
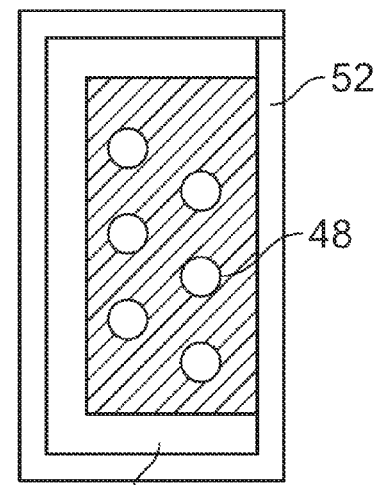
FIG. 8 is a cross-sectional view of an example cable-in-channel composite conductor.

The two superconducting magnet coils are centered on a common axis 47 and are spaced apart along the axis. As shown in FIGS. 7 and 8, the coils are formed by of $Nb_3Sn$-based superconducting 0.8 mm diameter strands 48 (that initially comprise a niobium-tin core surrounded by a copper sheath) deployed in a twisted cable-in-channel conductor geometry. After seven individual strands are cabled together, they are heated to cause a reaction that forms the final (brittle) superconducting material of the wire. After the material has been reacted, the wires are soldered into the copper channel (outer dimensions 3.18×2.54 mm and inner dimensions 2.08×2.08 mm) and covered with insulation 52 (in this example, a woven fiberglass material). The copper channel containing the wires 53 is then wound in a coil having a rectangular cross-section of 8.55 cm×19.02 cm, having 26 layers and 49 turns per layer. The wound coil is then vacuum impregnated with an epoxy compound. The finished coils are mounted on an annular stainless steel reverse bobbin 56. Heater blankets 55 are placed at intervals in the layers of the windings to protect the assembly in the event of a magnet quench.

The entire coil can then be covered with copper sheets to provide thermal conductivity and mechanical stability and then contained in an additional layer of epoxy. The precompression of the coil can be provided by heating the stainless steel reverse bobbin and fitting the coils within the reverse bobbin. The reverse bobbin inner diameter is chosen so that when the entire mass is cooled to 4 K, the reverse bobbin stays in contact with the coil and provides some compression. Heating the stainless steel reverse bobbin to approximately 50 degrees C. and fitting coils at a temperature of 100 degrees Kelvin can achieve this.

Figure 5:
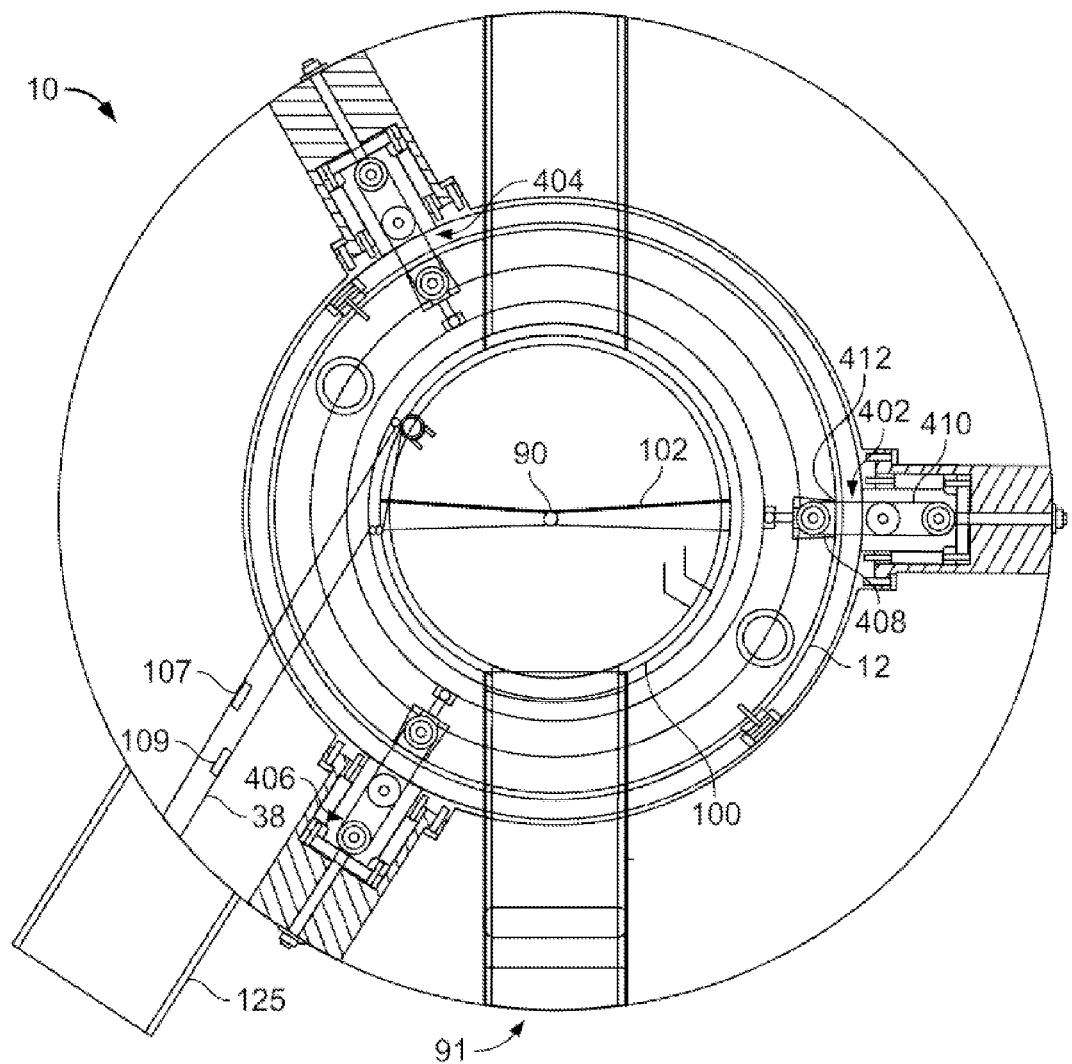
Figure 6:
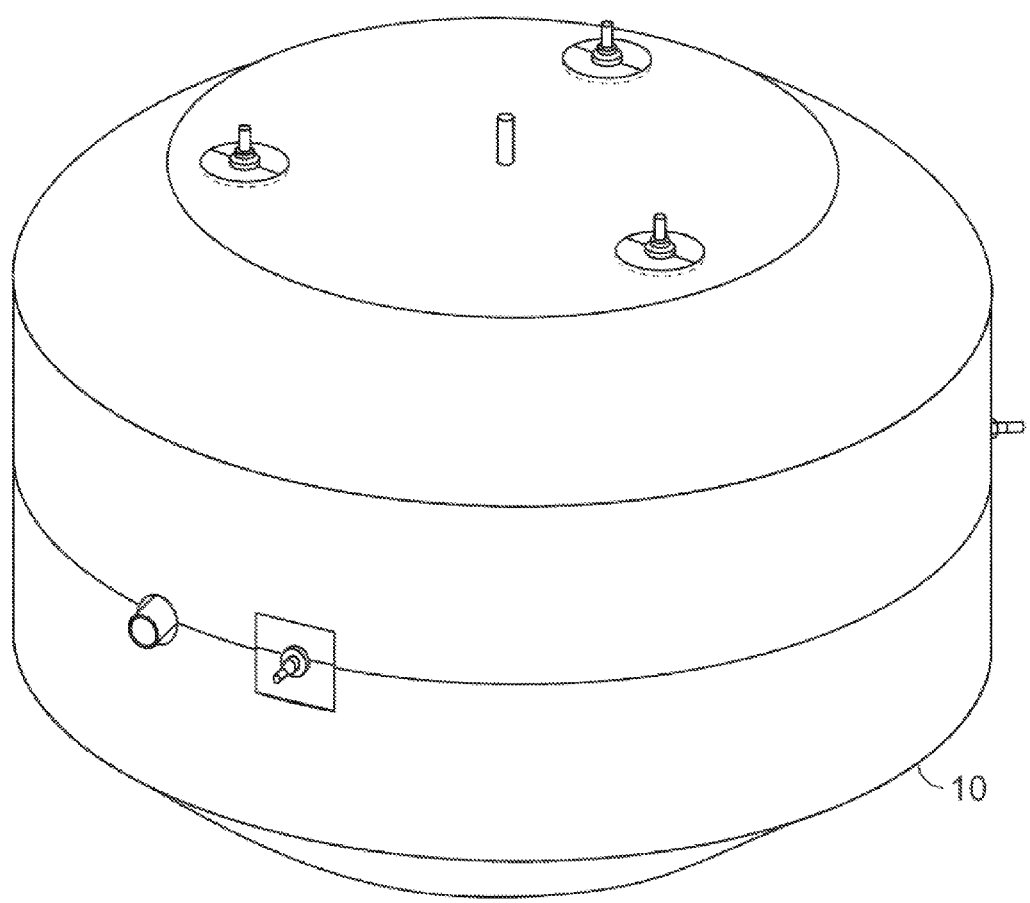
FIG. 6 is a perspective view of an example synchrocyclotron.

The geometry of the coil is maintained by mounting the coils in a reverse rectangular bobbin 56 to exert a restorative force 60 that works against the distorting force produced when the coils are energized. As shown in FIG. 5, the coil position is maintained relative to the magnet yoke and cryostat using a set of warm-to-cold support straps 402, 404, 406. Supporting the cold mass with thin straps reduces the heat leakage imparted to the cold mass by the rigid support system. The straps are arranged to withstand the varying gravitational force on the coil as the magnet rotates on board the gantry. They withstand the combined effects of gravity and the large de-centering force realized by the coil when it is perturbed from a perfectly symmetric position relative to the magnet yoke. Additionally the links act to reduce dynamic forces imparted on the coil as the gantry accelerates and decelerates when its position is changed. Each warm-to-cold support includes one S2 fiberglass link and one carbon fiber link. The carbon fiber link is supported across pins between the warm yoke and an intermediate temperature (50-70 K), and the S2 fiberglass link 408 is supported across the intermediate temperature pin and a pin attached to the cold mass. Each link is 5 cm long (pin center to pin center) and is 17 mm wide. The link thickness is 9 mm. Each pin is made of high strength stainless steel and is 40 mm in diameter.

Figure 3:
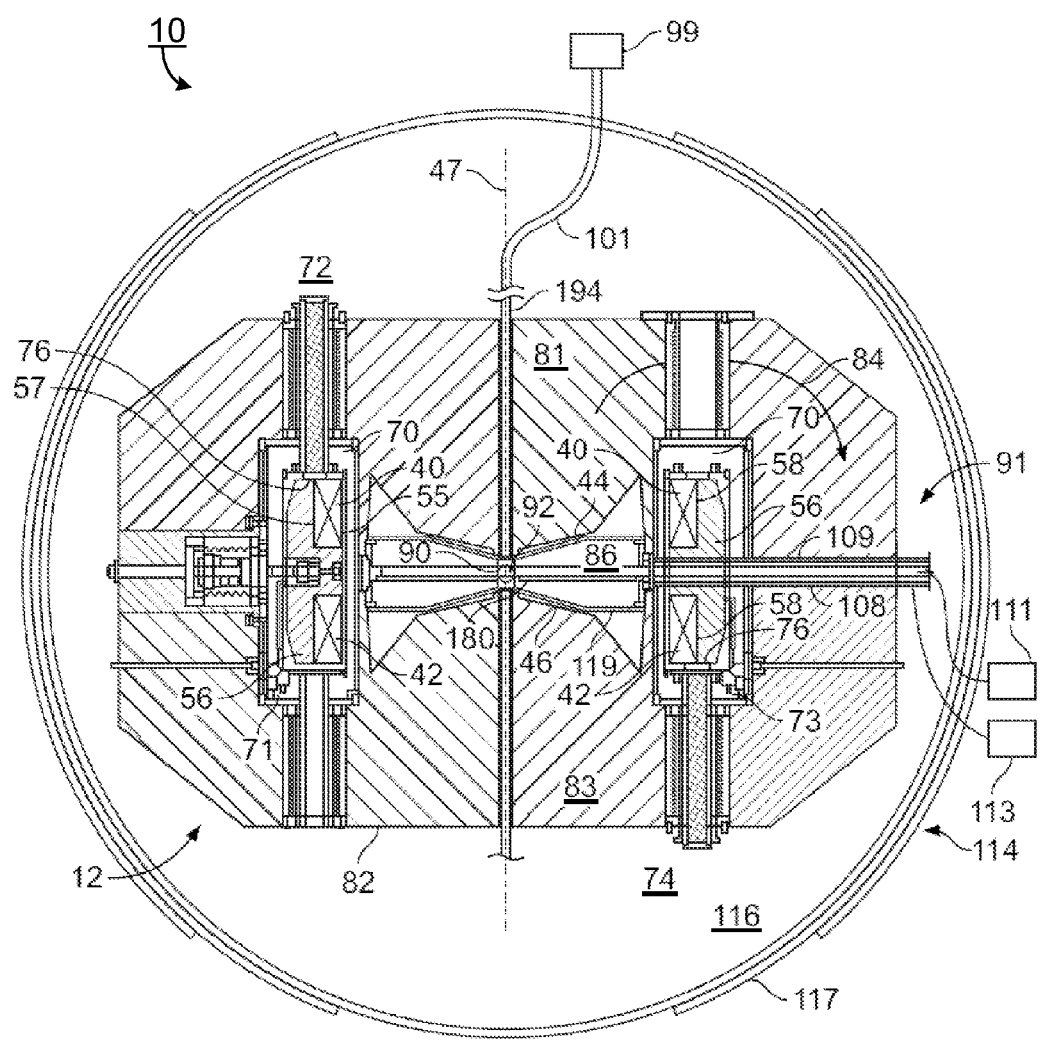
FIGS. 3, 4, and 5 are cross-sectional views of an example synchrocyclotron.
Figure 4:
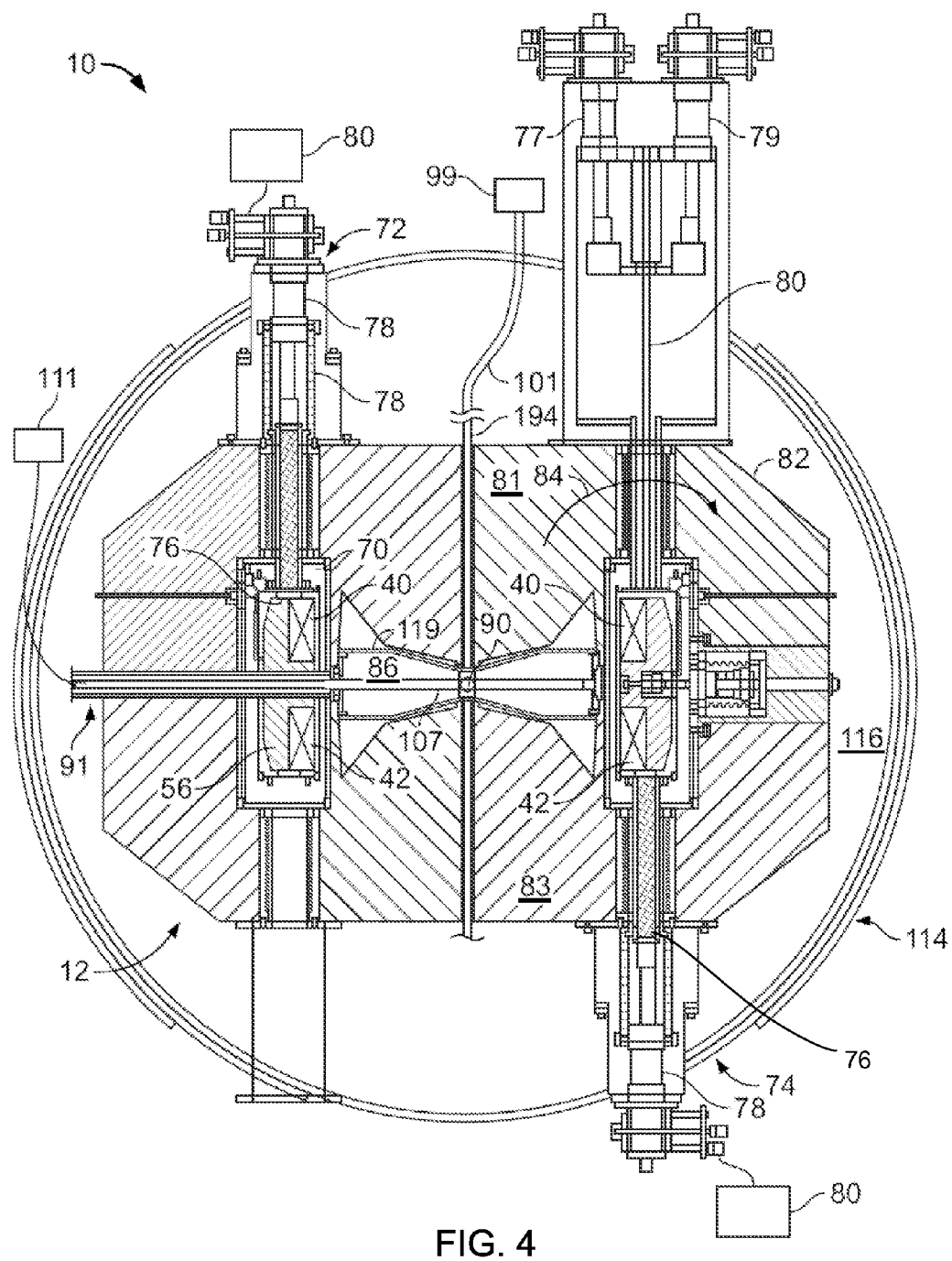

Referring to FIG. 3, the field strength profile as a function of radius is determined largely by choice of coil geometry and pole face shape; the pole faces 44, 46 of the permeable yoke material can be contoured to fine tune the shape of the magnetic field to ensure that the particle beam remains focused during acceleration.

The superconducting coils are maintained at temperatures near absolute zero (e.g., about 4 degrees Kelvin) by enclosing the coil assembly (the coils and the bobbin) inside an evacuated annular aluminum or stainless steel cryostatic chamber 70 that provides a free space around the coil structure, except at a limited set of support points 71, 73. In an alternate version (FIG. 4) the outer wall of the cryostat may be made of low carbon steel to provide an additional return flux path for the magnetic field.

In some implementations, the temperature near absolute zero is achieved and maintained using one single-stage Gifford-McMahon cryo-cooler and three two-stage Gifford McMahon cryo-coolers. Each two stage cryo-cooler has a second stage cold end attached to a condenser that recondenses Helium vapor into liquid Helium. The cryo-cooler heads are supplied with compressed Helium from a compressor. The single-stage Gifford-McMahon cryo-cooler is arranged to cool high temperature (e.g., 50-70 degrees Kelvin) leads that supply current to the superconducting windings.

In some implementations, the temperature near absolute zero is achieved and maintained using two Gifford-McMahon cryo-coolers 72, 74 that are arranged at different positions on the coil assembly. Each cryo-cooler has a cold end 76 in contact with the coil assembly. The cryo-cooler heads 78 are supplied with compressed Helium from a compressor 80. Two other Gifford-McMahon cryo-coolers 77, 79 are arranged to cool high temperature (e.g., 60-80 degrees Kelvin) leads that supply current to the superconducting windings.

The coil assembly and cryostatic chambers are mounted within and fully enclosed by two halves 81, 83 of a pillbox-shaped magnet yoke 82. In this example, the inner diameter of the coil assembly is about 74.6 cm. The iron yoke 82 provides a path for the return magnetic field flux 84 and magnetically shields the volume 86 between the pole faces 44, 46 to prevent external magnetic influences from perturbing the shape of the magnetic field within that volume. The yoke also serves to decrease the stray magnetic field in the vicinity of the accelerator.

Figure 9:
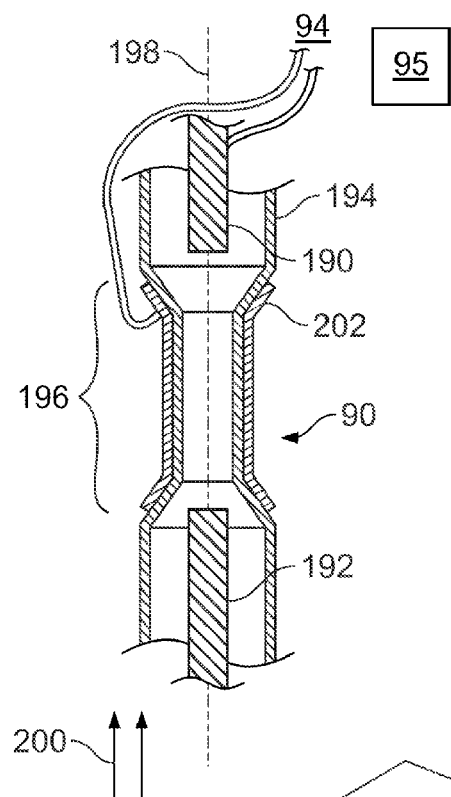
FIG. 9 is a cross-sectional view of an example particle source.

As shown in FIGS. 3 and 9, the synchrocyclotron includes a particle source 90 of a Penning ion gauge geometry located near the geometric center 92 of the magnet structure 82. The particle source may be as described below, or the particle source may be of the type described in U.S. patent application Ser. No. 11/948,662 incorporated herein by reference.

Particle source 90 is fed from a supply 99 of hydrogen through a gas line 101 and tube 194 that delivers gaseous hydrogen. Electric cables 94 carry an electric current from a current source 95 to stimulate electron discharge from cathodes 192, 190 that are aligned with the magnetic field, 200.

In some implementations, the gas in gas tube 101 may include a mixture of hydrogen and one or more other gases. For example, the mixture may contain hydrogen and one or more of the noble gases, e.g., helium, neon, argon, krypton, xenon and/or radon (although the mixture is not limited to use with the noble gases). In some implementations, the mixture may be a mixture of hydrogen and helium. For example, the mixture may contain about 75% or more of hydrogen and about 25% or less of helium (with possible trace gases included). In another example, the mixture may contain about 90% or more of hydrogen and about 10% or less of helium (with possible trace gases included). In examples, the hydrogen/helium mixture may be any of the following: >95%/<5%, >90%/<10%, >85%/<15%, >80%/<20%, >75%/<20%, and so forth.

Possible advantages of using a noble (or other) gas in combination with hydrogen in the particle source may include: increased beam intensity, increased cathode longevity, and increased consistency of beam output.

In this example, the discharged electrons ionize the gas exiting through a small hole from tube 194 to create a supply of positive ions (protons) for acceleration by one semicircular (dee-shaped) radio-frequency plate 100 that spans half of the space enclosed by the magnet structure and one dummy dee plate 102. In the case of an interrupted particle source (an example of which is described in U.S. patent application Ser. No. 11/948,662), all (or a substantial part) of the tube containing plasma is removed at the acceleration region, thereby allowing ions to be more rapidly accelerated in a relatively high magnetic field.

Figure 10:
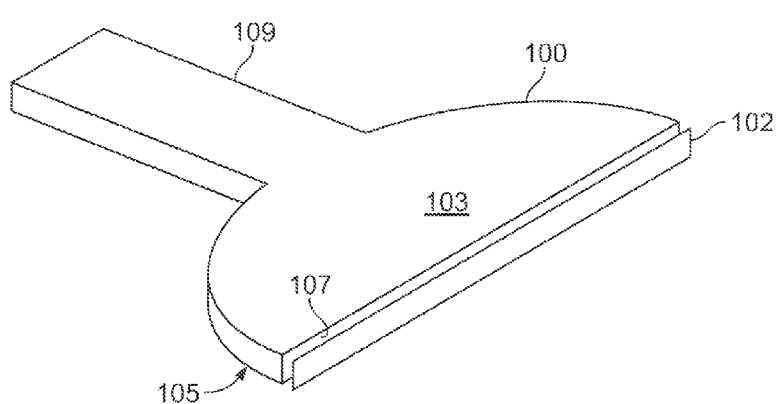
FIG. 10 is a perspective view of an example dee plate and a dummy dee.

As shown in FIG. 10, the dee plate 100 is a hollow metal structure that has two semicircular surfaces 103, 105 that enclose a space 107 in which the protons are accelerated during half of their rotation around the space enclosed by the magnet structure. A duct 109 opening into the space 107 extends through the yoke to an external location from which a vacuum pump 111 can be attached to evacuate the space 107 and the rest of the space within a vacuum chamber 119 in which the acceleration takes place. The dummy dee 102 comprises a rectangular metal ring that is spaced near to the exposed rim of the dee plate. The dummy dee is grounded to the vacuum chamber and magnet yoke. The dee plate 100 is driven by a radio-frequency signal that is applied at the end of a radio-frequency transmission line to impart an electric field in the space 107. The radio frequency electric field is made to vary in time as the accelerated particle beam increases in distance from the geometric center. The radio frequency electric field may be controlled in the manner described in U.S. patent application Ser. No. 11/948,359, entitled "Matching A Resonant Frequency Of A Resonant Cavity To A Frequency Of An Input Voltage", the contents of which are incorporated herein by reference.

For the beam emerging from the centrally located particle source to clear the particle source structure as it begins to spiral outward, a large voltage difference is required across the radio frequency plates. 20,000 Volts is applied across the radio frequency plates. In some versions from 8,000 to 20,000 Volts may be applied across the radio frequency plates. To reduce the power required to drive this large voltage, the magnet structure is arranged to reduce the capacitance between the radio frequency plates and ground. This is done by forming holes with sufficient clearance from the radio frequency structures through the outer yoke and the cryostat housing and making sufficient space between the magnet pole faces.

The high voltage alternating potential that drives the dee plate has a frequency that is swept downward during the accelerating cycle to account for the increasing relativistic mass of the protons and the decreasing magnetic field. The dummy dee does not require a hollow semi-cylindrical structure as it is at ground potential along with the vacuum chamber walls. Other plate arrangements could be used such as more than one pair of accelerating electrodes driven with different electrical phases or multiples of the fundamental frequency. The RF structure can be tuned to keep the Q high during the required frequency sweep by using, for example, a rotating capacitor having intermeshing rotating and stationary blades. During each meshing of the blades, the capacitance increases, thus lowering the resonant frequency of the RF structure. The blades can be shaped to create a precise frequency sweep required. A drive motor for the rotating condenser can be phase locked to the RF generator for precise control. One bunch of particles is accelerated during each meshing of the blades of the rotating condenser.

The vacuum chamber 119 in which the acceleration occurs is a generally cylindrical container that is thinner in the center and thicker at the rim. The vacuum chamber encloses the RF plates and the particle source and is evacuated by the vacuum pump 111. Maintaining a high vacuum insures that accelerating ions are not lost to collisions with gas molecules and enables the RF voltage to be kept at a higher level without arcing to ground.

Protons traverse a generally spiral orbital path beginning at the particle source. In half of each loop of the spiral path, the protons gain energy as they pass through the RF electric field in space 107. As the ions gain energy, the radius of the central orbit of each successive loop of their spiral path is larger than the prior loop until the loop radius reaches the maximum radius of the pole face. At that location a magnetic and electric field perturbation directs ions into an area where the magnetic field rapidly decreases, and the ions depart the area of the high magnetic field and are directed through an evacuated tube 38, referred to herein as the extraction channel, to exit the yoke of the cyclotron. A magnetic regenerator may be used to change the magnetic field perturbation to direct the ions. The ions exiting the cyclotron will tend to disperse as they enter the area of markedly decreased magnetic field that exists in the room around the cyclotron. Beam shaping elements 107, 109 in the extraction channel 38 redirect the ions so that they stay in a straight beam of limited spatial extent.

The magnetic field within the pole gap needs to have certain properties to maintain the beam within the evacuated chamber as it accelerates. The magnetic field index n, which is shown below, $$n = -(r/B)dB/dr,$$

should be kept positive to maintain this "weak" focusing. Here r is the radius of the beam and B is the magnetic field. Additionally, in some implementations, the field index needs to be maintained below 0.2, because at this value the periodicity of radial oscillations and vertical oscillations of the beam coincide in a vr=2 $v_z$ resonance. The betatron frequencies are defined by $v_r=(1-n)^{1/2}$ and $v_z=n^{1/2}$. The ferromagnetic pole face is designed to shape the magnetic field generated by the coils so that the field index n is maintained positive and less than 0.2 in the smallest diameter consistent with a 250 MeV beam in the given magnetic field.

As the beam exits the extraction channel it is passed through a beam formation system 125 (FIG. 5) that can be programmably controlled to create a desired combination of scattering angle and range modulation for the beam. Beam formation system 125 may be used in conjunction with an inner gantry 601 (FIG. 14) to direct a beam to the patient.

During operation, the plates absorb energy from the applied radio frequency field as a result of conductive resistance along the surfaces of the plates. This energy appears as heat and is removed from the plates using water cooling lines 108 that release the heat in a heat exchanger 113 (FIG. 3).

Stray magnetic fields exiting from the cyclotron are limited by both the pillbox magnet yoke (which also serves as a shield) and a separate magnetic shield 114. The separate magnetic shield includes of a layer 117 of ferromagnetic material (e.g., steel or iron) that encloses the pillbox yoke, separated by a space 116. This configuration that includes a sandwich of a yoke, a space, and a shield achieves adequate shielding for a given leakage magnetic field at lower weight. In some implementations, the synchrocyclotron may have an active return system to reduce stray magnetic fields. An example of an active return system is described in U.S. patent application Ser. No. 13/907,601, which was filed on May 31, 2013, the contents of which are incorporated herein by reference.

As mentioned, the gantry allows the synchrocyclotron to be rotated about the horizontal rotational axis 532. The truss structure 516 has two generally parallel spans 580, 582. The synchrocyclotron is cradled between the spans about midway between the legs. The gantry is balanced for rotation about the bearings using counterweights 122, 124 mounted on ends of the legs opposite the truss.

The gantry is driven to rotate by an electric motor mounted to one or both of the gantry legs and connected to the bearing housings by drive gears . The rotational position of the gantry is derived from signals provided by shaft angle encoders incorporated into the gantry drive motors and the drive gears.

At the location at which the ion beam exits the cyclotron, the beam formation system 125 acts on the ion beam to give it properties suitable for patient treatment. For example, the beam may be spread and its depth of penetration varied to provide uniform radiation across a given target volume. The beam formation system can include passive scattering elements as well as active scanning elements.

All of the active systems of the synchrocyclotron (the current driven superconducting coils, the RF-driven plates, the vacuum pumps for the vacuum acceleration chamber and for the superconducting coil cooling chamber, the current driven particle source, the hydrogen gas source, and the RF plate coolers, for example), may be controlled by appropriate synchrocyclotron control electronics (not shown), which may include, e.g., one or more computers programmed with appropriate programs to effect control.

The control of the gantry, the patient support, the active beam shaping elements, and the synchrocyclotron to perform a therapy session is achieved by appropriate therapy control electronics (not shown).

Figure 11:
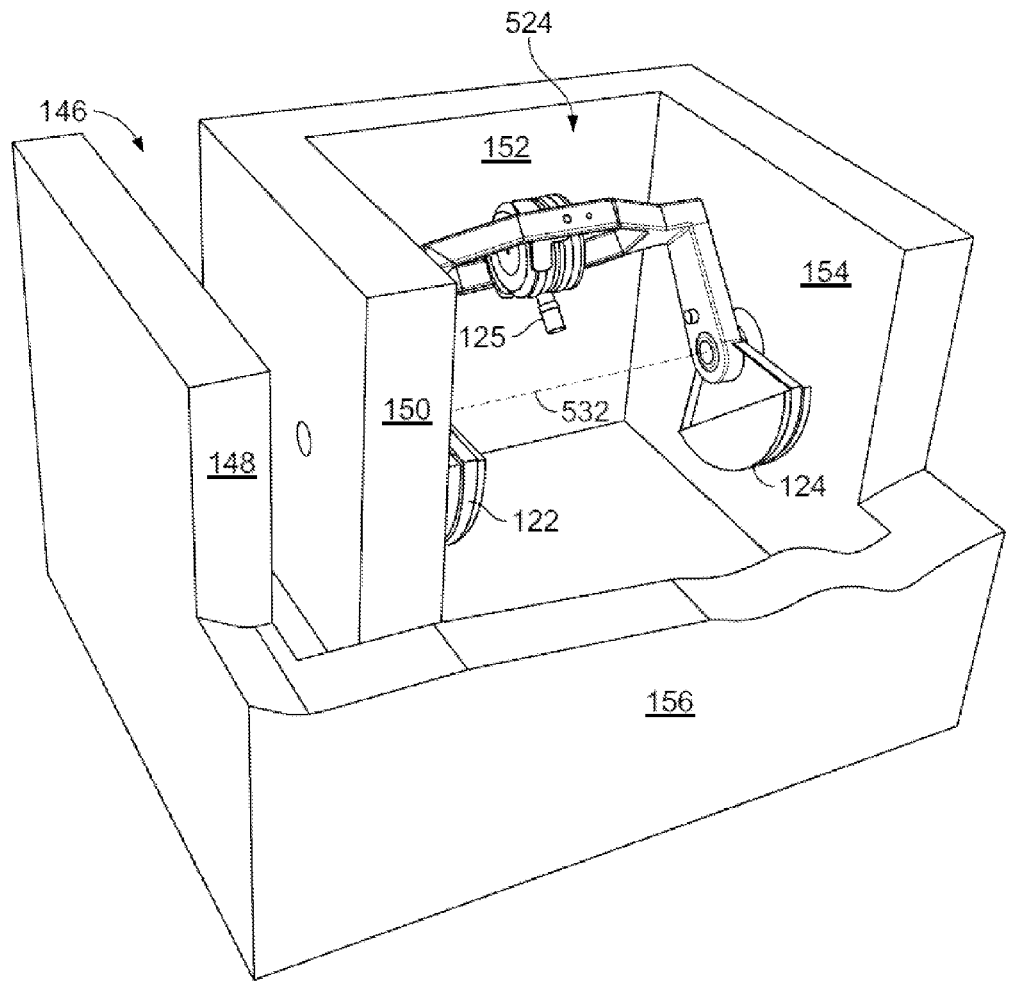
FIG. 11 is a perspective view of an example vault.
Figure 12:
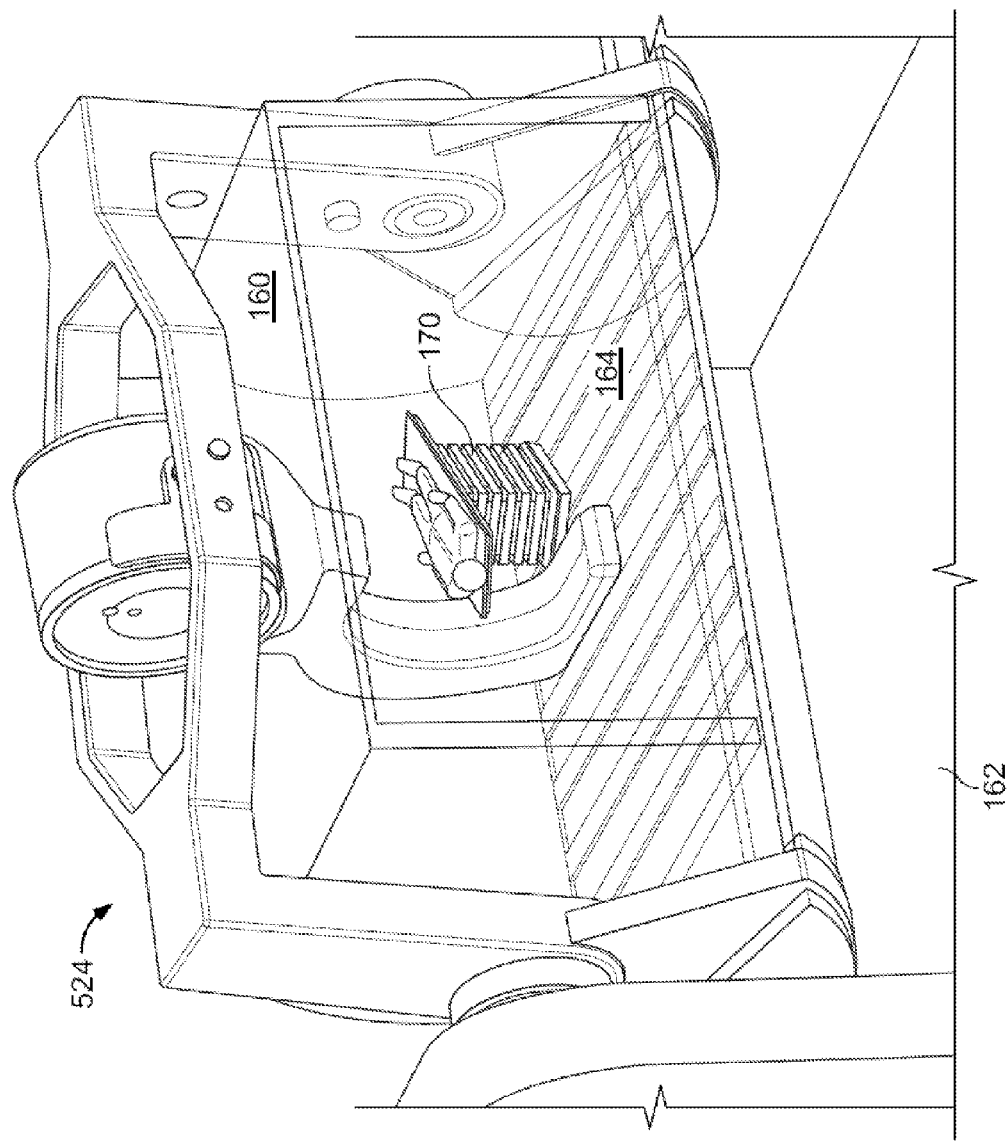
FIG. 12 is a perspective view of an example treatment room with a vault.

As shown in FIGS. 1, 11, and 12, the gantry bearings are supported by the walls of a cyclotron vault 524. The gantry enables the cyclotron to be swung through a range 520 of 180 degrees (or more) including positions above, to the side of, and below the patient. The vault is tall enough to clear the gantry at the top and bottom extremes of its motion. A maze 146 sided by walls 148, 150 provides an entry and exit route for therapists and patients. Because at least one wall 152 is not in line with the proton beam directly from the cyclotron, it can be made relatively thin and still perform its shielding function. The other three side walls 154, 156, 150/148 of the room, which may need to be more heavily shielded, can be buried within an earthen hill (not shown). The required thickness of walls 154, 156, and 158 can be reduced, because the earth can itself provide some of the needed shielding.

Figure 13:
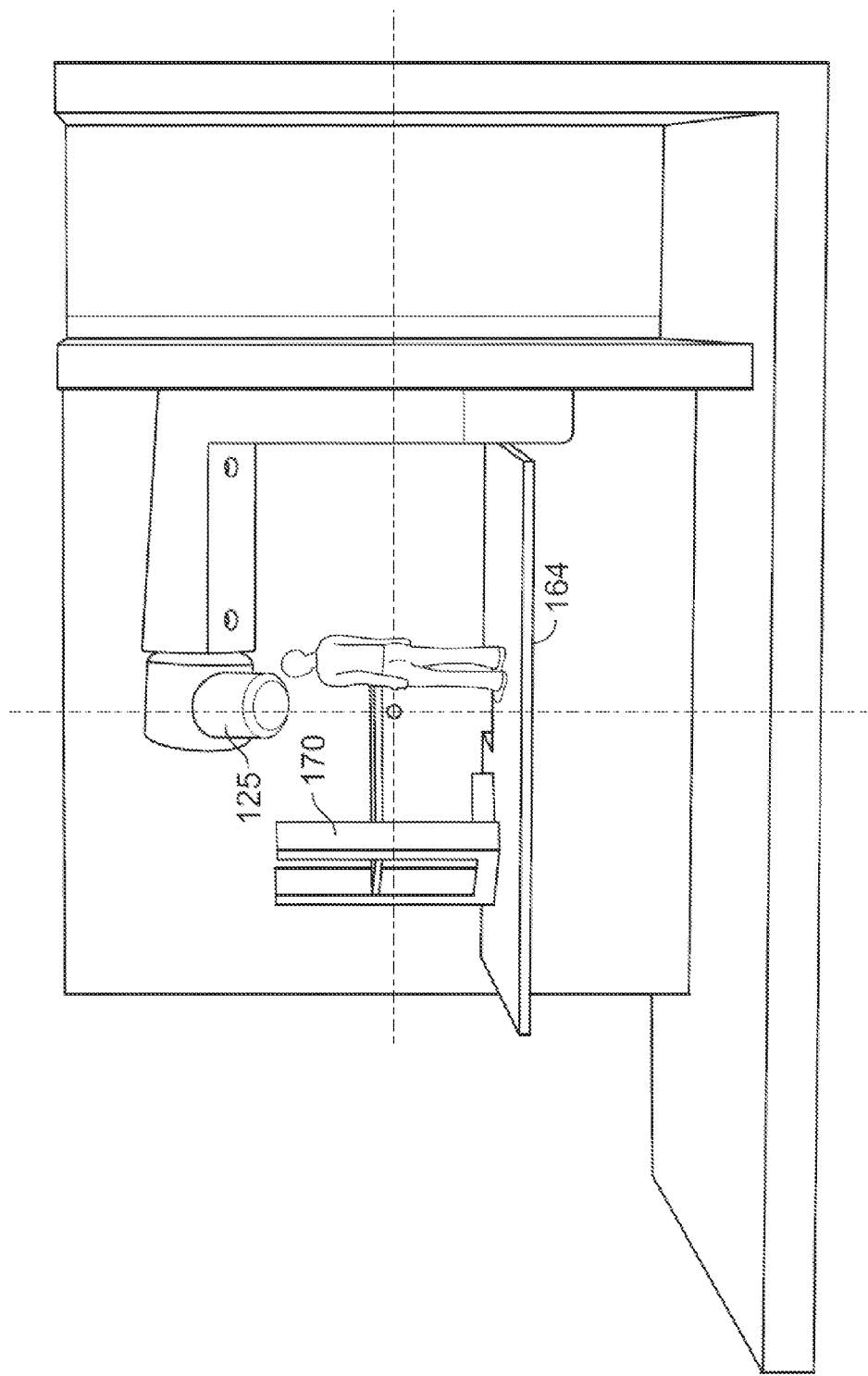
FIG. 13 shows a patient positioned next to a particle accelerator.

Referring to FIGS. 12 and 13, for safety and aesthetic reasons, a therapy room 160 may be constructed within the vault. The therapy room is cantilevered from walls 154, 156, 150 and the base 162 of the containing room into the space between the gantry legs in a manner that clears the swinging gantry and also maximizes the extent of the floor space 164 of the therapy room. Periodic servicing of the accelerator can be accomplished in the space below the raised floor. When the accelerator is rotated to the down position on the gantry, full access to the accelerator is possible in a space separate from the treatment area. Power supplies, cooling equipment, vacuum pumps and other support equipment can be located under the raised floor in this separate space. Within the treatment room, the patient support 170 can be mounted in a variety of ways that permit the support to be raised and lowered and the patient to be rotated and moved to a variety of positions and orientations.

Figure 14:
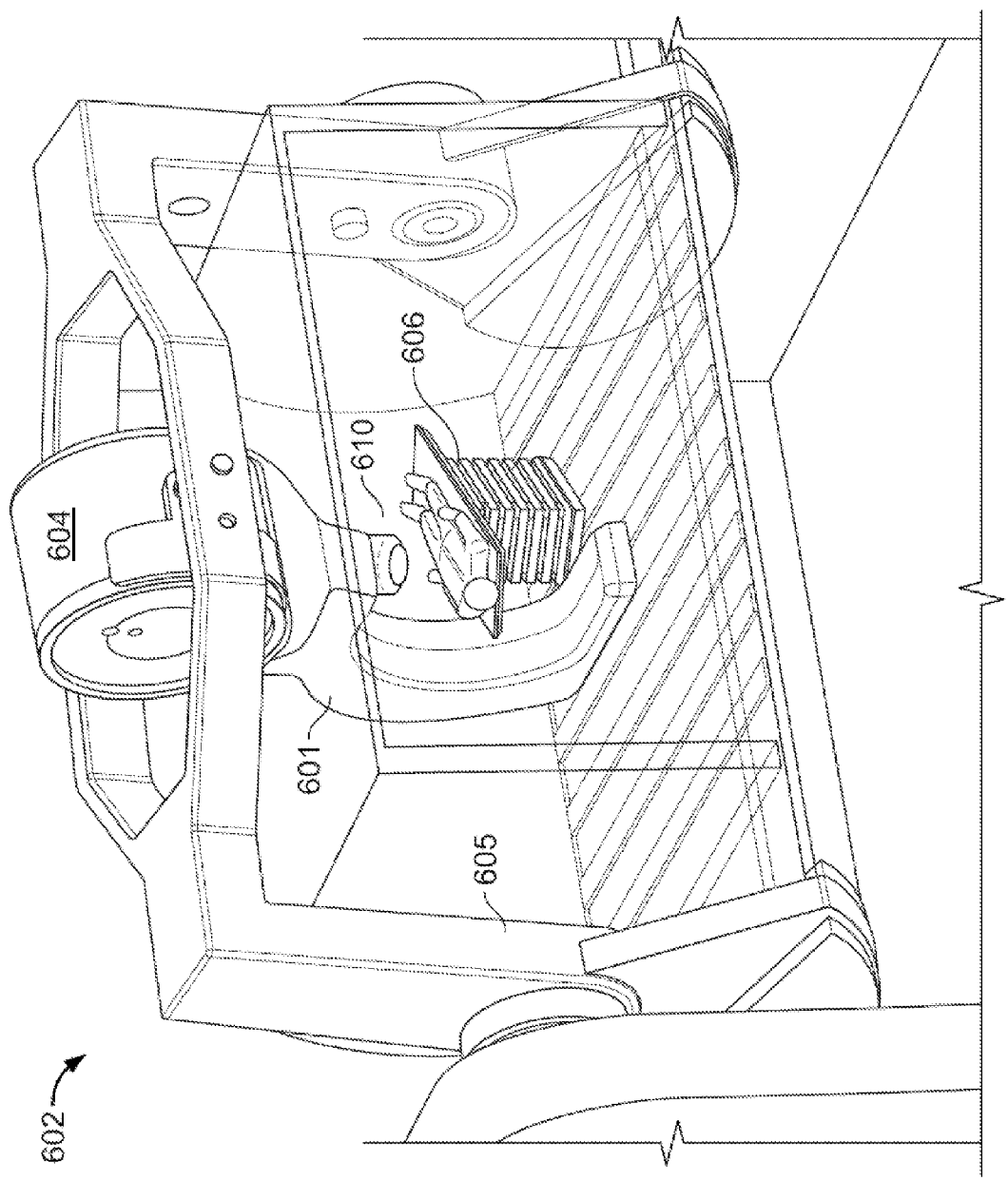
FIG. 14 shows a patient positioned within an example inner gantry in a treatment room.

In system 602 of FIG. 14, a beam-producing particle accelerator of the type described herein, in this case synchrocyclotron 604, is mounted on rotating gantry 605. Rotating gantry 605 is of the type described herein, and can angularly rotate around patient support 606. This feature enables synchrocyclotron 604 to provide a particle beam directly to the patient from various angles. For example, as in FIG. 14, if synchrocyclotron 604 is above patient support 606, the particle beam may be directed downwards toward the patient. Alternatively, if synchrocyclotron 604 is below patient support 606, the particle beam may be directed upwards toward the patient. The particle beam is applied directly to the patient in the sense that an intermediary beam routing mechanism is not required. A routing mechanism, in this context, is different from a shaping or sizing mechanism in that a shaping or sizing mechanism does not re-route the beam, but rather sizes and/or shapes the beam while maintaining the same general trajectory of the beam.

Further details regarding an example implementation of the foregoing system may be found in U.S. Pat. No. 7,728, 311, filed on Nov. 16, 2006 and entitled "Charged Particle Radiation Therapy", and in U.S. patent application Ser. No. 12/275,103, filed on Nov. 20, 2008 and entitled "Inner Gantry". The contents of U.S. Pat. No. 7,728,311 and in U.S. patent application Ser. No. 12/275,103 are incorporated herein by reference. In some implementations, the synchrocyclotron may be a variable-energy device, such as that described in U.S. patent application Ser. No. 13/916,401, filed on Jun. 12, 2013, the contents of which are incorporated herein by reference.

EXAMPLE IMPLEMENTATIONS

Figure 15:
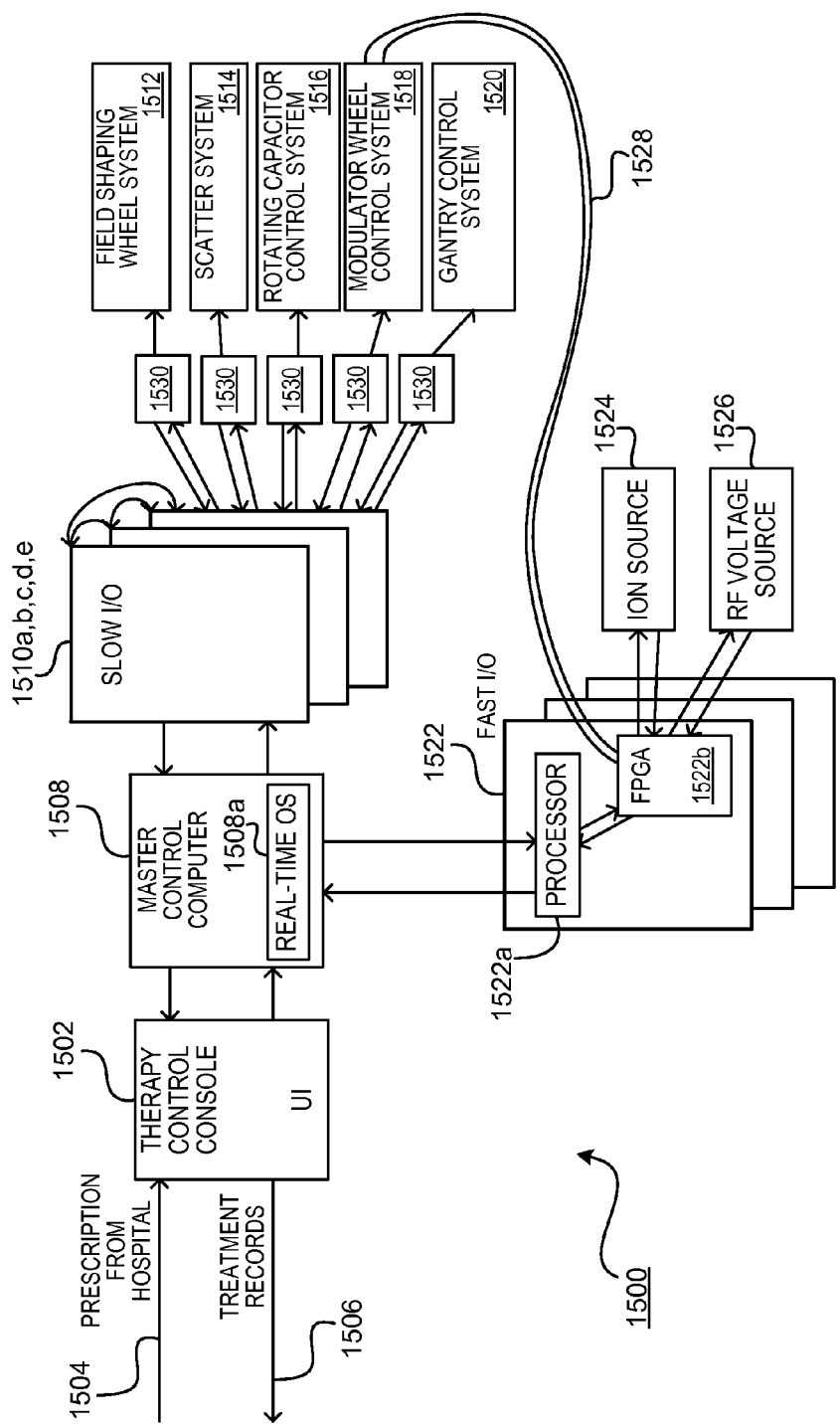
FIG. 15 is a block diagram showing an example of a control system for a particle accelerator.

Referring to FIG. 15, an example control system 1500 may be used to control the example particle therapy system described above, e.g., with respect to FIGS. 1-14. The control system 155 may contain a Therapy Control Computer (TCC) 1502 that can include a user interface, a Master Control Computer (MCC) 1508 for processing machine instructions in real-time, and I/O modules 1510, 1522 that can send machine instructions to components of the particle accelerator.

In some examples, the TCC 1502 is networked to a hospital so the TCC 1502 can receive patent prescriptions 1504 from the hospital before treatment and send treatment records 1506 to the hospital after treatment. The TCC 1502 can also translate a received patient prescription 1504 into machine parameters that can be understood by a Master Control Computer (MCC) 1508.

The MCC 1508 can include a real-time operating system 1508a. A real-time operating system 1508a is an operating system that serves real-time requests. For example, a non-real-time operating systems may delay serving a request if it is busy doing something else.

The MCC 1508 can be configured to receive machine parameters from the TCC 1502. The MCC 1508 can translate the machine parameters into specific machine instructions that can be understood by one or more slow input/output modules 1510 and one or more fast input/output modules 1522, described in more detail below. The MCC 1508, with the aid of the real-time operating system 1508a, can send machine instructions to the slow 1510 and fast I/O modules 1522 at specified times in a specified order.

The slow I/O modules 1510 can be used to send machine instructions to aspects of the particle accelerator that do not require relatively fast transmission. In this context, "slow" refers to an operational speed that is less than a "fast" operational speed, and "fast refers to an operational speed that is greater than "slow" operational speed. The terms "slow" and "fast" are not intended to refer to, or to imply, any specific operational speeds and are relative terms, not absolute values.

In some examples, the slow I/O modules 1510 are programmable logic controllers with speeds in the order of milliseconds. For example, a machine instruction may take more than 1 ms to arrive at the particular component. Slow I/O modules 1510 can be configured to send machine instructions to one or more motor controllers 1530.

In some examples, the slow I/O modules 1510 send machine instructions to one or more motor controllers 1530. In an example, the motor controllers 1530 can control motors that are part of a field shaping wheel system 1512, a scatterer system 1514, a rotating capacitor system 1516, a modular wheel control system 1518, or a gantry control system 1520, although the motor controllers can be part of any system that uses a motor.

Figure 16:
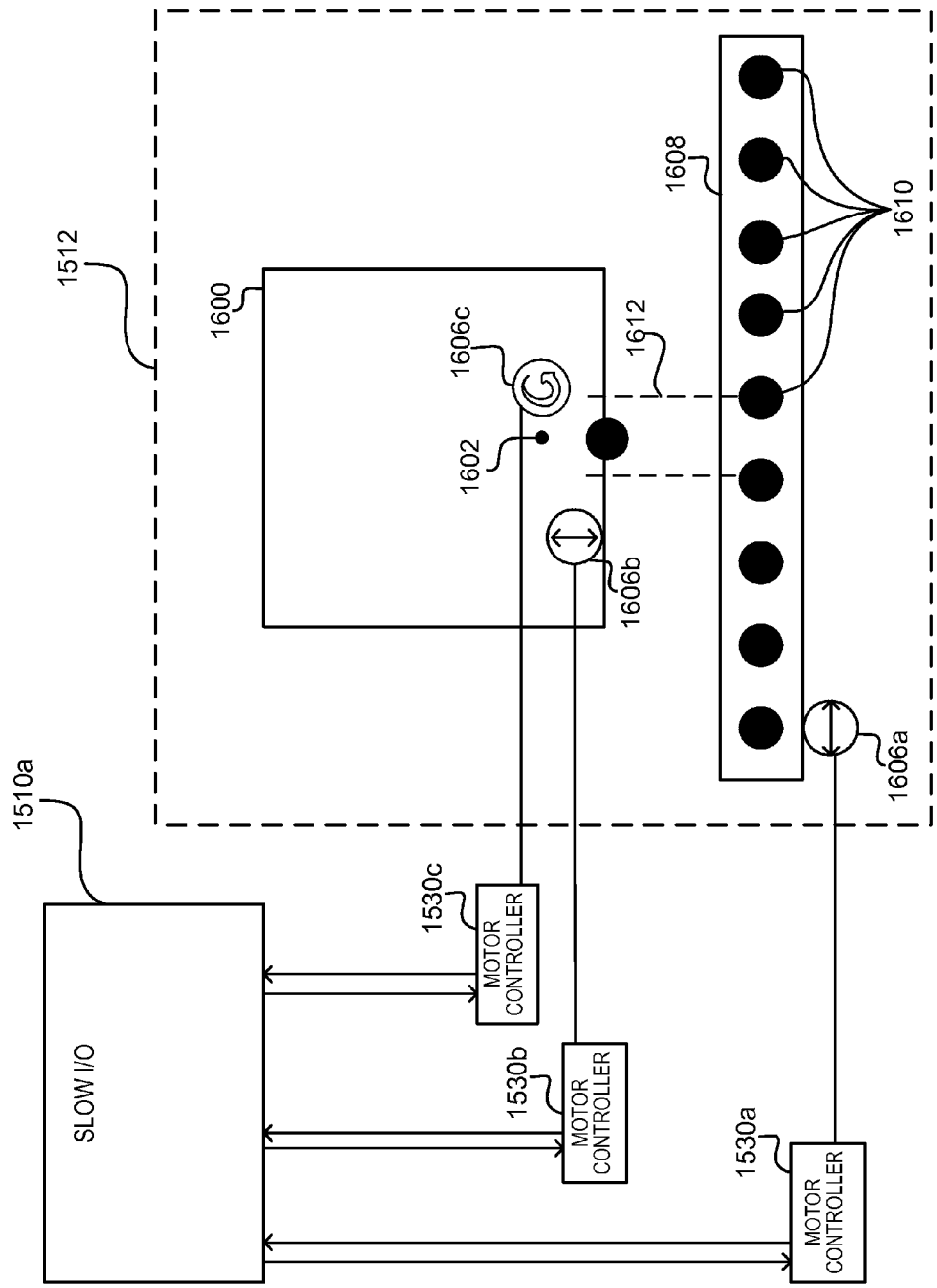
FIG. 16 shows an example field shaping wheel system.

Referring to FIG. 16, an example field shaping wheel system 1512 can be used to shape the particle beam to a desired shape. The field shaping wheel system 1512 can include a wheel rack 1608, a wheel chamber 1612, wheels 1610, and wheel motors 1606a-c. Each wheel 1610 alters the shape of the magnetic field in a different way. An example slow I/O module 1510a can send machine instructions to motor controllers 1530a-c depending on which wheel 1610 is appropriate (e.g., based on the translated prescription). Each motor controller 1530a-c can control one wheel motor 1606a-c. Wheel motor 1606a can move the wheel rack 1608 side to side until the selected wheel 1610 is situated below the wheel chamber 1612. Once the selected wheel 1610 is horizontally aligned, wheel motor 1606b can move the wheel up into the wheel chamber 1612. Once the selected wheel 1610 is situated in the wheel chamber 1612, wheel motor 1606c can rotate it. Different rotational positions can have different effects on the shape of the magnetic field that the particle beam experiences.

Figure 17:
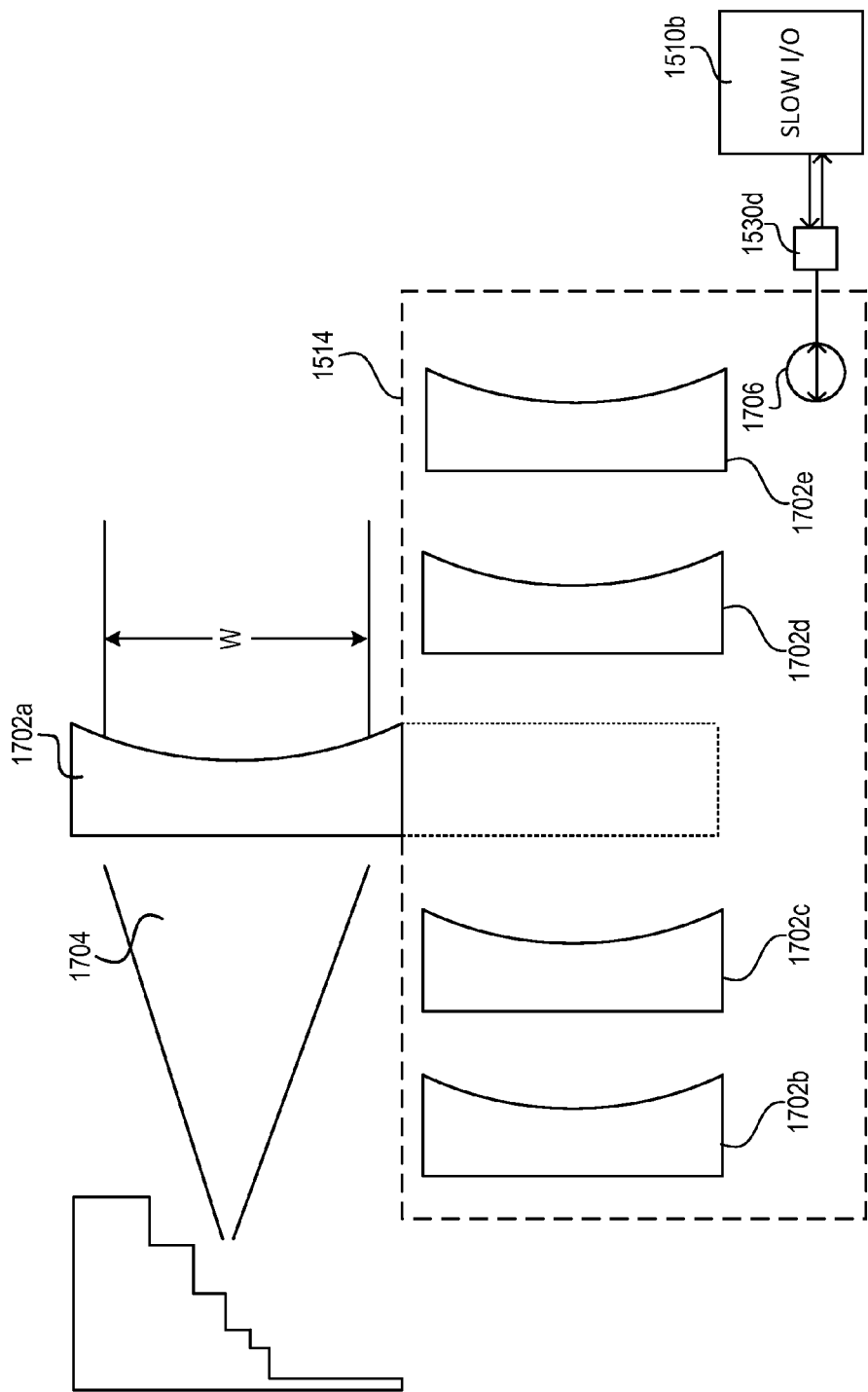
FIG. 17 is a side view showing a beam path that includes an example modulator wheel and an example scatterer.

As explained above, the beam formation system (125 of FIG. 5) can create a desired combination of scattering angle and range modulation for the particle beam. Referring to FIG. 17, the output particle beam 1704 may have a Gaussian profile (with a majority of particles at the center of the beam) after it passes through the extraction channel (and the modulator wheel, described below). A scatterer 1702a can reshape the particle beam so that the particle beam has a substantially constant width (w). For example, the particle beam may have a circular cross-section. In this implementation, scatterer 1702a is a scattering foil, all or part of which may be made of a metal, such as lead. As shown, scatterer 1702a has a side that is convex in shape, and includes more lead at its edges than at its center. To achieve a larger field beam size, thicker lead may be used, and vice versa. In this regard, the particle therapy system may include multiple scatterers 1702a-e, which may be switched into, or out of, the path of the particle beam in order to achieve a particle beam field size (cross-sectional area).

Different treatments require different scattering angles and range modulations. The scatterer system 1514 can be used to place the appropriate scatterer 1702a-e in the particle beam path. In an example, the scatterer system 1514 can include one or more motors 1706 configured to place different scatterers 1702a-e in the particle beam path in a way similar to the field shaping wheel system 1512. An example slow I/O module 1510b can send machine instructions to a motor controller 1530d depending on which scatterer 1702a-e is appropriate (e.g., based on the translated prescription). The motor controller 1530d can control the motor 1706 such that the motor 1706 places the appropriate scatterer 1702a-e in the beam formation system 125.

As explained above, a rotating capacitor can be used tune the RF structure during the frequency sweep. In an example, a rotating capacitor system 1516 can be configured to rotate some of the blades of the rotating capacitor to an appropriate position. The rotating capacitor system 1516 can include one or more motors that can control the rotating capacitor in a way similar to the field shaping wheel system 1512. An example slow I/O module 1510 can send machine instructions to motor controllers to rotate the capacitor at a fixed speed. An associated fast I/O system can coordinate the rotational speed of the modulator wheel with the rotational speed of the capacitor to insure the beam pulses from the synchrocyclotron are uniformly distributed on the modulator wheel azimuthally As explained above, the gantry enables the particle accelerator to be rotated around a patient position. The gantry control system 1520 can be used to rotate the gantry into the appropriate position (e.g., to apply treatment at the desired angle). In an example, the gantry control system 1520 can include one or more motors configured to rotate the gantry to the appropriate position in a way similar to systems 1512, 1514, and 1516. An example slow I/O module 1510 can send machine instructions to motor controllers 1530 depending on what gantry position is appropriate (e.g., based on the translated prescription). The motor controllers 1530 can control the motors such that the motors rotate the gantry into the correct position.

Downstream from (e.g., after) the extraction channel, various devices are used to affect the particle beam output. One such device is configured to spread-out Bragg peaks of the particle beam to achieve a substantially uniform particle beam dose at a range of depths within the patient. As described in wikipedia.org, "[w]hen a fast charged particle moves through matter, it ionizes atoms of the material and deposits a dose along its path. A peak occurs because the interaction cross section increases as the charged particle's energy decreases." "The Bragg peak is a pronounced peak on the Bragg curve which plots the energy loss of ionizing radiation during its travel through matter. For protons . . . the peak occurs immediately before the particles come to rest." FIG. 18 is an example Bragg curve showing a Bragg peak 900 for a particular dose of proton therapy and depth.

Figure 18:
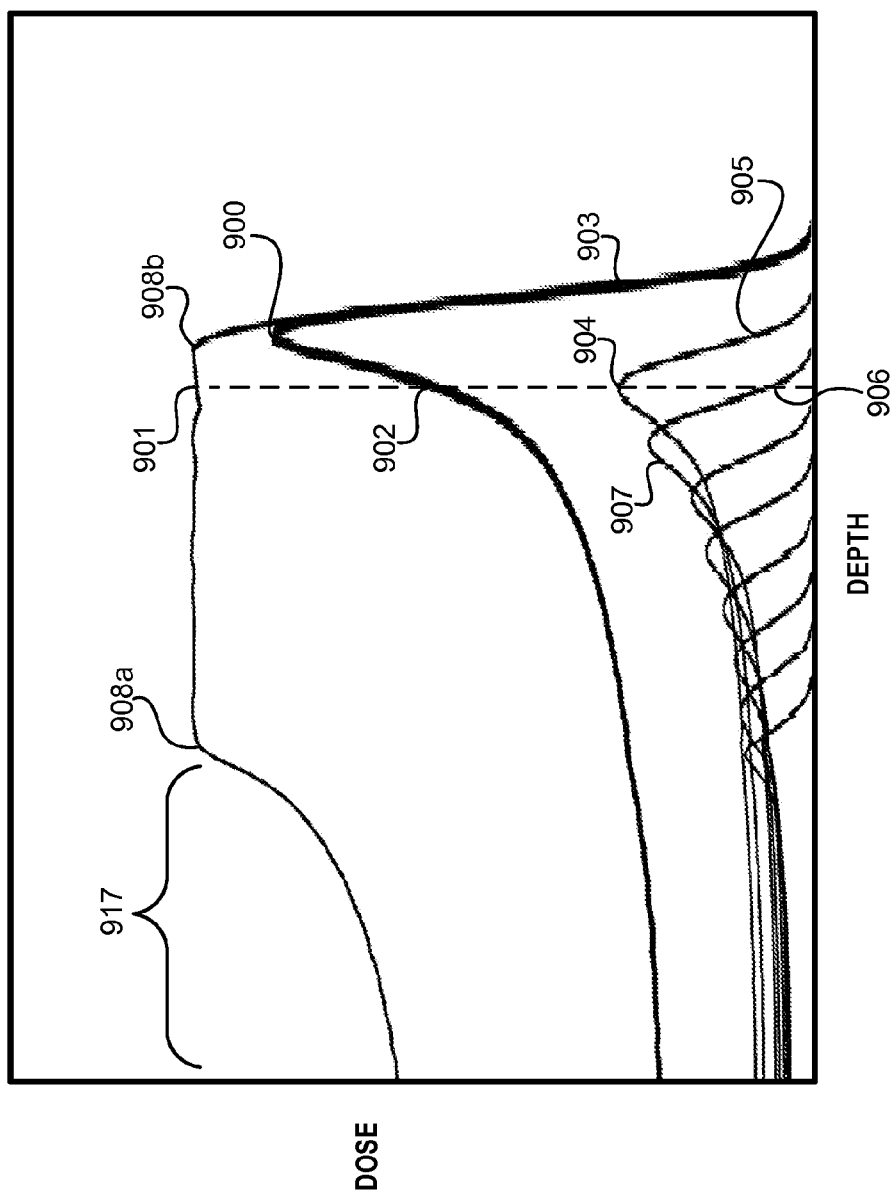
FIG. 18 is a graph showing various Bragg peaks and the cumulative effect that produces a spread-out Bragg peak.

To achieve a relatively uniform dose of particle therapy at a range of depths, a modulator device is configured to move Bragg peaks of the particle beam along the graph of FIG. 18 and to change the intensity of the Bragg peaks at the moved locations. Because particle therapy is cumulative, the resulting dosages may be added to obtain a substantially uniform dose. For example, referring to FIG. 18, the dosage at point 901 is the sum of doses at point 902 on Bragg curve 903, at point 904 on Bragg curve 905, and at point 906 on Bragg curve 907. Ideally, the result is a substantially uniform dose from depths 908*a* to 908*b*. This is referred to as a "spread-out Bragg peak", which extends depth-wise into a patient.

In some implementations, the modulator device used to spread-out the Bragg peaks is a structure, such as a modulator wheel, having different thicknesses at different locations along its circumference. Accordingly, the modulator wheel is rotatable in the path of, and relative to, the particle beam in order to provide the appropriate amount of particle therapy for a particular depth and area.

Figure 19:
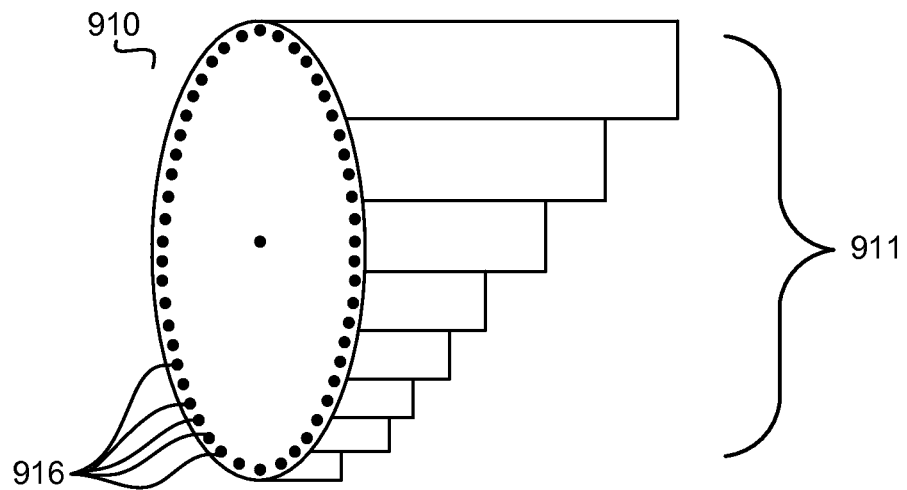
FIG. 19 is a side view of an example modulator wheel for producing Bragg peaks at different depths and intensity levels.
Figure 20:
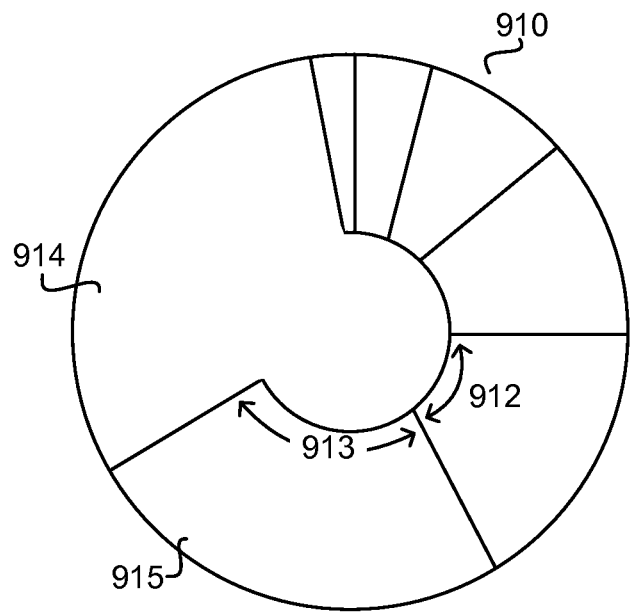
FIG. 20 is a top view of the modulator wheel of FIG. 19.

FIG. 19 shows a perspective view of an example modulator wheel 910 and FIG. 20 shows a top view of modulator wheel 910. As shown in the figures, the modulator wheel 910 has numerous steps 911, each with a different thickness (e.g., varying from zero or substantially zero thickness to a thickness on the order of centimeters or more). The thicknesses are used to vary the depth of corresponding Bragg peaks. For example, the least amount of thickness produces a Bragg peak with the most depth, the greatest amount of thickness produces a Bragg peak with the least depth, and so forth. As shown in FIG. 20 the angles (e.g., 912, 913, etc.) of the various steps also vary, resulting in different circumferential lengths for at least some of, and in some cases all of, the steps. The angle of each step adjusts how much the corresponding Bragg peak subtends within the patient. For example, the Bragg peak with the most intensity (e.g., Bragg peak 900 of FIG. 18) is the one that subtends the most. Accordingly, its corresponding step 914 has the largest angular extent. The Bragg peak with the next most intensity (e.g., Bragg peak 904 of FIG. 18) is the one that subtends the next most. Accordingly, its corresponding step 915 has the next largest angular extent; and so forth.

The modulator wheel may have constant, substantially constant, or variable rotation in order to provide the appropriate Bragg peak spreading for a prescription. In some implementations, the particle therapy system may include more than one modulator wheel of the type shown in FIGS. 27 and 28. The modulator wheels may be switchable into, and out of, the beam path by a modulator wheel control system (1518 of FIG. 15) in order to achieve a desired particle beam dose at a particular patient depth. For example, a first modulator wheel may be used for a first depth or range of depths (e.g., 10 cm to 15 cm); a second modulator wheel may be used for a second depth or range of depths (e.g., 15 cm to 20 cm); a third modulator wheel may be used for a third depth or range of depths (e.g., 20 cm to 25 cm); and so forth. In some implementations, there may be twelve modulator wheels, each of which may be calibrated for a different depth range; however, in other implementations, more or less than twelve modulator wheels may be used. Treatment depth is also dependent upon the particle beam intensity, which is a function of the ion (or particle) source pulse width, as described below.

The modulator wheels may be designed to provide uniform spread-out Bragg peaks from a maximum depth to the surface of a patient (e.g., to the outer layer of the patient's skin). To customize the depth of dosage, Bragg peaks in undesired locations (e.g., in area 917 in FIG. 18) may be "turned-off". This may be done by turning-off the RF source, turning-off the particle source, or turning-off both at an appropriate time during each rotation of the modulator wheel.

Particle source pulse width also has an effect on spread-out Bragg peak uniformity. As background, the amount of time that a particle source is intermittently (e.g., periodically) activated is varied, thereby providing the plasma column for different periods of time and enabling extraction of different numbers of particles. For example, if the pulse width is increased, the number of particles extracted increases and, if the pulse width decreases, the number of particles extracted decreases. In some implementations, there is a linear relationship between the time that the particle source is on and the intensity of the particle beam. For example, the relationship may be one-to-one plus an offset. In an example implementation, the particle source may be pulsed within a frequency window that occurs during a frequency sweep between a maximum frequency of about 135 MHz and a minimum frequency of about 95 MHz or 90 MHz. For example, the particle source may be pulsed between 132 MHz and 131 MHz for a period of time. In an implementation, this period of time is about 40 us; however, these values may vary or be different in other implementations. Failing to pulse the particle source outside of the frequency window can inhibit extraction of particles from the plasma column.

Figure 21:
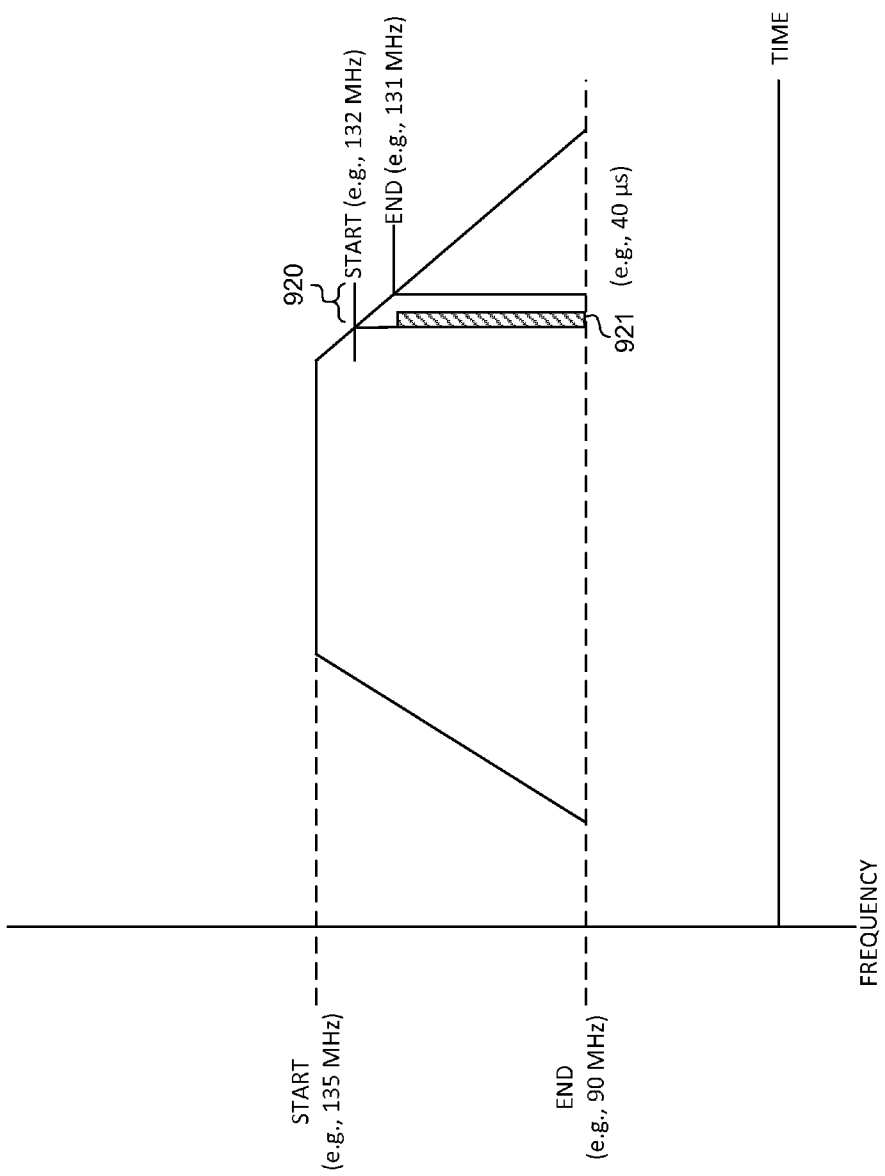
FIG. 21 is a graph showing a frequency sweep and a particle source pulse width output during a period of the frequency sweep.

FIG. 21 is a graph showing the voltage sweep in the resonant cavity over time from a maximum frequency (e.g., 135 MHz) to a minimum frequency (e.g., 90 MHz or 95 MHz). The extraction window 920 occurs, in this example, between 132 MHz and 131 MHz. The width of pulse 921 (the particle source pulse width) may be varied (e.g., by controlling the "on" time of the particle source) to control the intensity of the particle beam output by the particle accelerator.

Figure 22:
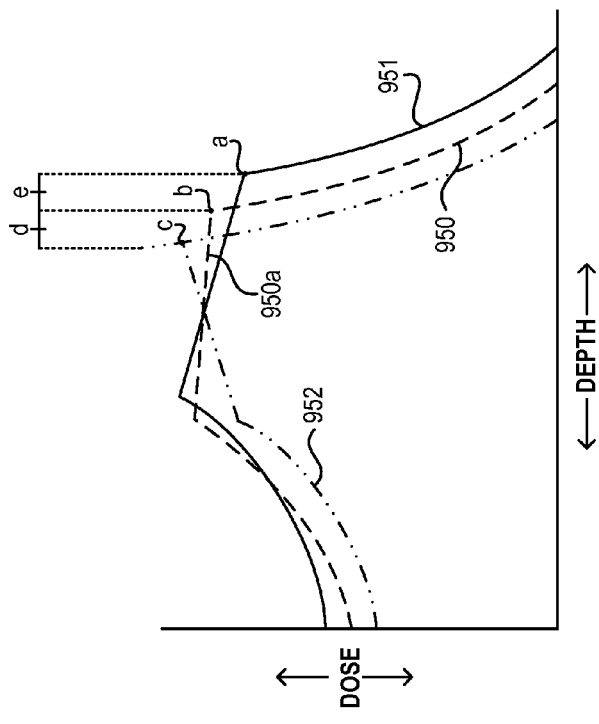
FIG. 22 is a graph showing spread-out Bragg peaks at different depths within a patient.

Particle source pulse widths may be adjustable in order to achieve substantial uniformity in spread-out Bragg peaks. In this regard, various factors, such as particle beam intensity, may contribute to the depth at which Bragg peaks penetrate a patient. A selected modulator wheel can produce different Bragg curves for different depths. For example, FIG. 22 shows Bragg curves for three different depths. Bragg curve 950 is for the nominal (or predefined) depth for a modulator wheel; Bragg curve 951 is for the maximum depth for the modulator wheel; and Bragg curve 952 is for the minimum depth for the modulator wheel. Ideally, the spread-out Bragg peaks should be at about the nominal level regardless of depth.

Figure 23:
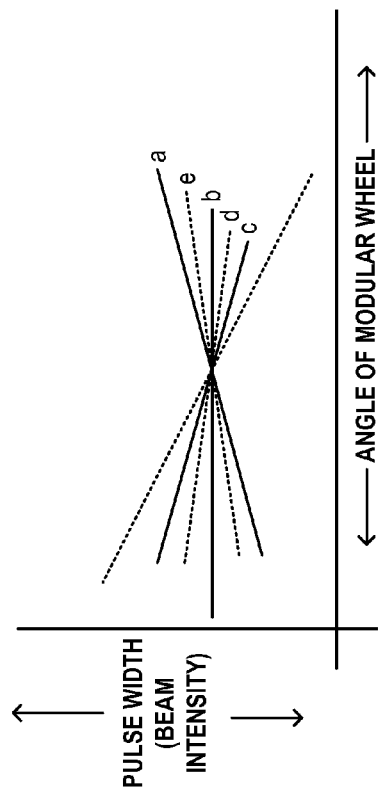
FIG. 23 is a graph showing particle source pulse width relative to the angle of the modulation wheel for the spread-out Bragg peaks of FIG. 22.

As shown in FIG. 22, Bragg curves 951 and 952 have spread-out Bragg peaks that are sloped. For Bragg curve 952, the slope is positive; and for Bragg curve 951 the slope is negative. To more closely approximate the nominal Bragg peak level at point b, the intensity of the particle beam is be increased at point a (to raise the Bragg peak at point a to the level at point b), and the intensity of the particle beam is be decreased at point c (to lower the Bragg peak at point c to the level of point b). The intensity of the particle beam is also be adjusted at points preceding a and c to either raise or lower the Bragg peaks at those points so that they coincide, at least to some degree, with the corresponding level of the nominal Bragg peak. The intensity of the particle beam may be changed by changing the particle source pulse width. However, different points along Bragg curves 951 and 952 require different amounts of adjustment in order to approximate the nominal spread-out Bragg peak of curve 950. Accordingly, in each instance, the pulse widths may be varied based on rotation of the modulator wheel. For example, at a point a when the modulator wheel impacts the particle beam, the pulse width may be increased more than at points preceding a along Bragg curve 951. Similarly, at a point c when the modulator wheel impacts the particle beam, the pulse width may be decreased more than at points preceding c along Bragg curve 952. For example, FIG. 23 is a plot showing the relationship between pulse width and rotational angle of the modulator wheel for Bragg curves 950, 951 and 952. Values have been omitted, since they are case specific.

Variations in pulse-width can be determined by obtaining the appropriate pulse widths at the beginning and ending of a Bragg peak, and linearly interpolating between the two to obtain variations in between. Other processes also may be used, as described below. To increase or decrease an overall dose, all pulse widths may be increased or decreased by a specified factor.

The modulator wheels may be switchable into, or out of, the beam path, as noted above. In an example, the modulator wheel control system (1518 of FIG. 15) can include one or more motors and a modulator wheel rack. An example slow I/O module 1510 can send machine instructions to motor controllers 1530 depending on which modulator wheel is appropriate (e.g., based on the translated prescription). Each motor controller 1530 can control a motor. For example, a motor can move the modulator wheel rack side to side until the selected modulator wheel is in position, and another motor can move the modulator wheel into, or out of, the beam path. In other implementations, the modulator wheel rack may be below the beam path, and an appropriate modulator wheel may be positioned proximate the beam path, and thereafter moved into the beam path by another motor.

Referring back to FIG. 15, a fast I/O module 1522 can be used to control components of the particle accelerator that require relatively fast transmission (e.g., the particle source 1524 and the RF voltage source). The fast I/O module can include a microprocessor 1522a for communicating with the real-time operating system 1508a of the MCC 1508, and a field-programmable gate array (FPGA) 1522b for sending and receiving information to/from the particle accelerator components. A modulator wheel communication line can also send information to the FPGA (1522b) pertaining to the modulator wheel. In an example, the modulator wheel communication line 1528 is an optical fiber 1528 that includes a sensor configured to monitor the modulator wheel.

As explained above, the modulator wheels may be configured to provide uniform spread-out Bragg peaks from a maximum depth to the surface of a patient (e.g., to the outer layer of the patient's skin). To affect the dosage, the particle source may be turned on and off at appropriates time during each rotation of the modulator wheel. This process is known as "pulse blanking".

In some implementations, the particle source has a pulse frequency of about 500 pulses-per-second, with about 10 nano-amperes (nA) of current per-pulse. In other implementations, the number of pulses-per-second, and current per-pulse may be different than these numbers. In some implementations, a modulator wheel rotates such that each step of the modulator wheel (corresponding one of plural different thicknesses) receives multiple pulses on each step during rotation. The dosage for each step corresponds to the number of pulses received by that step.

The number of pulses applied to a target corresponds to the radiation dose at the target, and can have an effect on spread-out Bragg peak uniformity. More specifically, modulator wheels may be calibrated to provide dosage at specific tissue depths. For example, the thicknesses of wheel steps may be calibrated, based on an expected dose, to provide spread-out Bragg peaks over a range of depths, ideally to result in a uniform dose approximating something like that shown in FIG. 18. However, in practice, variations in tissues and materials (for example) may result in Bragg curves (i.e., depth dose distributions) that are non-uniform or that are sloped. FIG. 22, described above, shows examples of Bragg curves that are sloped, which could possibly result from such modulator wheels.

More specifically, as explained above, a selected modulator wheel can produce different Bragg curves for different tissue depths. For example, FIG. 22 shows Bragg curves for three different depths. Bragg curve 950 is for the nominal (or predefined) depth for a modulator wheel; Bragg curve 951 is for the maximum depth for the modulator wheel; and Bragg curve 952 is for the minimum depth for the modulator wheel. Ideally, the spread-out Bragg peaks should be at about the nominal level regardless of depth.

As shown in FIG. 22, Bragg curves 951 and 952 have spread-out Bragg peaks that are sloped. For Bragg curve 952, the slope is positive; and for Bragg curve 951 the slope is negative. To more closely approximate the nominal Bragg peak level at point b, the relative dosage of the particle beam (e.g., the number of pulses) may be increased at point a (to raise the Bragg peak at point a to the level at point b), and the relative dosage (e.g., the number of pulses) of the particle beam may be decreased at point c (to lower the Bragg peak at point c to the level of point b). The relative dosages of the particle beam may also be adjusted at points preceding a and c to either raise or lower the Bragg peaks at those points so that they coincide, at least to some degree, with the corresponding level of the nominal Bragg peak. In this regard, different points along Bragg curves 951 and 952 require different amounts of adjustment in order to approximate the nominal spread-out Bragg peak of curve 950. Accordingly, in each instance, the relative dosage (e.g., the number of pulses) may be varied based on, and corresponding to, rotation of the modulator wheel. For example, at a point a when the modulator wheel impacts the particle beam, the relative dosage (e.g., number of pulses) may be increased more than at points preceding a along Bragg curve 951. Similarly, at a point c when the modulator wheel impacts the particle beam, the relative dosage (e.g., number of pulses) may be decreased more than at points preceding c along Bragg curve 952. The dosage applications are analogous to FIG. 23, which is described above for pulse width variations Variations in dosage to obtain uniform Bragg curves can be determined by obtaining the dosages at the beginning and ending of a Bragg peak, and linearly interpolating between the two to obtain variations in between. This information may be obtained as part of a calibration process. Other processes also may be used, as described below.

To increase or decrease an overall dose, the particle source and/or other feature(s) of the particle therapy system may be used to control the number of output pulses. For example, the particle source may be turned off to reduce the number of output of pulses to the modulator wheel, and the particle source may be turned on to increase the number of output pulse of the particle beam to the modulator wheel. This control may be performed at a certain step or steps (e.g., sectors) of the modulator wheel to obtain the desired result, e.g., increased or decreased dosage and, therefore, an increase or decrease in the slope of the corresponding Bragg curve. Dosage may also be applied or withheld to correct for holes or spikes in the Bragg curves. Control over the various aspects of the system may be performed by the slow and fast I/O modules described above. In other implementations, different control systems may be used.

As noted, in some implementations, the number of pulses may be varied by turning-on or turning-off the particle source at appropriate times during rotation of the modulator wheel. In some implementations, other features are used to control the number of pulses that are applied to particular sectors of the modulator wheel. For example, the RF voltage sweep may be interrupted intermittently, thereby reducing the number of pulses (since a pulse is typically output per sweep). To increase the number of pulses, the rate of the sweep may be increased. In another example, additional hardware may be used to control the number of pulses. For example, a steering mechanism, such as a kicker magnet, may be used to reduce the output of pulses for particular rotations of the modulator wheel. In some implementations, a kicker magnet (or other structure) may direct a set (e.g., every other, every third, and so forth) of pulses to an absorber material, thereby preventing their output to the irradiation target.

To obtain a flat, or substantially flat, Bragg curve, as explained herein it may be necessary to increase or decrease the relative number of pulses applied to particular sectors of a modulator wheel. The increase or decrease may be relative to amounts of pulses applied to other sectors of the modulator wheel. For example, a decrease in the number of pulses applied to all sectors of a modulator wheel but not to one sector has a similar effect as an increase in the number of pulses applied to that one sector of the modulator wheel. Such relative changes to the applied numbers of pulses may be used to obtain the appropriate increase and decreases to change a Bragg curve. In cases where the numbers of pulses have been decreased to obtain a relative increase in one sector, the overall dose applied may be reduced. In those situations, the particle therapy system may require a longer irradiation time to achieve the required overall dosage for a particular target.

In some implementations, the particle therapy system may include a scanning system to scan the particle beam across a cross-section of an irradiation target. This is done at different depths to treat the entire irradiation target. In implementations that involve scanning, pulse blanking of the type described herein may be used on a spot-by-spot basis. That is, during scanning, a particle beam is applied at a spot, then the particle beam is moved (typically by a magnet) to a next spot on the irradiation target. Pulse blanking may be used to control the number of pulses applied to each spot. Generally, spot scanning involves applying irradiation at discrete spots on an irradiation target and raster scanning involves moving a radiation spot across the radiation target. The concept of spot size therefore applies for both raster and spot scanning.

Referring back to FIG. 19, the example modulator wheel 910 may have multiple markings 916 around its edge. The markings 916 can be any shape and can have any configuration. Particular markings 916 can signify particular modulator wheel 910 positions. In an example, the exact position of the modulator wheel 910 can be determined by identifying the markings 916. In another example, the markings 916 are configured such that the rotational speed of the modulator wheel 910 can be determined by only looking at the markings 916.

A first end of the optical fiber 1528 (e.g., the end that includes the sensor) can be situated in a position where it can detect the markings 916 on the modulator wheel 910. A second end of the optical fiber 1528 can be connected to the FPGA 1522b and be configured to communicate information pertaining to the modulator wheel 910 (e.g., its position and rotational speed).

The FPGA 1522b may also be configured to send and receive information from the particle source 1524 and the RF voltage source 1526. As explained above, the depth of dosage (e.g., based on the translated prescription) can be customized by "turning-off" Bragg peaks in undesired locations (e.g., in area 917 in FIG. 18). This may be done by turning-off the RF source, turning-off the particle source, or turning-off both at an appropriate time during each rotation of the modulator wheel 910. The FPGA 1522b can communicate the information the FPGA 1522b receives from the optical fiber 1528 to the microprocessor 1522a (which in turn communicated with the real-time operating system 1508a of the MCC 1508) and receive instructions from the microprocessor 1522a regarding particle source 1524 and RF voltage source 1526 control. For example, the FPGA 1522b may tell the particle source 1524 and/or the RF voltage source 1526 to turn on/off when the modulator wheel 910 is in a particular position or positions. The FPGA 1522b may also tell the particle source 1524 how long to make the particle source pulse widths based on the rotational position of the modulator wheel.

As mentioned above, the fast I/O module 1522 can also receive information from the particle source 1524 and the RF voltage source 1526. A fast I/O module 1522 is desirable for controlling these components because their operation is time sensitive. Referring back to FIG. 21, the extraction window 920 is created by pulsing the particle source over a particular frequency range. In some examples, this frequency range is very small (e.g., less than a 1 MHz window). The fast I/O module 1522 can also receive information from the RF voltage source 1526 and the particle source 1524 in addition to the information it receives about the modulator wheel 910. The RF voltage source 1526 can continuously communicate its frequency to the fast I/O module 1522. The fast I/O module can then tell the particle source 1524 to turn on when it learns that the RF voltage source is at a particular frequency or the modulator wheel is at a particular location, and to turn off when it learns that the RF voltage source is at a particular frequency or the modulator wheel is at a particular location. The fast I/O module 1522 can also use received information (e.g., the rotational position of the modulator wheel) to tell the particle source 1524 how long to make the particle source pulse widths.

Aspects of the control system are system specific and may vary depending on the type of treatment (e.g., the prescription).

Elements of different implementations described herein may be combined to form other implementations not specifically set forth above. Elements may be left out of the processes, systems, apparatus, etc., described herein without adversely affecting their operation. Various separate elements may be combined into one or more individual elements to perform the functions described herein.

The example implementations described herein are not limited to use with a particle therapy system or to use with the example particle therapy systems described herein. Rather, the example implementations can be used in any appropriate system that directs accelerated particles to an output.

Additional information concerning the design of an example implementation of a particle accelerator that may be used in a system as described herein can be found in U.S. Provisional Application No. 60/760,788, entitled "High-Field Superconducting Synchrocyclotron" and filed Jan. 20, 2006; U.S. patent application Ser. No. 11/463,402, entitled "Magnet Structure For Particle Acceleration" and filed Aug. 9, 2006; and U.S. Provisional Application No. 60/850,565, entitled "Cryogenic Vacuum Break Pneumatic Thermal Coupler" and filed Oct. 10, 2006, all of which are incorporated herein by reference.

The following applications, all of which are filed on the same date as the subject application (entitled "CONTROL SYSTEM FOR A PARTICLE ACCELERATOR" (Application No. 61/707,645)), are incorporated by reference into the subject application: the U.S. Provisional Application entitled "CONTROLLING INTENSITY OF A PARTICLE BEAM" (Application No. 61/707,466 filed on Sep. 29, 2012), the U.S. Provisional Application entitled "ADJUSTING ENERGY OF A PARTICLE BEAM" (Application No. 61/707,515, filed on Sep. 28, 2012), the U.S. Provisional Application entitled "ADJUSTING COIL POSITION" (Application No. 61/707,548, filed on Sep. 28, 2012), the U.S. Provisional Application entitled "FOCUSING A PARTICLE BEAM USING MAGNETIC FIELD FLUTTER" (Application No. 61/707,572, filed on Sep. 28, 2012), the U.S. Provisional Application entitled "MAGNETIC FIELD REGENERATOR" (Application No. 61/707,590, filed on Sep. 28, 2012), the U.S. Provisional Application entitled "FOCUSING A PARTICLE BEAM" (Application No. 61/707,704, filed on Sep. 28, 2012), and the U.S. Provisional Application entitled "CONTROLLING PARTICLE THERAPY (Application No. 61/707,624, filed on Sep. 28, 2012).

The following are also incorporated by reference into the subject application: U.S. Pat. No. 7,728,311 which issued on Jun. 1, 2010, U.S. patent application Ser. No. 11/948,359 which was filed on Nov. 30, 2007, U.S. patent application Ser. No. 12/275,103 which was filed on Nov. 20, 2008, U.S. patent application Ser. No. 11/948,662 which was filed on Nov. 30, 2007, U.S. Provisional Application No. 60/991,454 which was filed on Nov. 30, 2007, U.S. Pat. No. 8,003,964 which issued on Aug. 23, 2011, U.S. Pat. No. 7,208,748 which issued on Apr. 24, 2007, U.S. Pat. No. 7,402,963 which issued on Jul. 22, 2008, U.S. patent application Ser. No. 13/148,000 filed Feb. 9, 2010, U.S. patent application Ser. No. 11/937,573 filed on Nov. 9, 2007, U.S. patent application Ser. No. 11/187,633, titled "A Programmable Radio Frequency Waveform Generator for a Synchrocyclotron," filed Jul. 21, 2005, U.S. Provisional Application No. 60/590,089, filed on Jul. 21, 2004, U.S. patent application Ser. No. 10/949,734, titled "A Programmable Particle Scatterer for Radiation Therapy Beam Formation", filed Sep. 24, 2004, and U.S. Provisional Application No. 60/590,088, filed Jul. 21, 2005.

Any features of the subject application may be combined with one or more appropriate features of the following: the U.S. Provisional Application entitled "CONTROLLING INTENSITY OF A PARTICLE BEAM" (Application No. 61/707,466 filed on Sep. 29, 2012), the U.S. Provisional Application entitled "ADJUSTING ENERGY OF A PARTICLE BEAM" (Application No. 61/707,515, filed on Sep. 28, 2012), the U.S. Provisional Application entitled "ADJUSTING COIL POSITION" (Application No. 61/707,548, filed on Sep. 28, 2012), the U.S. Provisional Application entitled "FOCUSING A PARTICLE BEAM USING MAGNETIC FIELD FLUTTER" (Application No. 61/707,572, filed on Sep. 28, 2012), the U.S. Provisional Application entitled "MAGNETIC FIELD REGENERATOR" (Application No. 61/707,590, filed on Sep. 28, 2012), the U.S. Provisional Application entitled "FOCUSING A PARTICLE BEAM" (Application No. 61/707,704, filed on Sep. 28, 2012), the U.S. Provisional Application entitled "CONTROLLING PARTICLE THERAPY (Application No. 61/707,624, filed on Sep. 28, 2012), U.S. Pat. No. 7,728,311 which issued on Jun. 1, 2010, U.S. patent application Ser. No. 11/948,359 which was filed on Nov. 30, 2007, U.S. patent application Ser. No. 12/275,103 which was filed on Nov. 20, 2008, U.S. patent application Ser. No. 11/948,662 which was filed on Nov. 30, 2007, U.S. Provisional Application No. 60/991,454 which was filed on Nov. 30, 2007, U.S. patent application Ser. No. 13/907,601, which was filed on May 31, 2013, U.S. patent application Ser. No. 13/916,401, filed on Jun. 12, 2013, U.S. Pat. No. 8,003,964 which issued on Aug. 23, 2011, U.S. Pat. No. 7,208,748 which issued on Apr. 24, 2007, U.S. Pat. No. 7,402,963 which issued on Jul. 22, 2008, U.S. patent application Ser. No. 13/148,000 filed Feb. 9, 2010, U.S. patent application Ser. No. 11/937,573 filed on Nov. 9, 2007, U.S. patent application Ser. No. 11/187,633, titled "A Programmable Radio Frequency Waveform Generator for a Synchrocyclotron," filed Jul. 21, 2005, U.S. Provisional Application No. 60/590,089, filed on Jul. 21, 2004, U.S. patent application Ser. No. 10/949,734, titled "A Programmable Particle Scatterer for Radiation Therapy Beam Formation", filed Sep. 24, 2004, and U.S. Provisional Application No. 60/590,088, filed Jul. 21, 2005.

Except for the provisional application from which this patent application claims priority and the documents incorporated by reference above, no other documents are incorporated by reference into this patent application.

Other implementations not specifically described herein are also within the scope of the following claims.

What is claimed is:

1. A particle therapy system comprising:
a particle accelerator to output a particle beam, comprising:
a particle source to provide pulses of ionized plasma to a cavity, each pulse of the particle source having a pulse width corresponding to a duration of operation of the particle source to produce the corresponding pulse, the particle beam being based on the pulses of ionized plasma; and
a modulator wheel having different thicknesses, each thickness extending across a different circumferential length of the modulator wheel, the modulator wheel being arranged to receive the particle beam and configured to create a spread-out Bragg peak for the particle beam;
one or more first input/output (I/O) modules operable at a first speed, the one or more first I/O modules being configured to send machine instructions to one or more motor controllers, at least one motor controller for controlling the modulator wheel; and
one or more second I/O modules operable at a second speed that is greater than the first speed, at least one of the second I/O modules being configured to send machine instructions to the particle source so that pulse widths of the particle source vary with rotational positions of the modulator wheel.

2. The particle therapy system of claim 1, further comprising:
a therapy control computer programmed to receive prescription information from a hospital, to translate the prescription information to machine information, and to send treatment records to the hospital; and
a master control computer having a real-time operating system, the master control computer programmed to receive machine information from the therapy control computer, to translate the machine information into machine instructions, and to send the machine instructions to one or more of the first I/O modules and the second I/O modules.

3. The particle therapy system of claim 2, further comprising an optical fiber over which are monitored a rotational speed and a position of the modulator wheel.

4. The particle therapy system of claim 1, wherein the one or more first I/O modules comprise programmable logic controllers (PLC).

5. The particle therapy system of claim 4, wherein at least one of the PLCs is programmed to send machine instructions to motor controllers for controlling a field shaping wheel system for shaping the particle beam prior to output.

6. The particle therapy system of claim 4, wherein at least one of the PLCs is programmed to send machine instructions to a motor controller for controlling a scattering system for scattering the particle beam prior to output.

7. The particle therapy system of claim 4, further comprising:
a radio frequency (RF) system to sweep RF frequencies through the cavity, the RF system comprising a rotating capacitor;
wherein at least one of the PLCs is programmed to send machine instructions to a motor controller that controls the rotating capacitor.

8. The particle therapy system of claim 1, wherein a speed of the one or more first I/O modules is on the order of milliseconds and a speed of the one or more second I/O modules is on the order of one or more hundreds of nanoseconds.

9. The particle therapy system of claim 4, further comprising:
a rotatable gantry on which the particle accelerator is mounted;
wherein at least one of the PLCs is programmed to send machine instructions to a motor controller that controls the rotatable gantry.

10. The particle therapy system of claim 4, wherein two or more of the PLCs are configured to communicate with one another.

11. The particle therapy system of claim 1, wherein the one or more second I/O modules comprise field-programmable gate arrays (FPGA).

12. The particle therapy system of claim 11, further comprising:
a circuit board comprising a microprocessor;
at least one of the FPGAs being on the circuit board and in communication with the microprocessor;
wherein the microprocessor is programmed to communicate with a control computer.

13. The particle therapy system of claim 11, further comprising:
a radio frequency (RF) system to sweep RF frequencies through the cavity to extract particles from a plasma column produced by the particle source;
wherein at least one of the FPGAs comprises an RF control module, the RF control module being configured to receive information about a rotation of the modulator wheel and, based thereon, to coordinate operational aspects of the particle source and the RF system.

14. The particle therapy system of claim 13, wherein coordinating operational aspects of the particle source and the RF system comprises turning the particle source on or off based on a rotational position of the modulator wheel, and turning the RF system on or off based on a rotational position of the modulator wheel.

15. The particle therapy system of claim 14, wherein the RF control module is further configured to send machine instruction to the particle source to turn-on when an RF voltage is at a certain frequency and to turn-off when the RF voltage is at a certain frequency.

16. The control system of claim 14, wherein coordinating operational aspects of the particle source comprises specifying pulse widths during turn-on times of the particle source.

17. A particle therapy system comprising:
a particle accelerator to output a particle beam, comprising:
a particle source to provide pulses of ionized plasma to a cavity, each pulse of the particle source having a pulse width corresponding to a duration of operation of the particle source to produce the corresponding pulse, the particle beam being based on the pulses of ionized plasma; and
a modulator wheel having different thicknesses, each thickness extending across a different circumferential length of the modulator wheel, the modulator wheel being arranged to receive the particle beam and being configured to create a spread-out Bragg peak for the particle beam;

wherein the modulator wheel, as configured, produces different spread-out Bragg peaks at different depths within a patient, the different spread-out Bragg peaks deviating from predefined spread-out Bragg peak for the modulator wheel for a given depth application in the patient; and wherein the particle therapy system is configured so that, for different depth applications within the patient, pulse widths of the particle source vary with rotational positions of the modulator wheel in order to produce spread-out Bragg peaks that approximate the predefined spread-out Bragg peak.

18. The particle therapy system of claim 17, further comprising:
a therapy control computer programmed to receive prescription information from a hospital, to translate the prescription information to machine information, and to send treatment records to the hospital; and
a master control computer programmed to receive machine information from the therapy control computer, to translate the machine information into machine instructions, and output the machine instructions to control at least some operation of the particle therapy system.

19. The particle therapy system of claim 17, further comprising an optical fiber over which are monitored a rotational speed and position of the modulator wheel.

20. The particle therapy system of claim 17, further comprising programmable logic controllers (PLC).

21. The particle therapy system of claim 20, wherein at least one of the PLCs is programmed to send machine instructions to a motor controller for controlling a field shaping wheel system for shaping the particle beam prior to output.

22. The particle therapy system of claim 20, wherein at least one of the PLCs is programmed to send machine instructions to a motor controller for controlling a scattering system for scattering the particle beam prior to output.

23. The particle therapy system of claim 20, further comprising:
a radio frequency (RF) system to sweep RF frequencies through the cavity, the RF system comprising a rotating capacitor;
wherein at least one of the PLCs is programmed to send machine instructions to a motor controller to control the rotating capacitor.

24. The particle therapy system of claim 20, further comprising:
a device on which the particle accelerator is mounted for movement;
wherein at least one of the PLCs is programmed to send machine instructions to a motor controller that controls operation of the device to control movement of the particle accelerator.

25. The particle therapy system of claim 17, further comprising:
a radio frequency (RF) system to sweep RF frequencies through the cavity; the RF system comprising an RF control module, the RF control module being configured to receive information about a rotation of the modulator wheel and, based thereon, to coordinate operational aspects of the particle source and the RF system.

* * * * *